United States Patent
Xu et al.

(10) Patent No.: US 6,261,562 B1
(45) Date of Patent: Jul. 17, 2001

(54) COMPOUNDS FOR IMMUNOTHERAPY OF PROSTATE CANCER AND METHODS FOR THEIR USE

(75) Inventors: Jiangchun Xu, Bellevue; Davin C. Dillon, Redmond, both of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/020,956

(22) Filed: Feb. 9, 1998

Related U.S. Application Data

(63) Continuation-in-part of application No. 08/904,804, filed on Aug. 1, 1997, which is a continuation-in-part of application No. 08/806,099, filed on Feb. 25, 1997.

(51) Int. Cl.$^7$ ............... A61K 39/00; A61K 38/00; A01N 37/18; C07K 16/00; C07K 17/00

(52) U.S. Cl. ............... 424/185.1; 514/2; 514/12; 530/324

(58) Field of Search ............... 530/324; 424/185.1; 514/2, 12

(56) References Cited

U.S. PATENT DOCUMENTS

| 5,786,148 | 7/1998 | Bandman et al. | 435/6 |
|---|---|---|---|

FOREIGN PATENT DOCUMENTS

| 19649207 | 11/1996 | (DE) . |
|---|---|---|
| 317 141 A2 | 5/1989 | (EP) . |
| 652 014 A1 | 5/1995 | (EP) . |
| 936 270 A2 | 8/1999 | (EP) . |
| WO 93/14755 | 8/1993 | (WO) . |
| WO 93/25224 | 12/1993 | (WO) . |
| WO 94/09820 | 5/1994 | (WO) . |
| WO 95/04548 | 2/1995 | (WO) . |
| WO 95/14772 | 6/1995 | (WO) . |
| WO 95/30758 | 11/1995 | (WO) . |
| WO 96/21671 | 7/1996 | (WO) . |
| WO 97/33909 | 9/1997 | (WO) . |
| WO 98/12302 | 3/1998 | (WO) . |
| WO 98/17687 | 4/1998 | (WO) . |
| WO 98/20117 | 5/1998 | (WO) . |
| WO 98/31799 | 7/1998 | (WO) . |
| WO 98/37093 | 8/1998 | (WO) . |
| WO 98/37418 | 8/1998 | (WO) . |
| WO 98/38310 | 9/1998 | (WO) . |
| WO 98/39446 | 9/1998 | (WO) . |
| WO 98/45435 | 10/1998 | (WO) . |
| WO 98/50567 | 11/1998 | (WO) . |
| WO 99/06548 | 2/1999 | (WO) . |
| WO 99/06550 | 2/1999 | (WO) . |
| WO 99/06552 | 2/1999 | (WO) . |
| WO 99/25825 | 5/1999 | (WO) . |
| WO 99/31236 | 6/1999 | (WO) . |

OTHER PUBLICATIONS

Ahn and Kunkel, "The structural and functional diversity of dystrophin", *Nature Genetics* 3: 283–291, Apr., 1993.

Cawthon et al., "cDNA sequence and genomic structure of EV12B, a gene lying within an intron of the neurofibromatosis type 1 gene," *Genomics* 9:446–460, 1991.

Chu et al., "CpG oligodeoxynucleotides act as adjuvants that switch on T helper 1 (Th1) immunity," *J. Exp. Med.* 186(10): 1623–1631, Nov. 17, 1997.

Coleman et al., *Fundamental Immunology*, Wm. C. Brown Publishers, Dubuque, Iowa, 1989, pp. 465–466.

Duerst and Nees, "Nucleic acid characteristic of late or early passage cells immortalized by papilloma virus–and related polypeptide(s) and antibodies, used for diagnosis and treatment of cervical cancer and assessing potential for progression of cervical lesions", Derwent World Patent Index, Accession No. 1998–121623, 1998. See also German Patent DE 19649207 C1.

Harris et al., "Polycystic Kidney Disease 1: identification and analysis of the primary defect," *J. Am. Soc. of Nephrol.* 6:1125–1133, 1995.

Hillier et al., Genbank Accession No. AA100799, Dec. 23, 1997.

Hillier et al., Genbank Accession No. R20590, Apr. 18, 1995.

Hudson, T., Genbank Accession No. G22461, May 31, 1996.

Kroger, B. "New serine protease form human prostate, useful for identifying specific inhibitors, antibodies and probes", Derwent World Patent Index, Accession No. 99–432218, 1999. See also European Patent EP 936 270 A2.

National Cancer Institute, Cancer Genome Anatomy Project (NCI–CGAP), Genbank Accession No. AA551449, Sep. 5, 1997.

National Cancer Institute, Cancer Genome Anatomy Project (NCI–CGAP), Genbank Accession No. AA551759, Aug. 11, 1997.

National Cancer Institute, Cancer Genome Anatomy Project (NCI–CGAP), Genbank Accession No. AA631143, Oct. 31, 1997.

National Cancer Institute, Cancer Genome Anatomy Project (NCI–CGAP), Genbank Accession No. AA653016, Nov. 25, 1997.

(List continued on next page.)

*Primary Examiner*—Anthony C. Caputa
*Assistant Examiner*—Jennifer Nichols
(74) *Attorney, Agent, or Firm*—Seed Intellectual Property Law Group PLLC

(57) ABSTRACT

Compounds and methods for treating prostate cancer are provided. The inventive compounds include polypeptides containing at least a portion of a prostate tumor protein. Vaccines and pharmaceutical compositions for immunotherapy of prostate cancer comprising such polypeptides, or DNA molecules encoding such polypeptides, are also provided, together with DNA molecules for preparing the inventive polypeptides.

14 Claims, No Drawings

OTHER PUBLICATIONS

Sjögren, H., "Therapeutic Immunization Against Cancer Antigens Using Genetically Engineered Cells," *Immunotechnology* 3: 161–172, 1997.

Zitvogel et al., "Eradication of Established Murine Tumors Using a Novel Cell–Free Vaccine: Dendritic Cell–Derived Exosomes," *Nature Medicine* 4(5): 594–600, May, 1998.

Derwent Geneseq Database, Accession No. V58522, Dec. 8, 1998.

Derwent Gensesq Database, Accession No. V61287, Jan. 6, 1999.

Alexeyev et al., "Improved antibiotic–resistance gene cassettes and omega elements for *Escherichia coli* vector construction and in vitro deletion/insertion mutagenesis," *Gene* 160: 63–67, 1995.

Blok et al., "Isolation of cDNAs That Are Differentially Expressed Between Androgen–Dependent and Androgen–Independent Prostate Carcinoma Cells Using Differential Display PCR," *The Prostate* 26: 213–224, 1995.

Database EMBL Accession No. AA453562, Jun. 11, 1997, Hillier et al., "Homo Sapiens cDNA Clone 788180".

El–Shirbiny, Prostatic Specific Antigen, *Advances In Clinical Chemisty* 31: 99–133, 1994.

Robson et al., "Identification of prostatic androgen regulated genes using the differential display technique," *Proceedings Of The American Association For Cancer Research Meeting* 86, 36: p. 266, Abstract No. 1589, 1995.

Short et al., "λ ZAP: a bacteriophage λ expression vector with in vivo excision properties," *Nucleic Acids Research* 16(15): 7583–7600, 1988.

Ezell. "Cancer vaccines: an idea whose time has come'" TheJournal of NIH Research. vol. 7, pp. 46–49, Jan. 1995.*

* cited by examiner

US 6,261,562 B1

COMPOUNDS FOR IMMUNOTHERAPY OF PROSTATE CANCER AND METHODS FOR THEIR USE

REFERENCE TO RELATED APPLICATIONS

This application is a continuation-in-part of U.S. patent application Ser. No. 08/904,804, filed Aug. 1, 1997, which is a continuation-in-part of U.S. patent application Ser. No. 08/806,099, filed Feb. 25, 1997.

TECHNICAL FIELD

The present invention relates generally to compositions and methods for the treatment of prostate cancer. The invention is more particularly related to polypeptides comprising at least a portion of a prostate protein and to DNA molecules encoding such polypeptides. Such polypeptides may be used in vaccines and pharmaceutical compositions for treatment of prostate cancer.

BACKGROUND OF THE INVENTION

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into therapies for the disease, prostate cancer remains difficult to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have limited therapeutic and diagnostic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

Accordingly, there remains a need in the art for improved vaccines and treatment methods for prostate cancer.

SUMMARY OF THE INVENTION

The present invention provides compounds and methods for immunotherapy of prostate cancer. In one aspect, polypeptides are provided comprising at least an immunogenic portion of a prostate tumor protein or a variant of said protein that differs only in conservative substitutions and/or modifications, wherein the prostate tumor protein comprises an amino acid sequence encoded by a DNA molecule having a sequence selected from the group consisting of nucleotide sequences recited in SEQ ID NO: 2, 3, 8–29, 41–45, 47–52, 54–65, 70, 73–74, 79, 81, 87, 90, 92, 93, 97, 103, 104, 107, 109–111, 115–160, 171, 173–175, 177, the complements of said nucleotide sequences and variants thereof.

In related aspects, DNA molecules encoding the above polypeptides are provided. In specific embodiments, such DNA molecules include sequences provided in SEQ ID NO: 2, 3, 8–29, 41–45, 47–52, 54–65, 70, 73–74, 79, 81, 87, 90, 92, 93, 97, 103, 104, 107, 109–111, 115–160, 171, 173–175, 177. The present invention further provides expression vectors comprising the above DNA molecules and host cells transformed or transfected with such expression vectors. In preferred embodiments, the host cells are selected from the group consisting of $E.$ $coli,$ yeast and mammalian cells.

In another aspect, the present invention provides fusion proteins comprising a first and a second inventive polypeptide or, alternatively, an inventive polypeptide and a known prostate antigen.

The present invention also provides pharmaceutical compositions comprising one or more of the above polypeptides, or a DNA molecule encoding such polypeptides, and a physiologically acceptable carrier, together with vaccines comprising one or more of such polypeptide or DNA molecules in combination with a non-specific immune response enhancer.

In related aspects, pharmaceutical compositions for the treatment of prostate cancer comprising one or more polypeptides and a physiologically acceptable carrier are provided, wherein the polypeptide comprises an immunogenic portion of a prostate tumor protein or of a variant of said protein that differs only in conservative substitutions and/or modifications, the prostate tumor protein being encoded by a DNA molecule having a sequence selected from the group consisting of nucleotide sequences recited in SEQ ID NO: 5–7, 30–40, 46, 53, 66–69, 71, 72, 75–78, 80, 82–86, 88, 89, 91, 94–96, 98–102, 105, 106 and 161–170, the complements of said nucleotide sequences and variants thereof. The invention also provides vaccines for the treatment of prostate cancer comprising such polypeptides in combination with a non-specific immune response enhancer, together with pharmaceutical compositions and vaccines comprising one or more DNA molecules having a sequence provided in SEQ ID NO: 5–7, 30–40, 46, 53, 66–69, 71, 72, 75–78, 80, 82–86, 88, 89, 91, 94–96, 98–102, 105, 106 and 161–170. Pharmaceutical compositions and vaccines comprising one or more of the above fusion proteins are also provided.

In yet another aspect, methods are provided for inhibiting the development of prostate cancer in a patient, comprising administering an effective amount of at least one of the above pharmaceutical compositions and/or vaccines.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

As noted above, the present invention is generally directed to compositions and methods for the immunotherapy of prostate cancer. The inventive compositions are generally polypeptides that comprise at least a portion of a prostate tumor protein. Also included within the present invention are molecules (such as an antibody or fragment thereof) that bind to the inventive polypeptides. Such molecules are referred to herein as "binding agents."

In particular, the subject invention discloses polypeptides comprising at least a portion of a human prostate tumor protein, or a variant of such a protein that differs only in conservative substitutions and/or modifications, wherein the prostate tumor protein includes an amino acid sequence encoded by a DNA molecule having a sequence selected from the group consisting of nucleotide sequences recited in SEQ ID NO: 2, 3, 8–29, 41–45, 47–52, 54–65, 70, 73–74, 79, 81, 87, 90, 92, 93, 97, 103, 104, 107, 109–111 and 115–160, the complements of said nucleotide sequences and variants thereof. As used herein, the term "polypeptide" encompasses amino acid chains of any length, including full length proteins, wherein the amino acid residues are linked by covalent peptide bonds. Thus, a polypeptide comprising a portion of one of the above prostate proteins may consist entirely of the portion, or the portion may be present within a larger polypeptide that contains additional sequences. The additional sequences may be derived from the native protein or may be heterologous, and such sequences may be immunoreactive and/or antigenic.

As used herein, an "immunogenic portion" of a human prostate tumor protein is a portion that is capable of eliciting an immune response in a patient inflicted with prostate cancer and as such binds to antibodies present within sera from a prostate cancer patient. Immunogenic portions of the proteins described herein may thus be identified in antibody binding assays. Such assays may generally be performed using any of a variety of means known to those of ordinary skill in the art, as described, for example, in Harlow and Lane, *Antibodies: A Laboratory Manual,* Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of prostate cancer patients.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. For prostate tumor polypeptides with immunoreactive properties, variants may, alternatively, be identified by modifying the amino acid sequence of one of the above polypeptides, and evaluating the immunoreactivity of the modified polypeptide. For prostate tumor polypeptides useful for the generation of diagnostic binding agents, a variant may be identified by evaluating a modified polypeptide for the ability to generate antibodies that detect the presence or absence of prostate cancer. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA,* 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. Such variant nucleotide sequences will generally hybridize to the recite nucleotide sequence under stringent conditions. As used herein, "stringent conditions" refers to prewashing in a solution of 6X SSC, 0.2% SDS; hybridizing at 65° C., 6X SSC, 0.2% SDS overnight; followed by two washes of 30 minutes each in 1X SSC, 0.1% SDS at 65° C. and two washes of 30 minutes each in 0.2X SSC, 0.1% SDS at 65° C.

"Polypeptides" as used herein also include combination, or fusion, polypeptides. A "combination polypeptide" is a polypeptide comprising at least one of the above immunogenic portions and one or more additional immunogenic prostate tumor-specific sequences, which are joined via a peptide linkage into a single amino acid chain. The sequences may be joined directly (i.e., with no intervening amino acids) or may be joined by way of a linked sequence (e.g., Gly-Cys-Gly) that does not significantly diminish the immunogenic properties of the component polypeptides.

The prostate tumor proteins of the present invention, and DNA molecules encoding such proteins, may be isolated from prostate tumor tissue using any of a variety of methods well known in the art. DNA sequences corresponding to a gene (of a portion thereof) encoding one of the inventive prostate tumor proteins may be isolated from a prostate tumor cDNA library using a subtraction technique as described in detail below. Examples of such DNA sequences are provided in SEQ ID NOS: 1–107, 109–111, 115–171, 173–175 and 177. Partial DNA sequences thus obtained may be used to design oligonucleotide primers for the amplification of full-length DNA sequences in a polymerase chain reaction (PCR), using techniques well known in the art (see, for example, Mullis et al., *Cold Spring Harbor Symp. Quant. Biol.,* 51:263, 1987; Erlich ed., *PCR Technology,* Stockton Press, N.Y., 1989). Once a DNA sequence encoding a polypeptide is obtained, any of the above modifications may be readily introduced using standard mutagenesis techniques, such as oligonucleotide-directed site-specific mutagenesis as taught, for example, by Adelman et al. (*DNA,* 2:183, 1983).

The prostate tumor polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

Alternatively, any of the above polypeptides may be produced recombinantly by inserting a DNA sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are $E.$ $coli,$ yeast or a mammalian cell line, such as CHO cells. The DNA sequences expressed in this manner may encode naturally occurring polypeptides, portions of naturally occurring polypeptides, or other variants thereof.

In general, regardless of the method of preparation, the polypeptides disclosed herein are prepared in substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known prostate antigen, together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Polypeptides of the present invention that comprise an immunogenic portion of a prostate tumor protein may generally be used for immunotherapy of prostate cancer, wherein the polypeptide stimulates the patient's own immune response to prostate tumor cells. In further aspects, the present invention provides methods for using one or more of the immunoreactive polypeptides encoded by a DNA molecule having a sequence provided in SEQ ID NOS: 1–107, 109–111, 115–171, 173–175 and 177 (or fusion proteins comprising one or more such polypeptides and/or DNA encoding such polypeptides) for immunotherapy of prostate cancer in a patient. As used herein, a "patient" refers to any warm-blooded animal, preferably a human. A patient may be afflicted with a disease, or may be free of detectable disease. Accordingly, the above immunoreactive polypeptides (or fusion proteins or DNA molecules encoding such polypeptides) may be used to treat prostate cancer or to inhibit the development of prostate cancer. The polypeptides may be administered either prior to or following surgical removal of primary tumors and/or treatment by administration of radiotherapy and conventional chemotherapeutic drugs.

In these aspects, the polypeptide or fusion protein is generally present within a pharmaceutical composition and/or a vaccine. Pharmaceutical compositions may comprise one or more polypeptides, each of which may contain one or more of the above sequences (or variants thereof), and a physiologically acceptable carrier. The vaccines may comprise one or more of such polypeptides and a non-specific immune response enhancer, such as an adjuvant, biodegradable microsphere (e.g., polylactic galactide) or a liposome (into which the polypeptide is incorporated). Pharmaceutical compositions and vaccines may also contain other epitopes of prostate tumor antigens, either incorporated into a combination polypeptide (i.e., a single polypeptide that contains multiple epitopes) or present within a separate polypeptide.

Alternatively, a pharmaceutical composition or vaccine may contain DNA encoding one or more of the above polypeptides, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as Bacillus-Calmette-Guerrin) that expresses an epitope of a prostate cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989;

Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against prostate tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in ex vivo treatment of prostate cancer. For example, cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

Polypeptides of the present invention may also, or alternatively, be used to generate binding agents, such as antibodies or fragments thereof, that are capable of detecting metastatic human prostate tumors. Binding agents of the present invention may generally be prepared using methods known to those of ordinary skill in the art, including the representative procedures described herein. Binding agents are capable of differentiating between patients with and without prostate cancer, using the representative assays described herein. In other words, antibodies or other binding agents raised against a prostate tumor protein, or a suitable portion thereof, will generate a signal indicating the presence of primary or metastatic prostate cancer in at least about 20% of patients afflicted with the disease, and will generate a negative signal indicating the absence of the disease in at least about 90% of individuals without primary or metastatic prostate cancer. Suitable portions of such prostate tumor proteins are portions that are able to generate a binding agent that indicates the presence of primary or metastatic prostate cancer in substantially all (i.e. at least about 80%, and preferably at least about 90%) of the patients for which prostate cancer would be indicated using the full length protein, and that indicate the absence of prostate cancer in substantially all of those samples that would be negative when tested with full length protein. The representative assays described below, such as the two-antibody sandwich assay, may generally be employed for evaluating the ability of a binding agent to detect metastatic human prostate tumors.

The ability of a polypeptide prepared as described herein to generate antibodies capable of detecting primary or metastatic human prostate tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic prostate cancer for the presence of a polypeptide that binds to the generated antibodies. Such test assays may be performed, for example, using a representative procedure described below. Polypeptides that generate antibodies capable of detecting at least 20% of primary or metastatic prostate tumors by such procedures are considered to be useful in assays for detecting primary or metastatic human prostate tumors. Polypeptide specific antibodies may be used alone or in combination to improve sensitivity.

Polypeptides capable of detecting primary or metastatic human prostate tumors may be used as markers for diagnosing prostate cancer or for monitoring disease progression in patients. In one embodiment, prostate cancer in a patient may be diagnosed by evaluating a biological sample obtained from the patient for the level of one or more of the above polypeptides, relative to a predetermined cut-off value. As used herein, suitable "biological samples" include blood, sera, urine and/or prostate secretions.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual,* Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g and preferably about 100 ng to about 1 $\mu$g, is sufficient to immobilize an adequate amount of binding agent.

Covalent attachment of binding agent to a solid support may generally be achieved by first reacting the support with a bifinctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., *Pierce Immunotechnology Catalog and Handbook,* 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of prostate cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without prostate cancer. In general, a sample generating a signal that is three standard deviations above the predetermined cut-off value is considered positive for prostate cancer. In an alternate preferred embodiment, the cut-off value is determined using a Receiver Operator Curve, according to the method of Sackett et al., Clinical Epidemiology: A Basic Science for Clinical Medicine, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for prostate cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of prostate cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of prostate cancer. In this embodiment, assays as described above for the diagnosis of prostate cancer may be performed over time, and the change in the level of reactive polypeptide(s) evaluated. For example, the assays may be performed every 24–72 hours for a period of 6 months to 1 year, and thereafter performed as needed. In general, prostate cancer is progressing in those patients in whom the level of polypeptide detected by the binding agent increases over time. In contrast, prostate cancer is not progressing when the level of reactive polypeptide either remains constant or decreases with time.

Antibodies for use in the above methods may be prepared by any of a variety of techniques known to those of ordinary skill in the art. See, e.g., Harlow and Lane, Antibodies: A Laboratory Manual, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, Eur. J. Immunol. 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate prostate tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g, U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify prostate tumor-specific cDNA derived from a biological sample, wherein at least one of the oligonucleotide primers is specific for a DNA molecule encoding a prostate tumor protein of the present invention. The presence of the amplified cDNA is then detected using techniques well known in the art, such as gel electrophoresis. Similarly, oligonucleotide probes specific for a DNA molecule encoding a prostate tumor protein of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule having a sequence selected from SEQ ID NOS: 1–107, 109–111, 115–171, 173–175 and 177. Preferably, oligonucleotide probes for use in the inventive diagnostic methods comprise at least about 15 contiguous oligonucleotides of a DNA molecule having a sequence provided in SEQ ID NOS: 1–107, 109–111, 115–171, 173–175 and 177. Techniques for both PCR based assays and hybridization assays are well known in the art (see, for example, Mullis et al. Ibid; Ehrlich, Ibid). Primers or probes may thus be used to detect prostate tumor-specific sequences in biological samples, including blood, semen, prostate tissue and/or prostate tumor tissue.

The following Examples are offered by way of illustration and not by way of limitation.

EXAMPLES

Example 1

ISOLATION AND CHARACTERIZATION OF PROSTATE TUMOR POLYPEPTIDES

This Example describes the isolation of prostate tumor polypeptides from a prostate tumor cDNA library.

A human prostate tumor cDNA expression library was constructed from prostate tumor poly A+ RNA using a Superscript Plasmid System for cDNA Synthesis and Plasmid Cloning kit (BRL Life Technologies, Gaithersburg, Md. 20897) following the manufacturer's protocol. Specifically, prostate tumor tissues were homogenized with polytron (Kinematica, Switzerland) and total RNA was extracted using Trizol reagent (BRL Life Technologies) as directed by the manufacturer. The poly A+ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BAXI adaptors (Invitrogen, San Diego, Calif.) and digested with NotI. Following size fractionation with Chroma Spin-1000 columns (Clontech, Palo Alto, Calif. 94303), the cDNA was ligated into the EcoRI/NotI site of pCDNA3.1 (Invitrogen) and transformed into ElectroMax $E.$ $coli$ DH10B cells (BRL Life Technologies) by electroporation.

Using the same procedure, a normal human pancreas cDNA expression library was prepared from a pool of six tissue specimens (Clontech). The cDNA libraries were characterized by determining the number of independent colonies, the percentage of clones that carried insert, the average insert size and by sequence analysis. The prostate tumor library contained $1.64 \times 10^7$ independent colonies, with 70% of clones having an insert and the average insert size being 1745 base pairs. The normal pancreas cDNA library contained $3.3 \times 10^6$ independent colonies, with 69% of clones having inserts and the average insert size being 1120 base pairs. For both libraries, sequence analysis showed that the majority of clones had a full length cDNA sequence and were synthesized from mRNA, with minimal rRNA and mitochondrial DNA contamination.

cDNA library subtraction was performed using the above prostate tumor and normal pancreas cDNA libraries, as described by Hara et al. (*Blood,* 84:189–199, 1994) with some modifications. Specifically, a prostate tumor-specific subtracted cDNA library was generated as follows. Normal pancreas cDNA library (70 µg) was digested with EcoRI, NotI, and SfuI, followed by a filling-in reaction with DNA polymerase Klenow fragment. After phenol-chloroform extraction and ethanol precipitation, the DNA was dissolved in 100 µl of $H_2O$, heat-denatured and mixed with 100 µl (100 µg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (50 µl) was added and the biotinylation reaction was repeated. After extraction with butanol five times, the DNA was ethanol-precipitated and dissolved in 23 µl $H_2O$ to form the driver DNA.

To form the tracer DNA, 10 µg prostate tumor cDNA library was digested with BamHI and XhoI, phenol chloroform extracted and passed through Chroma spin-400 columns (Clontech). Following ethanol precipitation, the tracer DNA was dissolved in 5 µl $H_2O$. Tracer DNA was mixed with 15 µl driver DNA and 20 µl of 2x hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 µl $H_2O$, mixed with 8 µl driver DNA and 20 µl of 2x hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK+ (Stratagene, La Jolla, Calif. 92037) and transformed into ElectroMax $E.$ $coli$ DH10B cells by electroporation to generate a prostate tumor specific subtracted cDNA library (prostate subtraction 1).

To analyze the subtracted CDNA library, plasmid DNA was prepared from 100 independent clones, randomly picked from the subtracted prostate tumor specific library and grouped based on insert size. Representative cDNA clones were further characterized by DNA sequencing with a Perkin Elmer/Applied Biosystems Division Automated Sequencer Model 373A (Foster City, Calif.). Six CDNA clones, hereinafter referred to as F1-13, F1-12, F1-16, H1-1, H1-9 and H1-4, were shown to be abundant in the subtracted prostate-specific cDNA library. The determined 3' and 5' CDNA sequences for F1-12 are provided in SEQ ID NO: 2 and 3, respectively, with determined 3' cDNA sequences for F1-13, F1-16, H1-1, H1-9 and H1-4 being provided in SEQ ID NO: 1 and 4–7, respectively.

The cDNA sequences for the isolated clones were compared to known sequences in the gene bank using the EMBL and GenBank databases (release 96). Four of the prostate tumor cDNA clones, F1-13, F1-16, H1-1, and H1-4, were determined to encode the following previously identified proteins: prostate specific antigen (PSA), human glandular kallikrein, human tumor expression enhanced gene, and mitochondria cytochrome C oxidase subunit II. H1-9 was found to be identical to a previously identified human autonomously replicating sequence. No significant homologies to the cDNA sequence for F1-12 were found.

Subsequent studies led to the isolation of a full-length cDNA sequence for F1-12. This sequence is provided in SEQ ID NO: 107, with the corresponding predicted amino acid sequence being provided in SEQ ID NO: 108.

To clone less abundant prostate tumor specific genes, cDNA library subtraction was performed by subtracting the prostate tumor cDNA library described above with the normal pancreas cDNA library and with the three most abundant genes in the previously subtracted prostate tumor specific cDNA library: human glandular kallikrein, prostate specific antigen (PSA), and mitochondria cytochrome C oxidase subunit II. Specifically, 1 µg each of human glandular kallikrein, PSA and mitochondria cytochrome C oxidase subunit II cDNAs in pCDNA3.1 were added to the driver DNA and subtraction was performed as described above to provide a second subtracted cDNA library hereinafter referred to as the "subtracted prostate tumor specific cDNA library with spike".

Twenty-two cDNA clones were isolated from the subtracted prostate tumor specific cDNA library with spike. The determined 3' and 5' cDNA sequences for the clones referred to as J1-17, L1-12, N1-1862, J1-13, J1-19, J1-25, J1-24, K1-58, K1-63, L1-4 and L1-14 are provided in SEQ ID NOS: 8–9, 10–11, 12–13, 14–15, 16–17, 18–19, 20–21, 22–23, 24–25, 26–27 and 28–29, respectively. The determined 3' cDNA sequences for the clones referred to as J1-12, J1-16, J1-21, K1-48, K1-55, L1-2, L1-6, N1-1858, N1-1860, N1-1861, N1-1864 are provided in SEQ ID NOS: 30–40, respectively. Comparison of these sequences with those in the gene bank as described above, revealed no significant homologies to three of the five most abundant DNA species, (J1-17, L1-12 and N1-1862; SEQ ID NOS: 8–9, 10–11 and 12–13, respectively). Of the remaining two most abundant species, one (J1-12; SEQ ID NO:30) was found to be identical to the previously identified human pulmonary surfactant-associated protein, and the other (K1-48; SEQ ID NO:33) was determined to have some homology to *R. norvegicus* mRNA for 2-arylpropionyl-CoA epimerase. Of the 17 less abundant cDNA clones isolated from the subtracted prostate tumor specific cDNA library with spike, four (J1-16, K1-55, L1-6 and N1-1864; SEQ ID NOS:31, 34, 36 and 40, respectively) were found to be identical to previously identified sequences, two (J1-21 and N1-1860; SEQ ID NOS: 32 and 38, respectively) were found to show some homology to non-human sequences, and two (L1-2 and N1-1861; SEQ ID NOS: 35 and 39, respectively) were found to show some homology to known human sequences. No significant homologies were found to the polypeptides J1-13, J1-19, J1-24, J1-25, K1-58, K1-63, L1-4, L1-14 (SEQ ID NOS: 14–15, 16–17, 20–21, 18–19, 22–23, 24–25, 26–27, 28–29, respectively).

Subsequent studies led to the isolation of full length cDNA sequences for J1-17, L1-12 and N1-1862 (SEQ ID NOS: 109–111, respectively). The corresponding predicted amino acid sequences are provided in SEQ ID NOS: 112–114.

In a further experiment, four additional clones were identified by subtracting a prostate tumor cDNA library with normal prostate cDNA prepared from a pool of three normal prostate poly A+ RNA (prostate subtraction 2). The determined cDNA sequences for these clones, hereinafter referred to as U1-3064, U1-3065, V1-3692 and 1A-3905, are provided in SEQ ID NO: 69–72, respectively. Comparison of the determined sequences with those in the gene bank revealed no significant homologies to U1-3065.

A second subtraction with spike (prostate subtraction spike 2) was performed by subtracting a prostate tumor specific cDNA library with spike with normal pancreas cDNA library and further spiked with PSA, J1-17, pulmonary surfactant-associated protein, mitochondrial DNA, cytochrome c oxidase subunit II, N1-1862, autonomously replicating sequence, L1-12 and tumor expression enhanced gene. Four additional clones, hereinafter referred to as V1-3686, R1-2330, 1B-3976 and V1-3679, were isolated. The determined cDNA sequences for these clones are provided in SEQ ID NO:73–76, respectively. Comparison of these sequences with those in the gene bank revealed no significant homologies to V1-3686 and R1-2330.

Further analysis of the three prostate subtractions described above (prostate subtraction 2, subtracted prostate tumor specific cDNA library with spike, and prostate subtraction spike 2) resulted in the identification of sixteen additional clones, referred to as 1G-4736, 1G-4738, 1G-4741, 1G-4744, 1G-4734, 1H-4774, 1H4781, 1H-4785, 1H-4787, 1H-4796, 1I-4810, 1I-4811, 1J-4876, 1K-4884 and 1K-4896. The determined cDNA sequences for these clones are provided in SEQ ID NOS: 77–92, respectively.

Comparison of these sequences with those in the gene bank as described above, revealed no significant homologies to 1G-4741, 1G-4734, 1I-4807, 1J-4876 and 1K-4896 (SEQ ID NOS: 79, 81, 87, 90 and 92, respectively).

An additional subtraction was performed by subtracting a normal prostate cDNA library with normal pancreas cDNA (prostate subtraction 3). This led to the identification of six additional clones referred to as 1G-4761, 1G-4762, 1H-4766, 1H-4770, 1H-4771 and 1H-4772 (SEQ ID NOS: 93–98). Comparison of these sequences with those in the gene bank revealed no significant homologies to 1G-4761 and 1H-4771 (SEQ ID NOS: 93 and 97, respectively).

Subtraction of a prostate tumor cDNA library, prepared from a pool of polyA+ RNA from three prostate cancer patients, with a normal pancreas cDNA library (prostate subtraction 4) led to the identification of eight clones, referred to as 1D-4297, 1D-4309, 1D.1-4278, 1D-4288, 1D-4283, 1D-4304, 1D-4296 and 1D-4280 (SEQ ID NOS: 99–107). These sequences were compared to those in the gene bank as described above. No significant homologies were found to 1D-4283 and 1D-4304 (SEQ ID NOS: 103 and 104, respectively).

Example 2

DETERMINATION OF TISSUE SPECIFICITY OF PROSTATE TUMOR POLYPEPTIDES

Using gene specific primers, mRNA expression levels for the representative prostate tumor polypeptides F1-16, H1-1, J1-17, L1-12, F1-12 and N1-1862 were examined in a variety of normal and tumor tissues using RT-PCR.

Briefly, total RNA was extracted from a variety of normal and tumor tissues using Trizol reagent as described above. First strand synthesis was carried out using 1–2 $\mu$g of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. First, serial dilutions of the first strand cDNAs were prepared and RT-PCR assays were performed using β-actin specific primers. A dilution was then chosen that enabled the linear range amplification of the β-actin template and which was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in four different types of tumor tissue (prostate tumor from 2 patients, breast tumor from 3 patients, colon tumor, lung tumor), and sixteen different normal tissues, including prostate, colon, kidney, liver, lung, ovary, pancreas, skeletal muscle, skin, stomach, testes, bone marrow and brain. F1-16 was found to be expressed at high levels in prostate tumor tissue, colon tumor and normal prostate, and at lower levels in normal liver, skin and testes, with expression being undetectable in the other tissues examined. H1-1 was found to be expressed at high levels in prostate tumor, lung tumor, breast tumor, normal prostate, normal colon and normal brain, at much lower levels in normal lung, pancreas, skeletal muscle, skin, small intestine, bone marrow, and was not detected in the other tissues tested. J1-17 and L1-12 appear to be specifically over-expressed in prostate, with both genes being expressed at high levels in prostate tumor and normal prostate but at low to undetectable levels in all the other tissues examined. N1-1862 was found to be over-expressed in 60% of prostate tumors and detectable in normal colon and kidney. The RT-PCR results thus indicate that F1-16, H1-1, J1-17, N1-1862 and L1-12 are either prostate specific or are expressed at significantly elevated levels in prostate.

Further RT-PCR studies showed that F1-12 is over-expressed in 60% of prostate tumors, detectable in normal kidney but not detectable in all other tissues tested. Similarly, R1-2330 was shown to be over-expressed in 40% of prostate tumors, detectable in normal kidney and liver, but not detectable in all other tissues tested. U1-3064 was found to be over-expressed in 60% of prostate tumors, and also expressed in breast and colon tumors, but was not detectable in normal tissues.

RT-PCR characterization of R1-2330, U1-3064 and 1D-4279 showed that these three antigens are overexpressed in prostate and/or prostate tumors.

Example 3

ISOLATION AND CHARACTERIZATION OF PROSTATE TUMOR POLYPEPTIDES BY PCR-BASED SUBTRACTION

A cDNA subtraction library, containing cDNA from normal prostate subtracted with ten other normal tissue cDNAs (brain, heart, kidney, liver, lung, ovary, placenta, skeletal muscle, spleen and thymus) and then submitted to a first round of PCR amplification, was purchased from Clontech. This library was subjected to a second round of PCR amplification, following the manufacturer's protocol. The resulting cDNA fragments were subcloned into the vector pT7 Blue T-vector (Novagen, Madison, Wis.) and transformed into XL-1 Blue MRF' E. coli (Stratagene). DNA was isolated from independent clones and sequenced using a Perkin Elmer/Applied Biosystems Division Automated Sequencer Model 373A.

Fifty-nine positive clones were sequenced. Comparison of the DNA sequences of these clones with those in the gene bank, as described above, revealed no significant homologies to 25 of these clones, hereinafter referred to as P5, P8, P9, P18, P20, P30, P34, P36, P38, P39, P42, P49, P50, P53, P55, P60, P64, P65, P73, P75, P76, P79 and P84. The determined cDNA sequences for these clones are provided in SEQ ID NO:41–45, 47–52 and 54–65, respectively. P29, P47, P68, P80 and P82 (SEQ ID NO:46, 53 and 66–68, respectively) were found to show some degree of homology to previously identified DNA sequences. To the best of the inventors' knowledge, none of these sequences have been previously shown to be present in prostate.

Further studies using the PCR-based methodology described above resulted in the isolation of more than 180 additional clones, of which 23 clones were found to show no significant homologies to known sequences. The determined cDNA sequences for these clones are provided in SEQ ID NO: 115–123, 127, 131, 137, 145, 147–151, 153, 156–158 and 160. Twenty-three clones (SEQ ID NO: 124–126, 128–130, 132–136, 138–144, 146, 152, 154, 155 and 159) were found to show some homology to previously identified ESTs. An additional ten clones (SEQ ID NO: 161–170) were found to have some degree of homology to known genes. An additional clone, referred to as P703, was found to have five splice variants. The determined DNA sequence for the variants referred to as DE1, DE13 and DE14 are provided in SEQ ID NOS: 171, 175 and 177, respectively, with the corresponding predicted amino acid sequences being provided in SEQ ID NO: 172, 176 and 178, respectively. The DNA sequences for the splice variants referred to as DE2 and DE6 are provided in SEQ ID NOS: 173 and 174, respectively.

mRNA Expression levels for representative clones in tumor tissues (prostate (n=5), breast (n=2), colon and lung) normal tissues (prostate (n=5), colon, kidney, liver, lung (n=2), ovary (n=2), skeletal muscle, skin, stomach, small intestine and brain), and activated and non-activated PBMC was determined by RT-PCT as described above. Expression was examined in one sample of each tissue type unless otherwise indicated.

P9 was found to be highly expressed in normal prostate and prostate tumor compared to all normal tissues tested except for normal colon which showed comparable expression. P20 was found to be highly expressed in normal prostate and prostate tumor, compared to all twelve normal tissues tested. A modest increase in expression of P20 in breast tumor (n=2), colon tumor and lung tumor was seen compared to all normal tissues except lung (1 of 2). Increased expression of P18 was found in normal prostate, prostate tumor and breast tumor compared to other normal tissues except lung and stomach. A modest increase in expression of P5 was observed in normal prostate compared to most other normal tissues. However, some elevated expression was seen in normal lung and PBMC. Elevated expression of P5 was also observed in prostate tumors (2 of 5), breast tumor and one lung tumor sample. For P30, similar expression levels were seen in normal prostate and prostate tumor, compared to six of twelve other normal tissues tested. Increased expression was seen in breast tumors, one lung tumor sample and one colon tumor sample, and also in normal PBMC. P29 was found to be over-expressed in prostate tumor (5 of 5) and normal prostate (5 of 5) compared to the majority of normal tissues. However, substantial expression of P29 was observed in normal colon and normal lung (2 of 2). P80 was found to be over-expressed in prostate tumor (5 of 5) and normal prostate (5 of 5) compared to all other normal tissues tested, with increased expression also being seen in colon tumor.

Example 4

SYNTHESIS OF POLYPEPTIDES

Polypeptides may be synthesized on a Perkin Elmer/Applied Biosystems 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed:

1. An isolated polypeptide comprising an amino acid sequence of SEQ ID NO: 113.

2. A composition comprising the polypeptide of claim 1 and a physiologically acceptable carrier.

3. The composition of claim 2, wherein the physiologically acceptable carrier is selected from the group consisting of: water; saline; alcohol; lipids; waxes; buffers and microspheres.

4. A composition comprising the polypeptide of claim 1 and a non-specific immune response enhancer.

5. The composition of claim 4, wherein the non-specific immune response enhancer is selected from the group consisting of: adjuvants; microspheres and liposomes.

6. The composition of claim 5, wherein the adjuvant comprises a component selected from the group consisting of: aluminum hydroxide; mineral oil; lipid A; *Bordella pertussis* and *Mycobacterium tuberculosis*.

7. The composition of claim 5, wherein the adjuvant is selected from the group consisting of: Freund's Incomplete Adjuvant; Freund's Complete Adjuvant and Merck Adjuvant 65.

8. A fusion protein comprising a polypeptide according to claim 1 and a known prostate antigen.

9. A fusion protein comprising at least one polypeptide according to claim 1.

10. A composition comprising a fusion protein according to any one of claims 8 and 9, and a physiologically acceptable carrier.

11. A composition comprising a fusion protein according to any one of claims 8 and 9, and a non-specific immune response enhancer.

12. The composition of claim 11 wherein the non-specific immune response enhancer is an adjuvant.

13. A method for stimulating an immune response in a patient, comprising administering to the patient a polypeptide of claim 1.

14. A method for stimulating an immune response in a patient comprising administering a composition selected from the group consisting of:

(a) compositions comprising a polypeptide according to claim 1; and (b) compositions comprising a fusion protein according to claim 9.

\* \* \* \* \*

UNITED STATES PATENT AND TRADEMARK OFFICE
CERTIFICATE OF CORRECTION

PATENT NO.    : 6,261,562 B1  
DATED         : July 17, 2001  
INVENTOR(S)   : Jiangchun Xu and Davin C. Dillon It is certified that error appears in the above-identified patent and that said Letters Patent is hereby corrected as shown below:

Column 175,
Lines 43 and 44, "Incomplete Adjuvant; Freund's" should read -- Incomplete Adjuvant and Freund's --.

Signed and Sealed this

Sixth Day of August, 2002

Attest:

Attesting Officer

JAMES E. ROGAN
Director of the United States Patent and Trademark Office

UNITED STATES PATENT AND TRADEMARK OFFICE
Certificate

Patent No. 6,261,562 B1                                                        Patented: July 17, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jiangchun Xu, Bellevue, WA (US); XinQun Zhang, Mercer Island, WA (US); and John A. Stolk, Bothell, WA (US).

Signed and Sealed this Twenty-fourth Day of July 2007.

WILLIAM R. DIXON
*Special Program Examiner*
Technology Center 1600

SEQUENCE LISTING (1) GENERAL INFORMATION:

(iii) NUMBER OF SEQUENCES: 178

(2) INFORMATION FOR SEQ ID NO: 1:

(i) SEQUENCE CHARACTERISTICS:
        (A) LENGTH: 814 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

```
TTTTTTTTTT TTTTTCACAG TATAACAGCT CTTTATTTCT GTGAGTTCTA CTAGGAAATC      60
ATCAAATCTG AGGGTTGTCT GGAGGACTTC AATACACCTC CCCCCATAGT GAATCAGCTT     120
CCAGGGGGTC CAGTCCCTCT CCTTACTTCA TCCCCATCCC ATGCCAAAGG AAGACCCTCC     180
CTCCTTGGCT CACAGCCTTC TCTAGGCTTC CCAGTGCCTC CAGGACAGAG TGGGTTATGT     240
TTTCAGCTCC ATCCTTGCTG TGAGTGTCTG GTGCGTTGTG CCTCCAGCTT CTGCTCAGTG     300
CTTCATGGAC AGTGTCCAGC ACATGTCACT CTCCACTCTC TCAGTGTGGA TCCACTAGTT     360
CTAGAGCGGC CGCCACCGCG GTGGAGCTCC AGCTTTTGTT CCCTTTAGTG AGGGTTAATT     420
GCGCGCTTGG CGTAATCATG GTCATAACTG TTTCCTGTGT GAAATTGTTA TCCGCTCACA     480
ATTCCACACA ACATACGAGC CGGAAGCATA AAGTGTAAAG CCTGGGGTGC CTAATGAGTG     540
ANCTAACTCA CATTAATTGC GTTGCGCTCA CTGNCCGCTT TCCAGTCNGG AAAACTGTCG     600
TGCCAGCTGC ATTAATGAAT CGGCCAACGC NCGGGGAAAA GCGGTTTGCG TTTTGGGGGC     660
TCTTCCGCTT CTCGCTCACT NANTCCTGCG CTCGGTCNTT CGGCTGCGGG GAACGGTATC     720
ACTCCTCAAA GGNGGTATTA CGGTTATCCN NAAATCNGGG GATACCCNGG AAAAAANTTT     780
AACAAAAGGG CANCAAAGGG CNGAAACGTA AAAA                                  814
```

(2) INFORMATION FOR SEQ ID NO: 2:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

```
ACAGAAATGT TGGATGGTGG AGCACCTTTC TATACGACTT ACAGGACAGC AGATGGGGAA      60
TTCATGGCTG TTGGAGCAAT AGAACCCCAG TTCTACGAGC TGCTGATCAA AGGACTTGGA     120
CTAAAGTCTG ATGAACTTCC CAATCAGATG AGCATGGATG ATTGGCCAGA AATGAAGAAG     180
AAGTTTGCAG ATGTATTTGC AAAGAAGACG AAGGCAGAGT GGTGTCAAAT CTTTGACGGC     240
ACAGATGCCT GTGTGACTCC GGTTCTGACT TTTGAGGAGG TTGTTCATCA TGATCACAAC     300
AAGGAACGGG GCTCGTTTAT CACCAGTGAG GAGCAGGACG TGAGCCCCCG CCCTGCACCT     360
CTGCTGTTAA ACACCCCAGC CATCCCTTCT TTCAAAAGGG ATCCACTAGT TCTAGAAGCG     420
GCCGCCACCG CGGTGGAGCT CCAGCTTTTG TTCCCTTTAG TGAGGGTTAA TTGCGCGCTT     480
GGCGTAATCA TGGTCATAGC TGTTTCCTGT GTGAAATTGT TATCCGCTCA CAATTCCCCC     540
```

| | |
|---|---|
| AACATACGAG CCGGAACATA AAGTGTTAAG CCTGGGGTGC CTAATGANTG AGCTAACTCN | 600 |
| CATTAATTGC GTTGCGCTCA CTGCCCGCTT TCCAGTCGGG AAAACTGTCG TGCCACTGCN | 660 |
| TTANTGAATC NGCCACCCCC CGGGAAAAGG CGGTTGCNTT TTGGGCCTCT TCCGCTTTCC | 720 |
| TCGCTCATTG ATCCTNGCNC CCGGTCTTCG GCTGCGGNGA ACGGTTCACT CCTCAAAGGC | 780 |
| GGTNTNCCGG TTATCCCCAA ACNGGGGATA CCCNGA | 816 |

(2) INFORMATION FOR SEQ ID NO: 3:

(i) SEQUENCE CHARACTERISTICS:
        (A) LENGTH: 773 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

| | |
|---|---|
| CTTTTGAAAG AAGGGATGGC TGGGGTGTTT AACAGCAGAG GTGCAGGGCG GGGGCTCACG | 60 |
| TCCTGCTCCT CACTGGTGAT AAACGAGCCC CGTTCCTTGT TGTGATCATG ATGAACAACC | 120 |
| TCCTCAAAAG TCAGAACCGG AGTCACACAG GCATCTGTGC CGTCAAAGAT TTGACACCAC | 180 |
| TCTGCCTTCG TCTTCTTTGC AAATACATCT GCAAACTTCT TCTTCATTTC TGGCCAATCA | 240 |
| TCCATGCTCA TCTGATTGGG AAGTTCATCA GACTTTAGTC CANNTCCTTT GATCAGCAGC | 300 |
| TCGTAGAACT GGGGTTCTAT TGCTCCAACA GCCATGAATT CCCCATCTGC TGTCCTGTAA | 360 |
| GTCGTATAGA AAGGTGCTCC ACCATCCAAC ATGTTCTGTC CTCGAGGGGG GGCCCGGTAC | 420 |
| CCAATTCGCC CTATANTGAG TCGTATTACG CGCGCTCACT GGCCGTCGTT TTACAACGTC | 480 |
| GTGACTGGGA AAACCCTGGG CGTTACCAAC TTAATCGCCT TGCAGCACAT CCCCCTTTCG | 540 |
| CCAGCTGGGC GTAATANCGA AAAGGCCCGC ACCGATCGCC CTTCCAACAG TTGCGCACCT | 600 |
| GAATGGGNAA ATGGGACCCC CCTGTTACCG CGCATTNAAC CCCCGCNGGG TTTNGTTGTT | 660 |
| ACCCCCACNT NNACCGCTTA CACTTTGCCA GCGCCTTANC GCCCGCTCCC TTTCNCCTTT | 720 |
| CTTCCCTTCC TTTCNCNCCN CTTTCCCCCG GGGTTTCCCC CNTCAAACCC CNA | 773 |

(2) INFORMATION FOR SEQ ID NO: 4:

(i) SEQUENCE CHARACTERISTICS:
        (A) LENGTH: 828 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

| | |
|---|---|
| CCTCCTGAGT CCTACTGACC TGTGCTTTCT GGTGTGGAGT CCAGGGCTGC TAGGAAAAGG | 60 |
| AATGGGCAGA CACAGGTGTA TGCCAATGTT TCTGAAATGG GTATAATTTC GTCCTCTCCT | 120 |
| TCGGAACACT GGCTGTCTCT GAAGACTTCT CGCTCAGTTT CAGTGAGGAC ACACACAAAG | 180 |
| ACGTGGGTGA CCATGTTGTT TGTGGGGTGC AGAGATGGGA GGGGTGGGGC CCACCCTGGA | 240 |
| AGAGTGGACA GTGACACAAG GTGGACACTC TCTACAGATC ACTGAGGATA AGCTGGAGCC | 300 |
| ACAATGCATG AGGCACACAC ACAGCAAGGA TGACNCTGTA AACATAGCCC ACGCTGTCCT | 360 |
| GNGGGCACTG GGAAGCCTAN ATNAGGCCGT GAGCANAAAG AAGGGGAGGA TCCACTAGTT | 420 |
| CTANAGCGGC CGCCACCGCG GTGGANCTCC ANCTTTTGTT CCCTTTAGTG AGGGTTAATT | 480 |
| GCGCGCTTGG CNTAATCATG GTCATANCTN TTTCCTGTGT GAAATTGTTA TCCGCTCACA | 540 |

| ATTCCACACA ACATACGANC CGGAAACATA AANTGTAAAC CTGGGGTGCC TAATGANTGA | 600 |
| CTAACTCACA TTAATTGCGT TGCGCTCACT GCCCGCTTTC CAATCNGGAA ACCTGTCTTG | 660 |
| CCNCTTGCAT TNATGAATCN GCCAACCCCC GGGGAAAAGC GTTTGCGTTT TGGGCGCTCT | 720 |
| TCCGCTTCCT CNCTCANTTA NTCCCTNCNC TCGGTCATTC CGGCTGCNGC AAACCGGTTC | 780 |
| ACCNCCTCCA AAGGGGGTAT TCCGGTTTCC CCNAATCCGG GGANANCC | 828 |

(2) INFORMATION FOR SEQ ID NO: 5:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

| TTTTTTTTTT TTTTTACTGA TAGATGGAAT TTATTAAGCT TTTCACATGT GATAGCACAT | 60 |
| AGTTTTAATT GCATCCAAAG TACTAACAAA AACTCTAGCA ATCAAGAATG GCAGCATGTT | 120 |
| ATTTTATAAC AATCAACACC TGTGGCTTTT AAAATTTGGT TTTCATAAGA TAATTTATAC | 180 |
| TGAAGTAAAT CTAGCCATGC TTTTAAAAAA TGCTTTAGGT CACTCCAAGC TTGGCAGTTA | 240 |
| ACATTTGGCA TAAACAATAA TAAAACAATC ACAATTTAAT AAATAACAAA TACAACATTG | 300 |
| TAGGCCATAA TCATATACAG TATAAGGAAA AGGTGGTAGT GTTGAGTAAG CAGTTATTAG | 360 |
| AATAGAATAC CTTGGCCTCT ATGCAAATAT GTCTAGACAC TTTGATTCAC TCAGCCCTGA | 420 |
| CATTCAGTTT TCAAAGTAGG AGACAGGTTC TACAGTATCA TTTTACAGTT TCCAACACAT | 480 |
| TGAAAACAAG TAGAAAATGA TGAGTTGATT TTTATTAATG CATTACATCC TCAAGAGTTA | 540 |
| TCACCAACCC CTCAGTTATA AAAAATTTTC AAGTTATATT AGTCATATAA CTTGGTGTGC | 600 |
| TTATTTAAA TTAGTGCTAA ATGGATTAAG TGAAGACAAC AATGGTCCCC TAATGTGATT | 660 |
| GATATTGGTC ATTTTTACCA GCTTCTAAAT CTNAACTTTC AGGCTTTTGA ACTGGAACAT | 720 |
| TGNATNACAG TGTTCCANAG TTNCAACCTA CTGGAACATT ACAGTGTGCT TGATTCAAAA | 780 |
| TGTTATTTTG TTAAAAATTA AATTTTAACC TGGTGGAAAA ATAATTTGAA ATNA | 834 |

(2) INFORMATION FOR SEQ ID NO: 6:

(i) SEQUENCE CHARACTERISTICS:
        (A) LENGTH: 818 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

| TTTTTTTTTT TTTTTTTTTT AAGACCCTCA TCAATAGATG GAGACATACA GAAATAGTCA | 60 |
| AACCACATCT ACAAAATGCC AGTATCAGGC GGCGGCTTCG AAGCCAAAGT GATGTTTGGA | 120 |
| TGTAAAGTGA ATATTAGTT GGCGGATGAA GCAGATAGTG AGGAAAGTTG AGCCAATAAT | 180 |
| GACGTGAAGT CCGTGGAAGC CTGTGGCTAC AAAAAATGTT GAGCCGTAGA TGCCGTCGGA | 240 |
| AATGGTGAAG GGAGACTCGA AGTACTCTGA GGCTTGTAGG AGGGTAAAAT AGAGACCCAG | 300 |
| TAAAATTGTA ATAAGCAGTG CTTGAATTAT TTGGTTTCGG TTGTTTTCTA TTAGACTATG | 360 |
| GTGAGCTCAG GTGATTGATA CTCCTGATGC GAGTAATACG GATGTGTTTA GGAGTGGGAC | 420 |

-continued

| | | |
|---|---|---|
| TTCTAGGGGA TTTAGCGGGG TGATGCCTGT TGGGGGCCAG TGCCCTCCTA GTTGGGGGGT | 480 | |
| AGGGGCTAGG CTGGAGTGGT AAAAGGCTCA GAAAAATCCT GCGAAGAAAA AAACTTCTGA | 540 | |
| GGTAATAAAT AGGATTATCC CGTATCGAAG GCCTTTTTGG ACAGGTGGTG TGTGGTGGCC | 600 | |
| TTGGTATGTG CTTTCTCGTG TTACATCGCG CCATCATTGG TATATGGTTA GTGTGTTGGG | 660 | |
| TTANTANGGC CTANTATGAA GAACTTTTGG ANTGGAATTA AATCAATNGC TTGGCCGGAA | 720 | |
| GTCATTANGA NGGCTNAAAA GGCCCTGTTA NGGGTCTGGG CTNGGTTTTA CCCNACCCAT | 780 | |
| GGAATNCNCC CCCCGGACNA NTGNATCCCT ATTCTTAA | 818 | |

(2) INFORMATION FOR SEQ ID NO: 7:

(i) SEQUENCE CHARACTERISTICS:
        (A) LENGTH: 817 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

| | | |
|---|---|---|
| TTTTTTTTTT TTTTTTTTTT TGGCTCTAGA GGGGGTAGAG GGGGTGCTAT AGGGTAAATA | 60 | |
| CGGGCCCTAT TTCAAAGATT TTTAGGGGAA TTAATTCTAG GACGATGGGT ATGAAACTGT | 120 | |
| GGTTTGCTCC ACAGATTTCA GAGCATTGAC CGTAGTATAC CCCCGGTCGT GTAGCGGTGA | 180 | |
| AAGTGGTTTG GTTTAGACGT CCGGGAATTG CATCTGTTTT TAAGCCTAAT GTGGGGACAG | 240 | |
| CTCATGAGTG CAAGACGTCT TGTGATGTAA TTATTATACN AATGGGGCT TCAATCGGGA | 300 | |
| GTACTACTCG ATTGTCAACG TCAAGGAGTC GCAGGTCGCC TGGTTCTAGG AATAATGGGG | 360 | |
| GAAGTATGTA GGAATTGAAG ATTAATCCGC CGTAGTCGGT GTTCTCCTAG GTTCAATACC | 420 | |
| ATTGGTGGCC AATTGATTTG ATGGTAAGGG GAGGGATCGT TGAACTCGTC TGTTATGTAA | 480 | |
| AGGATNCCTT NGGGATGGGA AGGCNATNAA GGACTANGGA TNAATGGCGG GCANGATATT | 540 | |
| TCAAACNGTC TCTANTTCCT GAAACGTCTG AAATGTTAAT AANAATTAAN TTTNGTTATT | 600 | |
| GAATNTTNNG GAAAAGGGCT TACAGGACTA GAAACCAAAT ANGAAANTA ATNNTAANGG | 660 | |
| CNTTATCNTN AAAGGTNATA ACCNCTCCTA TNATCCCACC CAATNGNATT CCCCACNCNN | 720 | |
| ACNATTGGAT NCCCANTTC CANAAANGGC CNCCCCCGG TGNANNCCNC CTTTTGTTCC | 780 | |
| CTTNANTGAN GGTTATTCNC CCCTNGCNTT ATCANCC | 817 | |

(2) INFORMATION FOR SEQ ID NO: 8:

(i) SEQUENCE CHARACTERISTICS:
        (A) LENGTH: 799 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

| | | |
|---|---|---|
| CATTTCCGGG TTTACTTTCT AAGGAAAGCC GAGCGGAAGC TGCTAACGTG GGAATCGGTG | 60 | |
| CATAAGGAGA ACTTTCTGCT GGCACGCGCT AGGGACAAGC GGGAGAGCGA CTCCGAGCGT | 120 | |
| CTGAAGCGCA CGTCCCAGAA GGTGGACTTG GCACTGAAAC AGCTGGGACA CATCCGCGAG | 180 | |
| TACGAACAGC GCCTGAAAGT GCTGGAGCGG GAGGTCCAGC AGTGTAGCCG CGTCCTGGGG | 240 | |
| TGGGTGGCCG ANGCCTGANC CGCTCTGCCT TGCTGCCCCC ANGTGGGCCG CCACCCCCTG | 300 | |
| ACCTGCCTGG GTCCAAACAC TGAGCCCTGC TGGCGGACTT CAAGGANAAC CCCCACANGG | 360 | |

```
GGATTTTGCT CCTANANTAA GGCTCATCTG GGCCTCGGCC CCCCCACCTG GTTGGCCTTG      420

TCTTTGANGT GAGCCCCATG TCCATCTGGG CCACTGTCNG GACCACCTTT NGGGAGTGTT      480

CTCCTTACAA CCACANNATG CCCGGCTCCT CCCGGAAACC ANTCCCANCC TGNGAAGGAT      540

CAAGNCCTGN ATCCACTNNT NCTANAACCG GCCNCCNCCG CNGTGGAACC CNCCTTNTGT      600

TCCTTTTCNT TNAGGGTTAA TNNCGCCTTG GCCTTNCCAN NGTCCTNCNC NTTTTCCNNT      660

GTTNAAATTG TTANGCNCCC NCCNNTCCCN CNNCNNCNAN CCCGACCCNN ANNTTNNANN      720

NCCTGGGGGT NCCNNCNGAT TGACCCNNCC NCCCTNTANT TGCNTTNGGG NNCNNTGCCC      780

CTTTCCCTCT NGGGANNCG                                                  799
```

(2) INFORMATION FOR SEQ ID NO: 9:

(i) SEQUENCE CHARACTERISTICS:
        (A) LENGTH: 801 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
ACGCCTTGAT CCTCCCAGGC TGGGACTGGT TCTGGGAGGA GCCGGGCATG CTGTGGTTTG       60

TAANGATGAC ACTCCCAAAG GTGGTCCTGA CAGTGGCCCA GATGGACATG GGGCTCACCT      120

CAAGGACAAG GCCACCAGGT GCGGGGGCCG AAGCCCACAT GATCCTTACT CTATGAGCAA      180

AATCCCCTGT GGGGGCTTCT CCTTGAAGTC CGCCANCAGG GCTCAGTCTT TGGACCCANG      240

CAGGTCATGG GGTTGTNGNC CAACTGGGGG CCNCAACGCA AAANGGCNCA GGGCCTCNGN      300

CACCCATCCC ANGACGCGGC TACACTNCTG GACCTCCCNC TCCACCACTT TCATGCGCTG      360

TTCNTACCCG CGNATNTGTC CCANCTGTTT CNGTGCCNAC TCCANCTTCT NGGACGTGCG      420

CTACATACGC CCGGANTCNC NCTCCCGCTT TGTCCCTATC CACGTNCCAN CAACAAATTT      480

CNCCNTANTG CACCNATTCC CACNTTTNNC AGNTTTCCNC NNCGNGCTTC CTTNTAAAAG      540

GGTTGANCCC CGGAAAATNC CCCAAGGGG GGGGGCCNGG TACCCAACTN CCCCCTNATA      600

GCTGAANTCC CCATNACCNN GNCTCNATGG ANCCNTCCNT TTTAANNACN TTCTNAACTT      660

GGGAANANCC CTCGNCCNTN CCCCCNTTAA TCCCNCCTTG CNANGNNCNT CCCCCNNTCC      720

NCCCNNNTNG GCNTNTNANN CNAAAAAGGC CCNNNANCAA TCTCCTNNCN CCTCANTTCG      780

CCANCCCTCG AAATCGGCCN C                                               801
```

(2) INFORMATION FOR SEQ ID NO: 10:

(i) SEQUENCE CHARACTERISTICS:
        (A) LENGTH: 789 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
CAGTCTATNT GGCCAGTGTG GCAGCTTTCC CTGTGGCTGC CGGTGCCACA TGCCTGTCCC       60

ACAGTGTGGC CGTGGTGACA GCTTCAGCCG CCCTCACCGG GTTCACCTTC TCAGCCCTGC      120

AGATCCTGCC CTACACACTG GCCTCCCTCT ACCACCGGGA GAAGCAGGTG TTCCTGCCCA      180

AATACCGAGG GGACACTGGA GGTGCTAGCA GTGAGGACAG CCTGATGACC AGCTTCCTGC      240
```

```
CAGGCCCTAA GCCTGGAGCT CCCTTCCCTA ATGGACACGT GGGTGCTGGA GGCAGTGGCC      300

TGCTCCCACC TCCACCCGCG CTCTGCGGGG CCTCTGCCTG TGATGTCTCC GTACGTGTGG      360

TGGTGGGTGA GCCCACCGAN GCCAGGGTGG TTCCGGGCCG GGGCATCTGC CTGGACCTCG      420

CCATCCTGGA TAGTGCTTCC TGCTGTCCCA NGTGGCCCCA TCCCTGTTTA TGGGCTCCAT      480

TGTCCAGCTC AGCCAGTCTG TCACTGCCTA TATGGTGTCT GCCGCAGGCC TGGGTCTGGT      540

CCCATTTACT TTGCTACACA GGTANTATTT GACAAGAACG ANTTGGCCAA ATACTCAGCG      600

TTAAAAAATT CCAGCAACAT TGGGGGTGGA AGGCCTGCCT CACTGGGTCC AACTCCCCGC      660

TCCTGTTAAC CCCATGGGGC TGCCGGCTTG GCCGCCAATT TCTGTTGCTG CCAAANTNAT      720

GTGGCTCTCT GCTGCCACCT GTTGCTGGCT GAAGTGCNTA CNGCNCANCT NGGGGGGTNG      780

GGNGTTCCC                                                              789
```

(2) INFORMATION FOR SEQ ID NO: 11:

(i) SEQUENCE CHARACTERISTICS:
        (A) LENGTH: 772 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

```
CCCACCCTAC CCAAATATTA GACACCAACA CAGAAAAGCT AGCAATGGAT TCCCTTCTAC       60

TTTGTTAAAT AAATAAGTTA AATATTTAAA TGCCTGTGTC TCTGTGATGG CAACAGAAGG      120

ACCAACAGGC CACATCCTGA TAAAAGGTAA GAGGGGGGTG GATCAGCAAA AAGACAGTGC      180

TGTGGGCTGA GGGGACCTGG TTCTTGTGTG TTGCCCCTCA GGACTCTTCC CCTACAAATA      240

ACTTTCATAT GTTCAAATCC CATGGAGGAG TGTTTCATCC TAGAAACTCC CATGCAAGAG      300

CTACATTAAA CGAAGCTGCA GGTTAAGGGG CTTANAGATG GGAAACCAGG TGACTGAGTT      360

TATTCAGCTC CCAAAAACCC TTCTCTAGGT GTGTCTCAAC TAGGAGGCTA GCTGTTAACC      420

CTGAGCCTGG GTAATCCACC TGCAGAGTCC CCGCATTCCA GTGCATGGAA CCCTTCTGGC      480

CTCCCTGTAT AAGTCCAGAC TGAAACCCCC TTGGAAGGNC TCCAGTCAGG CAGCCCTANA      540

AACTGGGGAA AAAAGAAAAG GACGCCCCAN CCCCCAGCTG TGCANCTACG CACCTCAACA      600

GCACAGGGTG GCAGCAAAAA AACCACTTTA CTTTGGCACA AACAAAAACT NGGGGGGGCA      660

ACCCCGGCAC CCCNANGGGG GTTAACAGGA ANCGGGNAA CNTGGAACCC AATTNAGGCA       720

GGCCCNCCAC CCCNAATNTT GCTGGGAAAT TTTTCCTCCC CTAAATTNTT TC             772
```

(2) INFORMATION FOR SEQ ID NO: 12:

(i) SEQUENCE CHARACTERISTICS:
        (A) LENGTH: 751 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

```
GCCCCAATTC CAGCTGCCAC ACCACCCACG GTGACTGCAT TAGTTCGGAT GTCATACAAA       60

AGCTGATTGA AGCAACCCTC TACTTTTTGG TCGTGAGCCT TTTGCTTGGT GCAGGTTTCA      120

TTGGCTGTGT TGGTGACGTT GTCATTGCAA CAGAATGGGG GAAAGGCACT GTTCTCTTTG      180

AAGTANGGTG AGTCCTCAAA ATCCGTATAG TTGGTGAAGC CACAGCACTT GAGCCCTTTC      240
```

```
ATGGTGGTGT TCCACACTTG AGTGAAGTCT TCCTGGGAAC CATAATCTTT CTTGATGGCA      300

GGCACTACCA GCAACGTCAG GGAAGTGCTC AGCCATTGTG GTGTACACCA AGGCGACCAC      360

AGCAGCTGCN ACCTCAGCAA TGAAGATGAN GAGGANGATG AAGAAGAACG TCNCGAGGGC      420

ACACTTGCTC TCAGTCTTAN CACCATANCA GCCCNTGAAA ACCAANANCA AAGACCACNA      480

CNCCGGCTGC GATGAAGAAA TNACCCCNCG TTGACAAACT TGCATGGCAC TGGGANCCAC      540

AGTGGCCCNA AAAATCTTCA AAAGGATGC  CCCATCNATT GACCCCCCAA ATGCCCACTG      600

CCAACAGGGG CTGCCCCACN CNCNNAACGA TGANCCNATT GNACAAGATC TNCNTGGTCT      660

TNATNAACNT GAACCCTGCN TNGTGGCTCC TGTTCAGGNC CNNGGCCTGA CTTCTNAANN      720

AANGAACTCN GAAGNCCCCA CNGGANANNC G                                    751
```

(2) INFORMATION FOR SEQ ID NO: 13:

(i) SEQUENCE CHARACTERISTICS:
  (A) LENGTH: 729 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO: 13:

```
GAGCCAGGCG TCCCTCTGCC TGCCCACTCA GTGGCAACAC CCGGGAGCTG TTTTGTCCTT       60

TGTGGANCCT CAGCAGTNCC CTCTTTCAGA ACTCANTGCC AAGANCCCTG AACAGGAGCC      120

ACCATGCAGT GCTTCAGCTT CATTAAGACC ATGATGATCC TCTTCAATTT GCTCATCTTT      180

CTGTGTGGTG CAGCCCTGTT GGCAGTGGGC ATCTGGGTGT CAATCGATGG GGCATCCTTT      240

CTGAAGATCT TCGGGCCACT GTCGTCCAGT GCCATGCAGT TTGTCAACGT GGGCTACTTC      300

CTCATCGCAG CCGGCGTTGT GGTCTTAGCT CTAGGTTTCC TGGGCTGCTA TGGTGCTAAG      360

ACTGAGAGCA AGTGTGCCCT CGTGACGTTC TTCTTCATCC TCCTCCTCAT CTTCATTGCT      420

GAGGTTGCAA TGCTGTGGTC GCCTTGGTGT ACACCACAAT GGCTGAGCAC TTCCTGACGT      480

TGCTGGTAAT GCCTGCCATC AANAAAAGAT TATGGGTTCC CAGGAANACT TCACTCAAGT      540

GTTGGAACAC CACCATGAAA GGGCTCAAGT GCTGTGGCTT CNNCCAACTA TACGGATTTT      600

GAAGANTCAC CTACTTCAAA GAAAANAGTG CCTTTCCCCC ATTTCTGTTG CAATTGACAA      660

ACGTCCCCAA CACAGCCAAT TGAAAACCTG CACCCAACCC AAANGGGTCC CCAACCANAA      720

ATTNAAGGG                                                             729
```

(2) INFORMATION FOR SEQ ID NO: 14:

(i) SEQUENCE CHARACTERISTICS:
  (A) LENGTH: 816 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO: 14:

```
TGCTCTTCCT CAAAGTTGTT CTTGTTGCCA TAACAACCAC CATAGGTAAA GCGGGCGCAG       60

TGTTCGCTGA AGGGGTTGTA GTACCAGCGC GGGATGCTCT CCTTGCAGAG TCCTGTGTCT      120

GGCAGGTCCA CGCAGTGCCC TTTGTCACTG GGGAAATGGA TGCGCTGGAG CTCGTCAAAG      180

CCACTCGTGT ATTTTTCACA GGCAGCCTCG TCCGACGCGT CGGGGCAGTT GGGGGTGTCT      240
```

```
TCACACTCCA GGAAACTGTC NATGCAGCAG CCATTGCTGC AGCGGAACTG GGTGGGCTGA      300

CANGTGCCAG AGCACACTGG ATGGCGCCTT TCCATGNNAN GGGCCCTGNG GGAAAGTCCC      360

TGANCCCCAN ANCTGCCTCT CAAANGCCCC ACCTTGCACA CCCCGACAGG CTAGAATGGA      420

ATCTTCTTCC CGAAAGGTAG TTNTTCTTGT TGCCCAANCC ANCCCNTAA ACAAACTCTT       480

GCANATCTGC TCCGNGGGGG TCNTANTACC ANCGTGGGAA AAGAACCCCA GGCNGCGAAC      540

CAANCTTGTT TGGATNCGAA GCNATAATCT NCTNTTCTGC TTGGTGGACA GCACCANTNA      600

CTGTNNANCT TTAGNCCNTG GTCCTCNTGG GTTGNNCTTG AACCTAATCN CCNNTCAACT      660

GGGACAAGGT AANTNGCCNT CCTTTNAATT CCCNANCNTN CCCCCTGGTT TGGGGTTTTN      720

CNCNCTCCTA CCCCAGAAAN NCCGTGTTCC CCCCCAACTA GGGGCCNAAA CCNNTTNTTC      780

CACAACCCTN CCCCACCCAC GGGTTCNGNT GGTTNG                                816

(2) INFORMATION FOR SEQ ID NO: 15:

(i) SEQUENCE CHARACTERISTICS:
        (A) LENGTH: 783 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

CCAAGGCCTG GGCAGGCATA NACTTGAAGG TACAACCCCA GGAACCCCTG GTGCTGAAGG       60

ATGTGGAAAA CACAGATTGG CGCCTACTGC GGGGTGACAC GGATGTCAGG GTAGAGAGGA      120

AAGACCCAAA CCAGGTGGAA CTGTGGGGAC TCAAGGAANG CACCTACCTG TTCCAGCTGA      180

CAGTGACTAG CTCAGACCAC CCAGAGGACA CGGCCAACGT CACAGTCACT GTGCTGTCCA      240

CCAAGCAGAC AGAAGACTAC TGCCTCGCAT CCAACAANGT GGGTCGCTGC CGGGGCTCTT      300

TCCCACGCTG GTACTATGAC CCCACGGAGC AGATCTGCAA GAGTTTCGTT TATGGAGGCT      360

GCTTGGGCAA CAAGAACAAC TACCTTCGGG AAGAAGAGTG CATTCTANCC TGTCNGGGTG      420

TGCAAGGTGG GCCTTTGANA NGCANCTCTG GGGCTCANGC GACTTTCCCC CAGGGCCCCT      480

CCATGGAAAG GCGCCATCCA NTGTTCTCTG GCACCTGTCA GCCCACCCAG TTCCGCTGCA      540

NCAATGGCTG CTGCATCNAC ANTTTCCTNG AATTGTGACA ACACCCCCA NTGCCCCAA       600

CCCTCCCAAC AAAGCTTCCC TGTTNAAAAA TACNCCANTT GGCTTTTNAC AAACNCCCGG      660

CNCCTCCNTT TTCCCCNNTN AACAAAGGGC NCTNGCNTTT GAACTGCCCN AACCCNGGAA      720

TCTNCCNNGG AAAAANTNCC CCCCCTGGTT CCTNNAANCC CCTCCNCNAA ANCTNCCCCC      780

CCC                                                                   783

(2) INFORMATION FOR SEQ ID NO: 16:

(i) SEQUENCE CHARACTERISTICS:
        (A) LENGTH: 801 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

GCCCCAATTC CAGCTGCCAC ACCACCCACG GTGACTGCAT TAGTTCGGAT GTCATACAAA       60

AGCTGATTGA AGCAACCCTC TACTTTTTGG TCGTGAGCCT TTGCTTGGT GCAGGTTTCA       120

TTGGCTGTGT TGGTGACGTT GTCATTGCAA CAGAATGGGG GAAAGGCACT GTTCTCTTTG      180
```

```
AAGTAGGGTG AGTCCTCAAA ATCCGTATAG TTGGTGAAGC CACAGCACTT GAGCCCTTTC      240

ATGGTGGTGT TCCACACTTG AGTGAAGTCT TCCTGGGAAC CATAATCTTT CTTGATGGCA      300

GGCACTACCA GCAACGTCAG GAAGTGCTCA GCCATTGTGG TGTACACCAA GGCGACCACA      360

GCAGCTGCAA CCTCAGCAAT GAAGATGAGG AGGAGGATGA AGAAGAACGT CNCGAGGGCA      420

CACTTGCTCT CCGTCTTAGC ACCATAGCAG CCCANGAAAC CAAGAGCAAA GACCACAACG      480

CCNGCTGCGA ATGAAAGAAA NTACCCACGT TGACAAACTG CATGGCCACT GGACGACAGT     540

TGGCCCGAAN ATCTTCAGAA AAGGGATGCC CCATCGATTG AACACCCANA TGCCCACTGC      600

CNACAGGGCT GCNCCNCNCN GAAAGAATGA GCCATTGAAG AAGGATCNTC NTGGTCTTAA      660

TGAACTGAAA CCNTGCATGG TGGCCCCTGT TCAGGGCTCT TGGCAGTGAA TTCTGANAAA      720

AAGGAACNGC NTNAGCCCCC CCAAANGANA AAACACCCCC GGGTGTTGCC CTGAATTGGC      780

GGCCAAGGAN CCCTGCCCCN G                                                801

(2) INFORMATION FOR SEQ ID NO: 17:

(i) SEQUENCE CHARACTERISTICS:
        (A) LENGTH: 740 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

GTGAGAGCCA GGCGTCCCTC TGCCTGCCCA CTCAGTGGCA ACACCCGGGA GCTGTTTTGT       60

CCTTTGTGGA GCCTCAGCAG TTCCCTCTTT CAGAACTCAC TGCCAAGAGC CCTGAACAGG     120

AGCCACCATG CAGTGCTTCA GCTTCATTAA GACCATGATG ATCCTCTTCA ATTTGCTCAT     180

CTTTCTGTGT GGTGCAGCCC TGTTGGCAGT GGGCATCTGG GTGTCAATCG ATGGGGCATC     240

CTTTCTGAAG ATCTTCGGGC CACTGTCGTC CAGTGCCATG CAGTTTGTCA ACGTGGGCTA     300

CTTCCTCATC GCAGCCGGCG TTGTGGTCTT TGCTCTTGGT TTCCTGGGCT GCTATGGTGC     360

TAAGACGGAG AGCAAGTGTG CCCTCGTGAC GTTCTTCTTC ATCCTCCTCC TCATCTTCAT     420

TGCTGAAGTT GCAGCTGCTG TGGTCGCCTT GGTGTACACC ACAATGGCTG AACCATTCCT     480

GACGTTGCTG GTANTGCCTG CCATCAANAA AGATTATGGG TTCCCAGGAA AAATTCACTC     540

AANTNTGGAA CACCNCCATG AAAAGGGCTC CAATTTCTGN TGGCTTCCCC AACTATACCG     600

GAATTTTGAA AGANTCNCCC TACTTCCAAA AAAAAANANT TGCCTTTNCC CCCNTTCTGT     660

TGCAATGAAA ACNTCCCAAN ACNGCCAATN AAAACCTGCC CNNNCAAAAA GGNTCNCAAA     720

CAAAAAAANT NNAAGGGTTN                                                   740

(2) INFORMATION FOR SEQ ID NO: 18:

(i) SEQUENCE CHARACTERISTICS:
        (A) LENGTH: 802 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

CCGCTGGTTG CGCTGGTCCA GNGNAGCCAC GAAGCACGTC AGCATACACA GCCTCAATCA       60

CAAGGTCTTC CAGCTGCCGC ACATTACGCA GGGCAAGAGC CTCCAGCAAC ACTGCATATG     120
```

```
GGATACACTT TACTTTAGCA GCCAGGGTGA CAACTGAGAG GTGTCGAAGC TTATTCTTCT      180

GAGCCTCTGT TAGTGGAGGA AGATTCCGGG CTTCAGCTAA GTAGTCAGCG TATGTCCCAT      240

AAGCAAACAC TGTGAGCAGC CGGAAGGTAG AGGCAAAGTC ACTCTCAGCC AGCTCTCTAA      300

CATTGGGCAT GTCCAGCAGT TCTCCAAACA CGTAGACACC AGNGGCCTCC AGCACCTGAT      360

GGATGAGTGT GGCCAGCGCT GCCCCCTTGG CCGACTTGGC TAGGAGCAGA AATTGCTCCT      420

GGTTCTGCCC TGTCACCTTC ACTTCCGCAC TCATCACTGC ACTGAGTGTG GGGGACTTGG      480

GCTCAGGATG TCCAGAGACG TGGTTCCGCC CCCTCNCTTA ATGACACCGN CCANNCAACC      540

GTCGGCTCCC GCCGANTGNG TTCGTCGTNC CTGGGTCAGG GTCTGCTGGC CNCTACTTGC      600

AANCTTCGTC NGGCCCATGG AATTCACCNC ACCGGAACTN GTANGATCCA CTNNTTCTAT      660

AACCGGNCGC CACCGCNNNT GGAACTCCAC TCTTNTTNCC TTTACTTGAG GGTTAAGGTC      720

ACCCTTNNCG TTACCTTGGT CCAAACCNTN CCNTGTGTCG ANATNGTNAA TCNGGNCCNA      780

TNCCANCCNC ATANGAAGCC NG                                              802
```

(2) INFORMATION FOR SEQ ID NO: 19:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

```
CNAAGCTTCC AGGTNACGGG CCGCNAANCC TGACCCNAGG TANCANAANG CAGNCNGCGG       60

GAGCCCACCG TCACGNGGNG GNGTCTTTAT NGGAGGGGGC GGAGCCACAT CNCTGGACNT      120

CNTGACCCCA ACTCCCCNCC NCNCANTGCA GTGATGAGTG CAGAACTGAA GGTNACGTGG      180

CAGGAACCAA GANCAAANNC TGCTCCNNTC CAAGTCGGCN NAGGGGGCGG GGCTGGCCAC      240

GCNCATCCNT CNAGTGCTGN AAAGCCCCNN CCTGTCTACT TGTTTGGAGA ACNGCNNNGA      300

CATGCCCAGN GTTANATAAC NGGCNGAGAG TNANTTTGCC TCTCCCTTCC GGCTGCGCAN      360

CGNGTNTGCT TAGNGGACAT AACCTGACTA CTTAACTGAA CCCNNGAATC TNCCNCCCCT      420

CCACTAAGCT CAGAACAAAA AACTTCGACA CCACTCANTT GTCACCTGNC TGCTCAAGTA      480

AAGTGTACCC CATNCCCAAT GTNTGCTNGA NGCTCTGNCC TGCNTTANGT TCGGTCCTGG      540

GAAGACCTAT CAATTNAAGC TATGTTTCTG ACTGCCTCTT GCTCCCTGNA ACAANCNACC      600

CNNCNNTCCA AGGGGGGGNC GGCCCCCAAT CCCCCCAACC NTNAATTNAN TTTANCCCCN      660

CCCCCNGGCC CGGCCTTTTA CNANCNTCNN NNACNGGGNA AAACCNNNGC TTTNCCCAAC      720

NNAATCCNCC T                                                          731
```

(2) INFORMATION FOR SEQ ID NO: 20:

(i) SEQUENCE CHARACTERISTICS:
        (A) LENGTH: 754 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

```
TTTTTTTTTT TTTTTTTTTT TAAAAACCCC CTCCATTNAA TGNAAACTTC CGAAATTGTC       60

CAACCCCCTC NTCCAAATNN CCNTTTCCGG GNGGGGGTTC CAAACCCAAN TTANNTTTGG      120
```

```
ANNTTAAATT AAATNTTNNT TGGNGGNNNA ANCCNAATGT NANGAAAGTT NAACCCANTA    180

TNANCTTNAA TNCCTGGAAA CCNGTNGNTT CCAAAAATNT TTAACCCTTA ANTCCCTCCG    240

AAATNGTTNA NGGAAAACCC AANTTCTCNT AAGGTTGTTT GAAGGNTNAA TNAAAANCCC    300

NNCCAATTGT TTTTNGCCAC GCCTGAATTA ATTGGNTTCC GNTGTTTTCC NTTAAAANAA    360

GGNNANCCCC GGTTANTNAA TCCCCCCNNC CCCAATTATA CCGANTTTTT TTNGAATTGG    420

GANCCCNCGG GAATTAACGG GGNNNNTCCC TNTTGGGGGG CNGGNNCCCC CCCCNTCGGG    480

GGTTNGGGNC AGGNCNNAAT TGTTTAAGGG TCCGAAAAAT CCCTCCNAGA AAAAAANCTC    540

CCAGGNTGAG NNTNGGGTTT NCCCCCCCCC CANGGCCCCT CTCGNANAGT TGGGGTTTGG    600

GGGGCCTGGG ATTTTNTTTC CCCTNTTNCC TCCCCCCCCC CCNGGGANAG AGGTTNGNGT    660

TTTGNTCNNC GGCCCCNCCN AAGANCTTTN CCGANTTNAN TTAAATCCNT GCCTNGGCGA    720

AGTCCNTTGN AGGGNTAAAN GGCCCCCTNN CGGG                                754

(2) INFORMATION FOR SEQ ID NO: 21:

(i) SEQUENCE CHARACTERISTICS:
        (A) LENGTH: 755 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

ATCANCCCAT GACCCCNAAC NNGGGACCNC TCANCCGGNC NNNCNACCNC CGGCCNATCA     60

NNGTNAGNNC ACTNCNNTTN NATCACNCCC CNCCNACTAC GCCCNCNANC CNACGCNCTA    120

NNCANATNCC ACTGANNGCG CGANGTNGAN NGAGAAANCT NATACCANAG NCACCANACN    180

CCAGCTGTCC NANAAGCCT NNNATACNGG NNNATCCAAT NTGNANCCTC CNAAGTATTN     240

NNCNNCANAT GATTTTCCTN ANCCGATTAC CCNTCCCCC TANCCCCTCC CCCCCAACNA     300

CGAAGGCNCT GGNCCNAAGG NNGCGNCNCC CCGCTAGNTC CCCNNCAAGT CNCNCNCCTA    360

AACTCANCCN NATTACNCGC TTCNTGAGTA TCACTCCCCG AATCTCACCC TACTCAACTC    420

AAAAANATCN GATACAAAAT AATNCAAGCC TGNTTATNAC ACTNTGACTG GGTCTCTATT    480

TTAGNGGTCC NTNAANCNTC CTAATACTTC CAGTCTNCCT TCNCCAATTT CCNAANGGCT    540

CTTTCNGACA GCATNTTTTG GTTCCCNNTT GGGTTCTTAN NGAATTGCCC TTCNTNGAAC    600

GGGCTCNTCT TTTCCTTCGG TTANCCTGGN TTCNNCCGGC CAGTTATTAT TTCCCNTTTT    660

AAATTCNTNC CNTTTANTTT TGGCNTTCNA AACCCCCGGC CTTGAAAACG GCCCCCTGGT    720

AAAAGGTTGT TTTGANAAAA TTTTTGTTTT GTTCC                               755

(2) INFORMATION FOR SEQ ID NO: 22:

(i) SEQUENCE CHARACTERISTICS:
        (A) LENGTH: 849 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

TTTTTTTTTT TTTTANGTG TNGTCGTGCA GGTAGAGGCT TACTACAANT GTGAANACGT      60

ACGCTNGGAN TAANGCGACC CGANTTCTAG GANNCNCCCT AAAATCANAC TGTGAAGATN    120
```

```
ATCCTGNNNA CGGAANGGTC ACCGGNNGAT NNTGCTAGGG TGNCCNCTCC CANNNCNTTN      180

CATAACTCNG NGGCCCTGCC CACCACCTTC GGCGGCCCNG NGNCCGGGCC CGGGTCATTN      240

GNNTTAACCN CACTNNGCNA NCGGTTTCCN NCCCCNNCNG ACCCNGGCGA TCCGGGGTNC      300

TCTGTCTTCC CCTGNAGNCN ANAAANTGGG CCNCGGNCCC CTTTACCCCT NNACAAGCCA      360

CNGCCNTCTA NCCNCNGCCC CCCCTCCANT NNGGGGGACT GCCNANNGCT CCGTTNCTNG      420

NNACCCCNNN GGGTNCCTCG GTTGTCGANT CNACCGNANG CCANGGATTC CNAAGGAAGG      480

TGCGTTNTTG GCCCCTACCC TTCGCTNCGG NNCACCCTTC CCGACNANGA NCCGCTCCCG      540

CNCNNCGNNG CCTCNCCTCG CAACACCCGC NCTCNTCNGT NCGGNNNCCC CCCCACCCGC      600

NCCCTCNCNC NGNCGNANCN CTCCNCCNCC GTCTCANNCA CCACCCCGCC CCGCCAGGCC      660

NTCANCCACN GGNNGACNNG NAGCNCNNTC GCNCCGCGCN GCGNCNCCCT CGCCNCNGAA      720

CTNCNTCNGG CCANTNNCGC TCAANCCNNA CNAAACGCCG CTGCGCGGCC CGNAGCGNCC      780

NCCTCCNCGA GTCCTCCCGN CTTCCNACCC ANGNNTTCCN CGAGGACACN NNACCCCGCC      840

NNCANGCGG                                                             849

(2) INFORMATION FOR SEQ ID NO: 23:

(i) SEQUENCE CHARACTERISTICS:
        (A) LENGTH: 872 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

GCGCAAACTA TACTTCGCTC GNACTCGTGC GCCTCGCTNC TCTTTTCCTC CGCAACCATG       60

TCTGACNANC CCGATTNGGC NGATATCNAN AAGNTCGANC AGTCCAAACT GANTAACACA      120

CACACNCNAN AGANAAATCC NCTGCCTTCC ANAGTANACN ATTGAACNNG AGAACCANGC      180

NGGCGAATCG TAATNAGGCG TGCGCCGCCA ATNTGTCNCC GTTTATTNTN CCAGCNTCNC      240

CTNCCNACCC TACNTCTTCN NAGCTGTCNN ACCCCTNGTN CGNACCCCCC NAGGTCGGGA      300

TCGGGTTTNN NNTGACCGNG CNNCCCCTCC CCCCNTCCAT NACGANCCNC CCGCACCACC      360

NANNGCNCGC NCCCCGNNCT CTTCGCCNCC CTGTCCTNTN CCCCTGTNGC CTGGCNCNGN      420

ACCGCATTGA CCCTCGCCNN CTNCNNGAAA NCGNANACGT CCGGGTTGNN ANNANCGCTG      480

TGGGNNNGCG TCTGCNCCGC GTTCCTTCCN NCNNCTTCCA CCATCTTCNT TACNGGGTCT      540

CCNCGCCNTC TCNNNCACNC CCTGGGACGC TNTCCTNTGC CCCCCTTNAC TCCCCCCCTT      600

CGNCGTGNCC CGNCCCCACC NTCATTTNCA NACGNTCTTC ACAANNNCCT GGNTNNCTCC      660

CNANCNGNCN GTCANCCNAG GGAAGGGNGG GGNNCCNNTG NTTGACGTTG NGGNGANGTC      720

CGAANANTCC TCNCCNTCAN CNCTACCCCT CGGGCGNNCT CTCNGTTNCC AACTTANCAA      780

NTCTCCCCCG NGNGCNCNTC TCAGCCTCNC CCNCCCCNCT CTCTGCANTG TNCTCTGCTC      840

TNACCNNTAC GANTNTTCGN CNCCCTCTTT CC                                   872

(2) INFORMATION FOR SEQ ID NO: 24:

(i) SEQUENCE CHARACTERISTICS:
        (A) LENGTH: 815 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO: 24:

```
GCATGCAAGC TTGAGTATTC TATAGNGTCA CCTAAATANC TTGGCNTAAT CATGGTCNTA      60

NCTGNCTTCC TGTGTCAAAT GTATACNAAN TANATATGAA TCTNATNTGA CAAGANNGTA     120

TCNTNCATTA GTAACAANTG TNNTGTCCAT CCTGTCNGAN CANATTCCCA TNNATTNCGN     180

CGCATTCNCN GCNCANTATN TAATNGGGAA NTCNNNTNNN NCACCNNCAT CTATCNTNCC     240

GCNCCCTGAC TGGNAGAGAT GGATNANTTC TNNTNTGACC NACATGTTCA TCTTGGATTN     300

AANANCCCCC CGCNGNCCAC CGGTTNGNNG CNAGCCNNTC CCAAGACCTC CTGTGGAGGT     360

AACCTGCGTC AGANNCATCA AACNTGGGAA ACCCGCNNCC ANGTNNAAGT NGNNNCANAN     420

GATCCCGTCC AGGNTTNACC ATCCCTTCNC AGCGCCCCCT TTNGTGCCTT ANAGNGNAGC     480

GTGTCCNANC CNCTCAACAT GANACGCGCC AGNCCANCCG CAATTNGGCA CAATGTCGNC     540

GAACCCCCTA GGGGGANTNA TNCAAANCCC CAGGATTGTC CNCNCANGAA ATCCCNCANC     600

CCCNCCCTAC CCNNCTTTGG GACNGTGACC AANTCCCGGA GTNCCAGTCC GGCCNGNCTC     660

CCCCACCGGT NNCCNTGGGG GGGTGAANCT CNGNNTCANC CNGNCGAGGN NTCGNAAGGA     720

ACCGGNCCTN GGNCGAANNG ANCNNTCNGA AGNGCCNCNT CGTATAACCC CCCCTCNCCA     780

NCCNACNGNT AGNTCCCCCC CNGGGTCNGG AANGG                                815
```

(2) INFORMATION FOR SEQ ID NO: 25:

(i) SEQUENCE CHARACTERISTICS:
        (A) LENGTH: 775 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

```
CCGAGATGTC TCGCTCCGTG GCCTTAGCTG TGCTCGCGCT ACTCTCTCTT TCTGGCCTGG      60

AGGCTATCCA GCGTACTCCA AAGATTCAGG TTTACTCACG TCATCCAGCA GAGAATGGAA     120

AGTCAAATTT CCTGAATTGC TATGTGTCTG GGTTTCATCC ATCCGACATT GAANTTGACT     180

TACTGAAGAA TGGANAGAGA ATTGAAAAAG TGGAGCATTC AGACTTGTCT TTCAGCAAGG     240

ACTGGTCTTT CTATCTCNTG TACTACACTG AATTCACCCC CACTGAAAAA GATGAGTATG     300

CCTGCCGTGT GAACCATGTG ACTTTGTCAC AGCCCAAGAT AGTTAAGTGG ATCGAGACA      360

TGTAAGCAGN CNNCATGGAA GTTTGAAGAT GCCGCATTTG GATTGGATGA ATTCCAAATT     420

CTGCTTGCTT GCNTTTTAAT ANTGATATGC NTATACACCC TACCCTTTAT GNCCCCAAAT     480

TGTAGGGGTT ACATNANTGT TCNCNTNGGA CATGATCTTC CTTTATAANT CCNCCNTTCG     540

AATTGCCCGT CNCCCNGTTN NGAATGTTTC CNNAACCACG GTTGGCTCCC CCAGGTCNCC     600

TCTTACGGAA GGGCCTGGGC CNCTTTCAA GGTTGGGGGA ACCNAAAATT TCNCTTNTGC     660

CCNCCCNCCA CNNTCTTGNG NNCNCANTTT GGAACCCTTC CNATTCCCCT TGGCCTCNNA     720

NCCTTNNCTA ANAAAACTTN AAANCGTNGC NAAANNTTTN ACTTCCCCCC TTACC         775
```

(2) INFORMATION FOR SEQ ID NO: 26:

(i) SEQUENCE CHARACTERISTICS:
        (A) LENGTH: 820 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

```
ANATTANTAC AGTGTAATCT TTTCCCAGAG GTGTGTANAG GGAACGGGGC CTAGAGGCAT      60
CCCANAGATA NCTTATANCA ACAGTGCTTT GACCAAGAGC TGCTGGGCAC ATTTCCTGCA     120
GAAAAGGTGG CGGTCCCCAT CACTCCTCCT CTCCCATAGC CATCCCAGAG GGGTGAGTAG     180
CCATCANGCC TTCGGTGGGA GGGAGTCANG GAAACAACAN ACCACAGAGC ANACAGACCA     240
NTGATGACCA TGGGCGGGAG CGAGCCTCTT CCCTGNACCG GGGTGGCANA NGANAGCCTA     300
NCTGAGGGGT CACACTATAA ACGTTAACGA CCNAGATNAN CACCTGCTTC AAGTGCACCC     360
TTCCTACCTG ACNACCAGNG ACCNNNAACT GCNGCCTGGG GACAGCNCTG GGANCAGCTA     420
ACNNAGCACT CACCTGCCCC CCCATGGCCG TNCGCNTCCC TGGTCCTGNC AAGGGAAGCT     480
CCCTGTTGGA ATTNCGGGA NACCAAGGGA NCCCCTCCT CCANCTGTGA AGGAAAAANN      540
GATGGAATTT TNCCCTTCCG GCCNNTCCCC TCTTCCTTTA CACGCCCCCT NNTACTCNTC     600
TCCCTCTNTT NTCCTGNCNC ACTTTTNACC CCNNNATTTC CCTTNATTGA TCGGANNCTN     660
GANATTCCAC TNNCGCCTNC CNTCNATCNG NAANACNAAA NACTNTCTNA CCCNGGGGAT     720
GGGNNCCTCG NTCATCCTCT CTTTTTCNCT ACCNCCNNTT CTTTGCCTCT CCTTNGATCA     780
TCCAACCNTC GNTGGCCNTN CCCCCCCNNN TCCTTTNCCC                          820
```

(2) INFORMATION FOR SEQ ID NO: 27:

(i) SEQUENCE CHARACTERISTICS:
            (A) LENGTH: 818 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 27:

```
TCTGGGTGAT GGCCTCTTCC TCCTCAGGGA CCTCTGACTG CTCTGGGCCA AAGAATCTCT      60
TGTTTCTTCT CCGAGCCCCA GGCAGCGGTG ATTCAGCCCT GCCCAACCTG ATTCTGATGA     120
CTGCGGATGC TGTGACGGAC CCAAGGGGCA AATAGGGTCC CAGGGTCCAG GGAGGGGCGC     180
CTGCTGAGCA CTTCCGCCCC TCACCCTGCC CAGCCCCTGC CATGAGCTCT GGGCTGGGTC     240
TCCGCCTCCA GGGTTCTGCT CTTCCANGCA NGCCANCAAG TGGCGCTGGG CCACACTGGC     300
TTCTTCCTGC CCCNTCCCTG GCTCTGANTC TCTGTCTTCC TGTCCTGTGC ANGCNCCTTG     360
GATCTCAGTT TCCCTCNCTC ANNGAACTCT GTTTCTGANN TCTTCANTTA ACTNTGANTT     420
TATNACCNAN TGGNCTGTNC TGTCNNACTT TAATGGGCCN GACCGGCTAA TCCCTCCCTC     480
NCTCCCTTCC ANTTCNNNNA ACCNGCTTNC CNTCNTCTCC CCNTANCCCG CCNGGGAANC     540
CTCCTTTGCC CTNACCANGG GCCNNNACCG CCCNTNNCTN GGGGGGCNNG GTNNCTNCNC     600
CTGNTNNCCC CNCTCNCNNT TNCCTCGTCC CNNCNNCGCN NNGCANNTTC NCNGTCCCNN     660
TNNCTCTTCN NGTNTCGNAA NGNTCNCNTN TNNNNNGNCN NGNTNNTNCN TCCCTCTCNC     720
CNNNTGNANG TNNTTNNNNC NCNGNNCCCC NNNNCNNNNN NGGNNNTNNN TCTNCNCNGC     780
CCCNNCCCCC NGNATTAAGG CCTCCNNTCT CCGGCCNC                            818
```

(2) INFORMATION FOR SEQ ID NO: 28:

(i) SEQUENCE CHARACTERISTICS:
            (A) LENGTH: 731 base pairs
            (B) TYPE: nucleic acid

```
            (C) STRANDEDNESS: single
            (D) TOPOLOGY: linear (ii) MOLECULE TYPE: cDNA (xi) SEQUENCE DESCRIPTION: SEQ ID NO: 28:

AGGAAGGGCG GAGGGATATT GTANGGGATT GAGGGATAGG AGNATAANGG GGGAGGTGTG        60

TCCCAACATG ANGGTGNNGT TCTCTTTTGA ANGAGGGTTG NGTTTTTANN CCNGGTGGGT       120

GATTNAACCC CATTGTATGG AGNNAAAGGN TTTNAGGGAT TTTTCGGCTC TTATCAGTAT       180

NTANATTCCT GTNAATCGGA AAATNATNTT TCNNCNGGAA AATNTTGCTC CCATCCGNAA       240

ATTNCTCCCG GGTAGTGCAT NTTNGGGGGN CNGCCANGTT TCCCAGGCTG CTANAATCGT       300

ACTAAAGNTT NAAGTGGGAN TNCAAATGAA AACCTNNCAC AGAGNATCCN TACCCGACTG       360

TNNNTTNCCT TCGCCCTNTG ACTCTGCNNG AGCCCAATAC CCNNGNGNAT GTCNCCCNGN       420

NNNGCGNCNC TGAAANNNNC TCGNGGCTNN GANCATCANG GGGTTTCGCA TCAAAAGCNN       480

CGTTTCNCAT NAAGGCACTT TNGCCTCATC CAACCNCTNG CCCTCNNCCA TTTNGCCGTC       540

NGGTTCNCCT ACGCTNNTNG CNCCTNNNTN GANATTTTNC CCGCCTNGGG NAANCCTCCT       600

GNAATGGGTA GGGNCTTNTC TTTTNACCNN GNGGTNTACT AATCNNCTNC ACGCNTNCTT       660

TCTCNACCCC CCCCCTTTTT CAATCCCANC GGCNAATGGG GTCTCCCCNN CGANGGGGGG       720

NNNCCCANNC C                                                           731

(2) INFORMATION FOR SEQ ID NO: 29:

(i) SEQUENCE CHARACTERISTICS:
        (A) LENGTH: 822 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

ACTAGTCCAG TGTGGTGGAA TTCCATTGTG TTGGGGNCNC TTCTATGANT ANTNTTAGAT        60

CGCTCANACC TCACANCCTC CCNACNANGC CTATAANGAA NANNAATAGA NCTGTNCNNT       120

ATNTNTACNC TCATANNCCT CNNNACCCAC TCCCTCTTAA CCCNTACTGT GCCTATNGCN       180

TNNCTANTCT NTGCCGCCTN CNANCCACCN GTGGGCCNAC CNCNNGNATT CTCNATCTCC       240

TCNCCATNTN GCCTANANTA NGTNCATACC CTATACCTAC NCCAATGCTA NNNCTAANCN       300

TCCATNANTT ANNNTAACTA CCACTGACNT NGACTTTCNC ATNANCTCCT AATTTGAATC       360

TACTCTGACT CCCACNGCCT ANNNATTAGC ANCNTCCCCC NACATNTCT CAACCAAATC        420

NTCAACAACC TATCTANCTG TTCNCCAACC NTTNCCTCCG ATCCCNNAC AACCCCCCTC        480

CCAAATACCC NCCACCTGAC NCCTAACCCN CACCATCCCG GCAAGCCNAN GGNCATTTAN       540

CCACTGGAAT CACNATNGGA NAAAAAAAAC CCNAACTCTC TANCNCNNAT CTCCCTAANA       600

AATNCTCCTN NAATTTACTN NCANTNCCAT CAANCCCACN TGAAACNNAA CCCCTGTTTT       660

TANATCCCTT CTTTCGAAAA CCNACCCTTT ANNNCCCAAC CTTTNGGGCC CCCCCNCTNC       720

CCNAATGAAG GNCNCCCAAT CNANGAAACG NCCNTGAAAA ANCNAGGCNA ANANNNTCCG       780

CANATCCTAT CCCTTANTTN GGGGNCCCTT NCCCNGGGCC CC                         822

(2) INFORMATION FOR SEQ ID NO: 30:

(i) SEQUENCE CHARACTERISTICS:
        (A) LENGTH: 787 base pairs
```

(B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

| | | | | | |
|---|---|---|---|---|---|
| CGGCCGCCTG | CTCTGGCACA | TGCCTCCTGA | ATGGCATCAA | AAGTGATGGA | CTGCCCATTG | 60 |
| CTAGAGAAGA | CCTTCTCTCC | TACTGTCATT | ATGGAGCCCT | GCAGACTGAG | GGCTCCCCTT | 120 |
| GTCTGCAGGA | TTTGATGTCT | GAAGTCGTGG | AGTGTGGCTT | GGAGCTCCTC | ATCTACATNA | 180 |
| GCTGGAAGCC | CTGGAGGGCC | TCTCTCGCCA | GCCTCCCCCT | TCTCTCCACG | CTCTCCANGG | 240 |
| ACACCAGGGG | CTCCAGGCAG | CCCATTATTC | CCAGNANGAC | ATGGTGTTTC | TCCACGCGGA | 300 |
| CCCATGGGGC | CTGNAAGGCC | AGGGTCTCCT | TTGACACCAT | CTCTCCCGTC | CTGCCTGGCA | 360 |
| GGCCGTGGGA | TCCACTANTT | CTANAACGGN | CGCCACCNCG | GTGGGAGCTC | CAGCTTTTGT | 420 |
| TCCCNTTAAT | GAAGGTTAAT | TGCNCGCTTG | GCGTAATCAT | NGGTCANAAC | TNTTTCCTGT | 480 |
| GTGAAATTGT | TTNTCCCCTC | NCNATTCCNC | NCNACATACN | AACCCGGAAN | CATAAAGTGT | 540 |
| TAAAGCCTGG | GGGTNGCCTN | NNGAATNAAC | TNAACTCAAT | TAATTGCGTT | GGCTCATGGC | 600 |
| CCGCTTTCCN | TTCNGGAAAA | CTGTCNTCCC | CTGCNTTNNT | GAATCGGCCA | CCCCCCNGGG | 660 |
| AAAAGCGGTT | TGCNTTTTNG | GGGGNTCCTT | CCNCTTCCCC | CCTCNCTAAN | CCCTNCGCCT | 720 |
| CGGTCGTTNC | NGGTNGCGGG | GAANGGGNAT | NNNCTCCCNC | NAAGGGGGNG | AGNNNGNTAT | 780 |
| CCCCAAA | | | | | | 787 |

(2) INFORMATION FOR SEQ ID NO: 31:

(i) SEQUENCE CHARACTERISTICS:
        (A) LENGTH: 799 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

| | | | | | |
|---|---|---|---|---|---|
| TTTTTTTTTT | TTTTTTTGGC | GATGCTACTG | TTTAATTGCA | GGAGGTGGGG | GTGTGTGTAC | 60 |
| CATGTACCAG | GGCTATTAGA | AGCAAGAAGG | AAGGAGGGAG | GGCAGAGCGC | CCTGCTGAGC | 120 |
| AACAAAGGAC | TCCTGCAGCC | TTCTCTGTCT | GTCTCTTGGC | GCAGGCACAT | GGGGAGGCCT | 180 |
| CCCGCAGGGT | GGGGGCCACC | AGTCCAGGGG | TGGGAGCACT | ACANGGGGTG | GGAGTGGGTG | 240 |
| GTGGCTGGTN | CNAATGGCCT | GNCACANATC | CCTACGATTC | TTGACACCTG | GATTTCACCA | 300 |
| GGGGACCTTC | TGTTCTCCCA | NGGNAACTTC | NTNNATCTCN | AAAGAACACA | ACTGTTTCTT | 360 |
| CNGCANTTCT | GGCTGTTCAT | GGAAAGCACA | GGTGTCCNAT | TTNGGCTGGG | ACTTGGTACA | 420 |
| TATGGTTCCG | GCCCACCTCT | CCCNTCNAAN | AAGTAATTCA | CCCCCCCCN | CCNTCTNTTG | 480 |
| CCTGGGCCCT | TAANTACCCA | CACCGGAACT | CANTTANTTA | TTCATCTTNG | GNTGGGCTTG | 540 |
| NTNATCNCCN | CCTGAANGCG | CCAAGTTGAA | AGGCACGCC | GTNCCNCTC | CCCATAGNAN | 600 |
| NTTTTNNCNT | CANCTAATGC | CCCCCCNGGC | AACNATCCAA | TCCCCCCCN | TGGGGGCCCC | 660 |
| AGCCCANGGC | CCCCGNCTCG | GGNNNCCNGN | CNCGNANTCC | CCAGGNTCTC | CCANTCNGNC | 720 |
| CCNNNGCNCC | CCCGCACGCA | GAACANAAGG | NTNGAGCCNC | CGCANNNNNN | NGGTNNCNAC | 780 |
| CTCGCCCCCC | CCNNCGNNG | | | | | 799 |

(2) INFORMATION FOR SEQ ID NO: 32:

(i) SEQUENCE CHARACTERISTICS:
    (A) LENGTH: 789 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 32:

```
TTTTTTTTTT TTTTTTTTTT TTTTTTTTTT TTTTTTTTTT TTTTTTTTTT TTTTTTTTTT      60
TTTTNCCNAG GCAGGTTTA TTGACAACCT CNCGGGACAC AANCAGGCTG GGACAGGAC       120
GGCAACAGGC TCCGGCGGCG GCGGCGGCGG CCCTACCTGC GGTACCAAAT NTGCAGCCTC     180
CGCTCCCGCT TGATNTTCCT CTGCAGCTGC AGGATGCCNT AAAACAGGGC CTCGGCCNTN     240
GGTGGGCACC CTGGGATTTN AATTTCCACG GGCACAATGC GGTCGCANCC CCTCACCACC     300
NATTAGGAAT AGTGGTNTTA CCCNCCNCCG TTGGCNCACT CCCCNTGGAA ACCACTTNTC     360
GCGGCTCCGG CATCTGGTCT TAAACCTTGC AAACNCTGGG GCCCTCTTTT TGGTTANTNT     420
NCCNGCCACA ATCATNACTC AGACTGGCNC GGGCTGGCCC CAAAAAANCN CCCCAAAACC     480
GGNCCATGTC TTNNCGGGGT TGCTGCNATN TNCATCACCT CCCGGGCNCA NCAGGNCAAC     540
CCAAAAGTTC TTGNGGCCCN CAAAAAANCT CCGGGGGGNC CCAGTTTCAA CAAAGTCATC     600
CCCCTTGGCC CCCAAATCCT CCCCCCGNTT NCTGGGTTTG GGAACCCACG CCTCTNNCTT     660
TGGNNGGCAA GNTGGNTCCC CCTTCGGGCC CCCGGTGGGC CCNNCTCTAA NGAAAACNCC     720
NTCCTNNNCA CCATCCCCCC NNGNNACGNC TANCAANGNA TCCCTTTTTT TANAAACGGG     780
CCCCCCNCG                                                             789
```

(2) INFORMATION FOR SEQ ID NO: 33:

(i) SEQUENCE CHARACTERISTICS:
    (A) LENGTH: 793 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 33:

```
GACAGAACAT GTTGGATGGT GGAGCACCTT TCTATACGAC TTACAGGACA GCAGATGGGG      60
AATTCATGGC TGTTGGAGCA ATANAACCCC AGTTCTACGA GCTGCTGATC AAAGGACTTG     120
GACTAAAGTC TGATGAACTT CCCAATCAGA TGAGCATGGA TGATTGGCCA GAAATGAANA     180
AGAAGTTTGC AGATGTATTT GCAAAGAAGA CGAAGGCAGA GTGGTGTCAA ATCTTTGACG     240
GCACAGATGC CTGTGTGACT CCGGTTCTGA CTTTTGAGGA GGTTGTTCAT CATGATCACA     300
ACAANGAACG GGGCTCGTTT ATCACCANTG AGGAGCAGGA CGTGAGCCCC CGCCCTGCAC     360
CTCTGCTGTT AAACACCCCA GCCATCCCTT CTTTCAAAAG GGATCCACTA CTTCTAGAGC     420
GGNCGCCACC GCGGTGGAGC TCCAGCTTTT GTTCCCTTTA GTGAGGGTTA ATTGCGCGCT     480
TGGCGTAATC ATGGTCATAN CTGTTTCCTG TGTGAAATTG TTATCCGCTC ACAATTCCAC     540
ACAACATACG ANCCGGAAGC ATNAAATTTT AAAGCCTGGN GGTNGCCTAA TGANTGAACT     600
NACTCACATT AATTGGCTTT GCGCTCACTG CCCGCTTTCC AGTCCGGAAA ACCTGTCCTT     660
GCCAGCTGCC NTTAATGAAT CNGGCCACCC CCCGGGGAAA AGGCGNTTTG CTTNTTGGGG     720
CGCNCTTCCC GCTTTCTCGC TTCCTGAANT CCTTCCCCCC GGTCTTTCGG CTTGCGGCNA     780
ACGGTATCNA CCT                                                        793
```

(2) INFORMATION FOR SEQ ID NO: 34:

(i) SEQUENCE CHARACTERISTICS:
        (A) LENGTH: 756 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 34:

```
GCCGCGACCG GCATGTACGA GCAACTCAAG GGCGAGTGGA ACCGTAAAAG CCCCAATCTT      60
ANCAAGTGCG GGGAANAGCT GGGTCGACTC AAGCTAGTTC TTCTGGAGCT CAACTTCTTG     120
CCAACCACAG GGACCAAGCT GACCAAACAG CAGCTAATTC TGGCCCGTGA CATACTGGAG     180
ATCGGGGCCC AATGGAGCAT CCTACGCAAN GACATCCCCT CCTTCGAGCG CTACATGGCC     240
CAGCTCAAAT GCTACTACTT TGATTACAAN GAGCAGCTCC CCGAGTCAGC CTATATGCAC     300
CAGCTCTTGG GCCTCAACCT CCTCTTCCTG CTGTCCCAGA ACCGGGTGGC TGANTNCCAC     360
ACGGANTTGG ANCGGCTGCC TGCCCAANGA CATACANACC AATGTCTACA TCNACCACCA     420
GTGTCCTGGA GCAATACTGA TGGANGGCAG CTACCNCAAA GTNTTCCTGG CCNAGGGTAA     480
CATCCCCCGC CGAGAGCTAC ACCTTCTTCA TTGACATCCT GCTCGACACT ATCAGGGATG     540
AAAATCGCNG GGTTGCTCCA GAAAGGCTNC AANAANATCC TTTTCNCTGA AGGCCCCCGG     600
ATNCNCTAGT NCTAGAATCG GCCCGCCATC GCGGTGGANC CTCCAACCTT TCGTTNCCCT     660
TTACTGAGGG TTNATTGCCG CCCTTGGCGT TATCATGGTC ACNCCNGTTN CCTGTGTTGA     720
AATTNTTAAC CCCCCACAAT TCCACGCCNA CATTNG                              756
```

(2) INFORMATION FOR SEQ ID NO: 35:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

```
GGGGATCTCT ANATCNACCT GNATGCATGG TTGTCGGTGT GGTCGCTGTC GATGAAANATG     60
AACAGGATCT TGCCCTTGAA GCTCTCGGCT GCTGTNTTTA AGTTGCTCAG TCTGCCGTCA    120
TAGTCAGACA CNCTCTTGGG CAAAAAACAN CAGGATNTGA GTCTTGATTT CACCTCCAAT    180
AATCTTCNGG GCTGTCTGCT CGGTGAACTC GATGACNANG GGCAGCTGGT TGTGTNTGAT    240
AAANTCCANC ANGTTCTCCT TGGTGACCTC CCCTTCAAAG TTGTTCCGGC CTTCATCAAA    300
CTTCTNNAAN ANGANNANCC CANCTTTGTC GAGCTGGNAT TTGGANAACA CGTCACTGTT    360
GGAAACTGAT CCCAAATGGT ATGTCATCCA TCGCCTCTGC TGCCTGCAAA AAACTTGCTT    420
GGCNCAAATC CGACTCCCCN TCCTTGAAAG AAGCCNATCA CACCCCCCTC CCTGGACTCC    480
NNCAANGACT CTNCCGCTNC CCCNTCCNNG CAGGGTTGGT GGCANNCCGG GCCCNTGCGC    540
TTCTTCAGCC AGTTCACNAT NTTCATCAGC CCCTCTGCCA GCTGTTNTAT TCCTTGGGGG    600
GGAANCCGTC TCTCCCTTCC TGAANNAACT TTGACCGTNG GAATAGCCGC GCNTCNCCNT    660
ACNTNCTGGG CCGGGTTCAA ANTCCCTCCN TTGNCNNTCN CCTCGGGCCA TTCTGGATTT    720
NCCNAACTTT TTCCTTCCCC CNCCCCNCGG NGTTTGGNTT TTTCATNGGG CCCCAACTCT    780
```

| GCTNTTGGCC ANTCCCCTGG GGGCNTNTAN CNCCCCCTNT GGTCCCNTNG GGCC | 834 |

(2) INFORMATION FOR SEQ ID NO: 36:

(i) SEQUENCE CHARACTERISTICS:
        (A) LENGTH: 814 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 36:

| CGGNCGCTTT CCNGCCGCGC CCCGTTTCCA TGACNAAGGC TCCCTTCANG TTAAATACNN | 60 |
| CCTAGNAAAC ATTAATGGGT TGCTCTACTA ATACATCATA CNAACCAGTA AGCCTGCCCA | 120 |
| NAACGCCAAC TCAGGCCATT CCTACCAAAG GAAGAAAGGC TGGTCTCTCC ACCCCCTGTA | 180 |
| GGAAAGGCCT GCCTTGTAAG ACACCACAAT NCGGCTGAAT CTNAAGTCTT GTGTTTTACT | 240 |
| AATGGAAAAA AAAAATAAAC AANAGGTTTT GTTCTCATGG CTGCCCACCG CAGCCTGGCA | 300 |
| CTAAAACANC CCAGCGCTCA CTTCTGCTTG GANAAATATT CTTTGCTCTT TTGGACATCA | 360 |
| GGCTTGATGG TATCACTGCC ACNTTTCCAC CCAGCTGGGC NCCCTTCCCC CATNTTTGTC | 420 |
| ANTGANCTGG AAGGCCTGAA NCTTAGTCTC CAAAAGTCTC NGCCCACAAG ACCGGCCACC | 480 |
| AGGGGANGTC NTTTNCAGTG GATCTGCCAA ANANTACCCN TATCATCNNT GAATAAAAAG | 540 |
| GCCCCTGAAC GANATGCTTC CANCANCCTT TAAGACCCAT AATCCTNGAA CCATGGTGCC | 600 |
| CTTCCGGTCT GATCCNAAAG GAATGTTCCT GGGTCCCANT CCCTCCTTTG TTNCTTACGT | 660 |
| TGTNTTGGAC CCNTGCTNGN ATNACCCAAN TGANATCCCC NGAAGCACCC TNCCCCTGGC | 720 |
| ATTTGANTTT CNTAAATTCT CTGCCCTACN NCTGAAAGCA CNATTCCCTN GGCNCCNAAN | 780 |
| GGNGAACTCA AGAAGGTCTN NGAAAAACCA CNCN | 814 |

(2) INFORMATION FOR SEQ ID NO: 37:

(i) SEQUENCE CHARACTERISTICS:
        (A) LENGTH: 760 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

| GCATGCTGCT CTTCCTCAAA GTTGTTCTTG TTGCCATAAC AACCACCATA GGTAAAGCGG | 60 |
| GCGCAGTGTT CGCTGAAGGG GTTGTAGTAC CAGCGCGGGA TGCTCTCCTT GCAGAGTCCT | 120 |
| GTGTCTGGCA GGTCCACGCA ATGCCCTTTG TCACTGGGGA AATGGATGCG CTGGAGCTCG | 180 |
| TCNAANCCAC TCGTGTATTT TTCACANGCA GCCTCCTCCG AAGCNTCCGG GCAGTTGGGG | 240 |
| GTGTCGTCAC ACTCCACTAA ACTGTCGATN CANCAGCCCA TTGCTGCAGC GGAACTGGGT | 300 |
| GGGCTGACAG GTGCCAGAAC ACACTGGATN GGCCTTTCCA TGGAAGGGCC TGGGGGAAAT | 360 |
| CNCCTNANCC CAAACTGCCT CTCAAAGGCC ACCTTGCACA CCCCGACAGG CTAGAAATGC | 420 |
| ACTCTTCTTC CCAAAGGTAG TTGTTCTTGT TGCCCAAGCA NCCTCCANCA AACCAAAANC | 480 |
| TTGCAAAATC TGCTCCGTGG GGGTCATNNN TACCANGGTT GGGGAAANAA ACCCGGCNGN | 540 |
| GANCCNCCTT GTTTGAATGC NAAGGNAATA ATCCTCCTGT CTTGCTTGGG TGGAANAGCA | 600 |
| CAATTGAACT GTTAACNTTG GGCCGNGTTC CNCTNGGGTG GTCTGAAACT AATCACCGTC | 660 |
| ACTGGAAAAA GGTANGTGCC TTCCTTGAAT TCCCAAANTT CCCCTNGNTT TGGGTNNTTT | 720 |

CTCCTCTNCC CTAAAAATCG TNTTCCCCCC CCNTANGGCG                    760

(2) INFORMATION FOR SEQ ID NO: 38:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 38:

TTTTTTTTTT TTTTTTTTTT TTTTTTTTTT TTTTTAAAAA CCCCCTCCAT TGAATGAAAA     60

CTTCCNAAAT TGTCCAACCC CCTCNNCCAA ATNNCCATTT CCGGGGGGGG GTTCCAAACC    120

CAAATTAATT TTGGANTTTA AATTAAATNT TNATTNGGGG AANAANCCAA ATGTNAAGAA    180

AATTTAACCC ATTATNAACT TAAATNCCTN GAAACCCNTG GNTTCCAAAA ATTTTTAACC    240

CTTAAATCCC TCCGAAATTG NTAANGGAAA ACCAAATTCN CCTAAGGCTN TTTGAAGGTT    300

NGATTTAAAC CCCCTTNANT TNTTTTNACC CNNGNCTNAA NTATTTNGNT TCCGGTGTTT    360

TCCTNTTAAN CNTNGGTAAC TCCCGNTAAT GAANNNCCCT AANCCAATTA AACCGAATTT    420

TTTTTGAATT GGAAATTCCN NGGGAATTNA CCGGGGTTTT TCCCNTTTGG GGGCCATNCC    480

CCCNCTTTCG GGGTTTGGGN NTAGGTTGAA TTTTTNNANG NCCCAAAAAA NCCCCCAANA    540

AAAAAACTCC CAAGNNTTAA TTNGAATNTC CCCCTTCCCA GGCCTTTTGG GAAAGGNGGG    600

TTTNTGGGGG CCNGGGANTT CNTTCCCCCN TTNCCNCCCC CCCCCCNGGT AAANGGTTAT    660

NGNNTTTGGT TTTTGGGCCC CTTNANGGAC CTTCCGGATN GAAATTAAAT CCCCGGGNCG    720

GCCG                                                               724

(2) INFORMATION FOR SEQ ID NO: 39:

(i) SEQUENCE CHARACTERISTICS:
        (A) LENGTH: 751 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:

TTTTTTTTTT TTTTCTTTG CTCACATTTA ATTTTTATTT TGATTTTTTT TAATGCTGCA      60

CAACACAATA TTTATTTCAT TTGTTTCTTT TATTTCATTT TATTTGTTTG CTGCTGCTGT    120

TTTATTTATT TTTACTGAAA GTGAGAGGGA ACTTTTGTGG CCTTTTTTCC TTTTTCTGTA    180

GGCCGCCTTA AGCTTTCTAA ATTTGGAACA TCTAAGCAAG CTGAANGGAA AAGGGGGTTT    240

CGCAAAATCA CTCGGGGGAA NGGAAAGGTT GCTTTGTTAA TCATGCCCTA TGGTGGGTGA    300

TTAACTGCTT GTACAATTAC NTTTCACTTT TAATTAATTG TGCTNAANGC TTTAATTANA    360

CTTGGGGGTT CCCTCCCCAN ACCAACCCCN CTGACAAAAA GTGCCNGCCC TCAAATNATG    420

TCCCGGCNNT CNTTGAAACA CACNGCNGAA NGTTCTCATT NTCCCCNCNC CAGGTNAAAA    480

TGAAGGGTTA CCATNTTTAA CNCCACCTCC ACNTGGCNNN GCCTGAATCC TCNAAAANCN    540

CCCTCAANCN AATTNCTNNG CCCCGGTCNC GCNTNNGTCC CNCCCGGGCT CCGGGAANTN    600

CACCCCCNGA ANNCNNTNNC NAACNAAATT CCGAAAATAT TCCCNNTCNC TCAATTCCCC    660

CNNAGACTNT CCTCNNCNAN CNCAATTTTC TTTTNNTCAC GAACNCGNNC CNNAAAATGN    720

```
NNNNCNCCTC CNCTNGTCCN NAATCNCCAN C                              751
```

(2) INFORMATION FOR SEQ ID NO: 40:

(i) SEQUENCE CHARACTERISTICS:
        (A) LENGTH: 753 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 40:

```
GTGGTATTTT CTGTAAGATC AGGTGTTCCT CCCTCGTAGG TTTAGAGGAA ACACCCTCAT   60
AGATGAAAAC CCCCCCGAGA CAGCAGCACT GCAACTGCCA AGCAGCCGGG GTAGGAGGGG  120
CGCCCTATGC ACAGCTGGGC CCTTGAGACA GCAGGGCTTC GATGTCAGGC TCGATGTCAA  180
TGGTCTGGAA GCGGCGGCTG TACCTGCGTA GGGGCACACC GTCAGGGCCC ACCAGGAACT  240
TCTCAAAGTT CCAGGCAACN TCGTTGCGAC ACACCGGAGA CCAGGTGATN AGCTTGGGGT  300
CGGTCATAAN CGCGGTGGCG TCGTCGCTGG GAGCTGGCAG GGCCTCCCGC AGGAAGGCNA  360
ATAAAAGGTG CGCCCCCGCA CCGTTCANCT CGCACTTCTC NAANACCATG ANGTTGGGCT  420
CNAACCCACC ACCANNCCGG ACTTCCTTGA NGGAATTCCC AAATCTCTTC GNTCTTGGGC  480
TTCTNCTGAT GCCCTANCTG GTTGCCCNGN ATGCCAANCA NCCCCAANCC CCGGGGTCCT  540
AAANCACCCN CCTCCTCNTT TCATCTGGGT TNTTNTCCCC GGACCNTGGT TCCTCTCAAG  600
GGANCCCATA TCTCNACCAN TACTCACCNT NCCCCCCCNT GNNACCCANC CTTCTANNGN  660
TTCCCNCCCG NCCTCTGGCC CNTCAAANAN GCTTNCACNA CCTGGGTCTG CCTTCCCCCC  720
TNCCCTATCT GNACCCCNCN TTTGTCTCAN TNT                              753
```

(2) INFORMATION FOR SEQ ID NO: 41:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 41:

```
ACTATATCCA TCACAACAGA CATGCTTCAT CCCATAGACT TCTTGACATA GCTTCAAATG   60
AGTGAACCCA TCCTTGATTT ATATACATAT ATGTTCTCAG TATTTTGGGA GCCTTTCCAC  120
TTCTTTAAAC CTTGTTCATT ATGAACACTG AAAATAGGAA TTTGTGAAGA GTTAAAAAGT  180
TATAGCTTGT TTACGTAGTA AGTTTTTGAA GTCTACATTC AATCCAGACA CTTAGTTGAG  240
TGTTAAACTG TGATTTTTAA AAAATATCAT TTGAGAATAT TCTTTCAGAG GTATTTTCAT  300
TTTTACTTTT TGATTAATTG TGTTTTATAT ATTAGGGTAG T                     341
```

(2) INFORMATION FOR SEQ ID NO: 42:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO: 42:

```
ACTTACTGAA TTTAGTTCTG TGCTCTTCCT TATTTAGTGT TGTATCATAA ATACTTTGAT    60

GTTTCAAACA TTCTAAATAA ATAATTTTCA GTGGCTTCAT A                       101
```

(2) INFORMATION FOR SEQ ID NO: 43:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo spiens (xi) SEQUENCE DESCRIPTION: SEQ ID NO: 43:

```
ACATCTTTGT TACAGTCTAA GATGTGTTCT TAAATCACCA TTCCTTCCTG GTCCTCACCC    60

TCCAGGGTGG TCTCACACTG TAATTAGAGC TATTGAGGAG TCTTTACAGC AAATTAAGAT   120

TCAGATGCCT TGCTAAGTCT AGAGTTCTAG AGTTATGTTT CAGAAAGTCT AAGAAACCCA   180

CCTCTTGAGA GGTCAGTAAA GAGGACTTAA TATTTCATAT CTACAAAATG ACCACAGGAT   240

TGGATACAGA ACGAGAGTTA TCCTGGATAA CTCAGAGCTG AGTACCTGCC CGGGGGCCGC   300

TCGAA                                                               305
```

(2) INFORMATION FOR SEQ ID NO: 44:

(i) SEQUENCE CHARACTERISTICS:
        (A) LENGTH: 852 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 44:

```
ACATAAATAT CAGAGAAAAG TAGTCTTTGA AATATTTACG TCCAGGAGTT CTTTGTTTCT    60

GATTATTTGG TGTGTGTTTT GGTTTGTGTC CAAAGTATTG GCAGCTTCAG TTTTCATTTT   120

CTCTCCATCC TCGGGCATTC TTCCCAAATT TATATACCAG TCTTCGTCCA TCCACACGCT   180

CCAGAATTTC TCTTTTGTAG TAATATCTCA TAGCTCGGCT GAGCTTTTCA TAGGTCATGC   240

TGCTGTTGTT CTTCTTTTTA CCCCATAGCT GAGCCACTGC CTCTGATTTC AAGAACCTGA   300

AGACGCCCTC AGATCGGTCT TCCCATTTTA TTAATCCTGG GTTCTTGTCT GGGTTCAAGA   360

GGATGTCGCG GATGAATTCC CATAAGTGAG TCCCTCTCGG GTTGTGCTTT TTGGTGTGGC   420

ACTTGGCAGG GGGGTCTTGC TCCTTTTTCA TATCAGGTGA CTCTGCAACA GGAAGGTGAC   480

TGGTGGTTGT CATGGAGATC TGAGCCCGGC AGAAAGTTTT GCTGTCCAAC AAATCTACTG   540

TGCTACCATA GTTGGTGTCA TATAAATAGT TCTNGTCTTT CCAGGTGTTC ATGATGGAAG   600

GCTCAGTTTG TTCAGTCTTG ACAATGACAT TGTGTGTGGA CTGGAACAGG TCACTACTGC   660

ACTGGCCGTT CCACTTCAGA TGCTGCAAGT TGCTGTAGAG GAGNTGCCCC GCCGTCCCTG   720

CCGCCCGGGT GAACTCCTGC AAACTCATGC TGCAAAGGTG CTCGCCGTTG ATGTCGAACT   780
```

```
CNTGGAAAGG GATACAATTG GCATCCAGCT GGTTGGTGTC CAGGAGGTGA TGGAGCCACT      840

CCCACACCTG GT                                                         852
```

(2) INFORMATION FOR SEQ ID NO: 45:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 45:

```
ACAACAGACC CTTGCTCGCT AACGACCTCA TGCTCATCAA GTTGGACGAA TCCGTGTCCG       60

AGTCTGACAC CATCCGGAGC ATCAGCATTG CTTCGCAGTG CCCTACCGCG GGAACTCTT       120

GCCTCGTTTC TGGCTGGGGT CTGCTGGCGA ACGGCAGAAT GCCTACCGTG CTGCAGTGCG      180

TGAACGTGTC GGTGGTGTCT GAGGAGGTCT GCAGTAAGCT CTATGACCCG CTGT           234
```

(2) INFORMATION FOR SEQ ID NO: 46:

(i) SEQUENCE CHARACTERISTICS:
        (A) LENGTH: 590 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 46:

```
ACTTTTTATT TAAATGTTTA TAAGGCAGAT CTATGAGAAT GATAGAAAAC ATGGTGTGTA       60

ATTTGATAGC AATATTTTGG AGATTACAGA GTTTTAGTAA TTACCAATTA CACAGTTAAA      120

AAGAAGATAA TATATTCCAA GCANATACAA AATATCTAAT GAAAGATCAA GGCAGGAAAA      180

TGANTATAAC TAATTGACAA TGGAAAATCA ATTTTAATGT GAATTGCACA TTATCCTTTA      240

AAAGCTTTCA AAANAAANAA TTATTGCAGT CTANTTAATT CAAACAGTGT TAAATGGTAT      300

CAGGATAAAN AACTGAAGGG CANAAAGAAT TAATTTTCAC TTCATGTAAC NCACCCANAT      360

TTACAATGGC TTAAATGCAN GGAAAAAGCA GTGGAAGTAG GGAAGTANTC AAGGTCTTTC      420

TGGTCTCTAA TCTGCCTTAC TCTTTGGGTG TGGCTTTGAT CCTCTGGAGA CAGCTGCCAG      480

GGCTCCTGTT ATATCCACAA TCCCAGCAGC AAGATGAAGG GATGAAAAAG GACACATGCT      540

GCCTTCCTTT GAGGAGACTT CATCTCACTG GCCAACACTC AGTCACATGT                590
```

(2) INFORMATION FOR SEQ ID NO: 47:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 47:

```
ACAAGGGGGC ATAATGAAGG AGTGGGGANA GATTTTAAAG AAGGAAAAAA AACGAGGCCC      60
TGAACAGAAT TTTCCTGNAC AACGGGGCTT CAAAATAATT TTCTTGGGGA GGTTCAAGAC     120
GCTTCACTGC TTGAAACTTA AATGGATGTG GGACANAATT TTCTGTAATG ACCCTGAGGG     180
CATTACAGAC GGGACTCTGG GAGGAAGGAT AAACAGAAAG GGGACAAAGG CTAATCCCAA     240
AACATCAAAG AAAGGAAGGT GGCGTCATAC CTCCCAGCCT ACACAGTTCT CCAGGGCTCT     300
CCTCATCCCT GGAGGACGAC AGTGGAGGAA CAACTGACCA TGTCCCCAGG CTCCTGTGTG     360
CTGGCTCCTG GTCTTCAGCC CCCAGCTCTG GAAGCCCACC CTCTGCTGAT CCTGCGTGGC     420
CCACACTCCT TGAACACACA TCCCCAGGTT ATATTCCTGG ACATGGCTGA ACCTCCTATT     480
CCTACTTCCG AGATGCCTTG CTCCCTGCAG CCTGTCAAAA TCCCACTCAC CCTCCAAACC     540
ACGGCATGGA AGCCTTTCT GACTTGCCTG ATTACTCCAG CATCTTGGAA CAATCCCTGA      600
TTCCCCACTC CTTAGAGGCA AGATAGGGTG GTTAAGAGTA GGGCTGGACC ACTTGGAGCC     660
AGGCTGCTGG CTTCAAATTN TGGCTCATTT ACGAGCTATG GGACCTTGGG CAAGTNATCT     720
TCACTTCTAT GGGCNTCATT TTGTTCTACC TGCAAAATGG GGGATAATAA TAGT           774
```

(2) INFORMATION FOR SEQ ID NO: 48:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 48:

```
CANAAATTGA AATTTTATAA AAAGGCATTT TTCTCTTATA TCCATAAAAT GATATAATTT      60
TTGCAANTAT ANAAATGTGT CATAAATTAT AATGTTCCTT AATTACAGCT CAACGCAACT     120
TGGT                                                                 124
```

(2) INFORMATION FOR SEQ ID NO: 49:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 49:

```
GCCGATGCTA CTATTTTATT GCAGGAGGTG GGGGTGTTTT TATTATTCTC TCAACAGCTT      60
TGTGGCTACA GGTGGTGTCT GACTGCATNA AAAANTTTTT TACGGGTGAT TGCAAAAATT     120
TTAGGGCACC CATATCCCAA GCANTGT                                         147
```

(2) INFORMATION FOR SEQ ID NO: 50:

(i) SEQUENCE CHARACTERISTICS:
        (A) LENGTH: 107 base pairs
        (B) TYPE: nucleic acid
        (C) STRANDEDNESS: single (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 50:

ACATTAAATT AATAAAAGGA CTGTTGGGGT TCTGCTAAAA CACATGGCTT GATATATTGC      60

ATGGTTTGAG GTTAGGAGGA GTTAGGCATA TGTTTTGGGA GAGGGGT                  107

(2) INFORMATION FOR SEQ ID NO: 51:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 51:

GTCCTAGGAA GTCTAGGGGA CACACGACTC TGGGGTCACG GGGCCGACAC ACTTGCACGG      60

CGGGAAGGAA AGGCAGAGAA GTGACACCGT CAGGGGAAA TGACAGAAAG GAAAATCAAG      120

GCCTTGCAAG GTCAGAAAGG GGACTCAGGG CTTCCACCAC AGCCCTGCCC CACTTGGCCA     180

CCTCCCTTTT GGGACCAGCA ATGT                                           204

(2) INFORMATION FOR SEQ ID NO: 52:

(i) SEQUENCE CHARACTERISTICS:
        (A) LENGTH: 491 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 52:

ACAAAGATAA CATTTATCTT ATAACAAAAA TTTGATAGTT TTAAAGGTTA GTATTGTGTA      60

GGGTATTTTC CAAAAGACTA AAGAGATAAC TCAGGTAAAA AGTTAGAAAT GTATAAAACA    120

CCATCAGACA GGTTTTTAAA AAACAACATA TTACAAAATT AGACAATCAT CCTTAAAAAA    180

AAAACTTCTT GTATCAATTT CTTTTGTTCA AAATGACTGA CTTAANTATT TTTAAATATT    240

TCANAAACAC TTCCTCAAAA ATTTTCAANA TGGTAGCTTT CANATGTNCC CTCAGTCCCA    300

ATGTTGCTCA GATAAATAAA TCTCGTGAGA ACTTACCACC CACCACAAGC TTTCTGGGGC    360

ATGCAACAGT GTCTTTTCTT TNCTTTTTCT TTTTTTTTTT TTACAGGCAC AGAAACTCAT    420

CAATTTTATT TGGATAACAA AGGGTCTCCA AATTATATTG AAAAATAAAT CCAAGTTAAT    480

ATCACTCTTG T                                                         491

(2) INFORMATION FOR SEQ ID NO: 53:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO: 53:

| | | | | | |
|---|---|---|---|---|---|
| ACATAATTTA | GCAGGGCTAA | TTACCATAAG | ATGCTATTTA | TTAANAGGTN | TATGATCTGA | 60 |
| GTATTAACAG | TTGCTGAAGT | TTGGTATTTT | TATGCAGCAT | TTTCTTTTTG | CTTTGATAAC | 120 |
| ACTACAGAAC | CCTTAAGGAC | ACTGAAAATT | AGTAAGTAAA | GTTCAGAAAC | ATTAGCTGCT | 180 |
| CAATCAAATC | TCTACATAAC | ACTATAGTAA | TTAAAACGTT | AAAAAAAAGT | GTTGAAATCT | 240 |
| GCACTAGTAT | ANACCGCTCC | TGTCAGGATA | ANACTGCTTT | GGAACAGAAA | GGGAAAAANC | 300 |
| AGCTTTGANT | TTCTTTGTGC | TGATANGAGG | AAAGGCTGAA | TTACCTTGTT | GCCTCTCCCT | 360 |
| AATGATTGGC | AGGTCNGGTA | AATNCCAAAA | CATATTCCAA | CTCAACACTT | CTTTTCCNCG | 420 |
| TANCTTGANT | CTGTGTATTC | CAGGANCAGG | CGGATGGAAT | GGGCCAGCCC | NCGGATGTTC | 480 |
| CANT | | | | | | 484 |

(2) INFORMATION FOR SEQ ID NO: 54:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 54:

ACTAAACCTC GTGCTTGTGA ACTCCATACA GAAAACGGTG CCATCCCTGA ACACGGCTGG    60

CCACTGGGTA TACTGCTGAC AACCGCAACA ACAAAAACAC AAATCCTTGG CACTGGCTAG    120

TCTATGTCCT CTCAAGTGCC TTTTTGTTTG T                                   151

(2) INFORMATION FOR SEQ ID NO: 55:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 55:

ACCTGGCTTG TCTCCGGGTG GTTCCCGGCG CCCCCCACGG TCCCCAGAAC GGACACTTTC    60

GCCCTCCAGT GGATACTCGA GCCAAAGTGG T                                   91

(2) INFORMATION FOR SEQ ID NO: 56:

(i) SEQUENCE CHARACTERISTICS:
        (A) LENGTH: 133 base pairs
        (B) TYPE: nucleic acid
        (C) STRANDEDNESS: single
        (D) TOPOLOGY: linear (ii) MOLECULE TYPE: cDNA

```
    (vi) ORIGINAL SOURCE:
         (A) ORGANISM: Homo sapiens (xi) SEQUENCE DESCRIPTION: SEQ ID NO: 56:

GGCGGATGTG CGTTGGTTAT ATACAAATAT GTCATTTTAT GTAAGGGACT TGAGTATACT      60

TGGATTTTTG GTATCTGTGG GTTGGGGGGA CGGTCCAGGA ACCAATACCC CATGGATACC     120

AAGGGACAAC TGT                                                       133

(2) INFORMATION FOR SEQ ID NO: 57:

(i) SEQUENCE CHARACTERISTICS:
         (A) LENGTH: 147 base pairs
         (B) TYPE: nucleic acid
         (C) STRANDEDNESS: single
         (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 57:

ACTCTGGAGA ACCTGAGCCG CTGCTCCGCC TCTGGGATGA GGTGATGCAN GCNGTGGCGC      60

GACTGGGAGC TGAGCCCTTC CCTTTGCGCC TGCCTCAGAG GATTGTTGCC GACNTGCANA    120

TCTCANTGGG CTGGATNCAT GCAGGGT                                        147

(2) INFORMATION FOR SEQ ID NO: 58:

(i) SEQUENCE CHARACTERISTICS:
         (A) LENGTH: 198 base pairs
         (B) TYPE: nucleic acid
         (C) STRANDEDNESS: single
         (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 58:

ACAGGGATAT AGGTTTNAAG TTATTGTNAT TGTAAAATAC ATTGAATTTT CTGTATACTC      60

TGATTACATA CATTTATCCT TTAAAAAAGA TGTAAATCTT AATTTTTATG CCATCTATTA    120

ATTTACCAAT GAGTTACCTT GTAAATGAGA AGTCATGATA GCACTGAATT TTAACTAGTT    180

TTGACTTCTA AGTTTGGT                                                  198

(2) INFORMATION FOR SEQ ID NO: 59:

(i) SEQUENCE CHARACTERISTICS:
         (A) LENGTH: 330 base pairs
         (B) TYPE: nucleic acid
         (C) STRANDEDNESS: single
         (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 59:

ACAACAAATG GGTTGTGAGG AAGTCTTATC AGCAAAACTG GTGATGGCTA CTGAAAAGAT      60

CCATTGAAAA TTATCATTAA TGATTTTAAA TGACAAGTTA TCAAAAACTC ACTCAATTTT    120

CACCTGTGCT AGCTTGCTAA AATGGGAGTT AACTCTAGAG CAAATATAGT ATCTTCTGAA    180
```

TACAGTCAAT AAATGACAAA GCCAGGGCCT ACAGGTGGTT TCCAGACTTT CCAGACCCAG    240

CAGAAGGAAT CTATTTTATC ACATGGATCT CCGTCTGTGC TCAAAATACC TAATGATATT    300

TTTCGTCTTT ATTGGACTTC TTTGAAGAGT                                    330

(2) INFORMATION FOR SEQ ID NO: 60:

(i) SEQUENCE CHARACTERISTICS:
        (A) LENGTH: 175 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 60:

ACCGTGGGTG CCTTCTACAT TCCTGACGGC TCCTTCACCA ACATCTGGTT CTACTTCGGC     60

GTCGTGGGCT CCTTCCTCTT CATCCTCATC CAGCTGGTGC TGCTCATCGA CTTTGCGCAC    120

TCCTGGAACC AGCGGTGGCT GGGCAAGGCC GAGGAGTGCG ATTCCCGTGC CTGGT         175

(2) INFORMATION FOR SEQ ID NO: 61:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 61:

ACCCCACTTT TCCTCCTGTG AGCAGTCTGG ACTTCTCACT GCTACATGAT GAGGGTGAGT     60

GGTTGTTGCT CTTCAACAGT ATCCTCCCCT TTCCGGATCT GCTGAGCCGG ACAGCAGTGC    120

TGGACTGCAC AGCCCCGGGG CTCCACATTG CTGT                                154

(2) INFORMATION FOR SEQ ID NO: 62:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 62:

CGCTCGAGCC CTATAGTGAG TCGTATTAGA                                     30

(2) INFORMATION FOR SEQ ID NO: 63:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 63:

ACAAGTCATT TCAGCACCCT TGCTCTTCA AAACTGACCA TCTTTTATAT TTAATGCTTC      60

CTGTATGAAT AAAAATGGTT ATGTCAAGT                                      89

(2) INFORMATION FOR SEQ ID NO: 64:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 64:

ACCGGAGTAA CTGAGTCGGG ACGCTGAATC TGAATCCACC AATAAATAAA GGTTCTGCAG     60

AATCAGTGCA TCCAGGATTG GTCCTTGGAT CTGGGGT                              97

(2) INFORMATION FOR SEQ ID NO: 65:

(i) SEQUENCE CHARACTERISTICS:
        (A) LENGTH: 377 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 65:

ACAACAANAA NTCCCTTCTT TAGGCCACTG ATGGAAACCT GGAACCCCCT TTTGATGGCA     60

GCATGGCGTC CTAGGCCTTG ACACAGCGGC TGGGGTTTGG GCTNTCCCAA ACCGCACACC    120

CCAACCCTGG TCTACCCACA NTTCTGGCTA TGGGCTGTCT CTGCCACTGA ACATCAGGGT   180

TCGGTCATAA NATGAAATCC CAANGGGGAC AGAGGTCAGT AGAGGAAGCT CAATGAGAAA   240

GGTGCTGTTT GCTCAGCCAG AAAACAGCTG CCTGGCATTC GCCGCTGAAC TATGAACCCG   300

TGGGGGTGAA CTACCCCCAN GAGGAATCAT GCCTGGGCGA TGCAANGGTG CCAACAGGAG   360

GGGCGGGAGG AGCATGT                                                  377

(2) INFORMATION FOR SEQ ID NO: 66:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 66:

ACGCCTTTCC CTCAGAATTC AGGGAAGAGA CTGTCGCCTG CCTTCCTCCG TTGTTGCGTG    60

AGAACCCGTG TGCCCCTTCC CACCATATCC ACCCTCGCTC CATCTTTGAA CTCAAACACG   120

```
AGGAACTAAC TGCACCCTGG TCCTCTCCCC AGTCCCCAGT TCACCCTCCA TCCCTCACCT        180

TCCTCCACTC TAAGGGATAT CAACACTGCC CAGCACAGGG GCCCTGAATT TATGTGGTTT        240

TTATATATTT TTTAATAAGA TGCACTTTAT GTCATTTTTT AATAAAGTCT GAAGAATTAC        300

TGTTT                                                                   305

(2) INFORMATION FOR SEQ ID NO: 67:

(i) SEQUENCE CHARACTERISTICS:
        (A) LENGTH: 385 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 67:

ACTACACACA CTCCACTTGC CCTTGTGAGA CACTTTGTCC CAGCACTTTA GGAATGCTGA         60

GGTCGGACCA GCCACATCTC ATGTGCAAGA TTGCCCAGCA GACATCAGGT CTGAGAGTTC        120

CCCTTTTAAA AAGGGGACT TGCTTAAAAA AGAAGTCTAG CCACGATTGT GTAGAGCAGC         180

TGTGCTGTGC TGGAGATTCA CTTTTGAGAG AGTTCTCCTC TGAGACCTGA TCTTTAGAGG        240

CTGGGCAGTC TTGCACATGA GATGGGGCTG GTCTGATCTC AGCACTCCTT AGTCTGCTTG        300

CCTCTCCCAG GGCCCCAGCC TGGCCACACC TGCTTACAGG GCACTCTCAG ATGCCCATAC        360

CATAGTTTCT GTGCTAGTGG ACCGT                                             385

(2) INFORMATION FOR SEQ ID NO: 68:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 68:

ACTTAACCAG ATATATTTTT ACCCCAGATG GGGATATTCT TTGTAAAAAA TGAAAATAAA         60

GTTTTTTTAA TGG                                                           73

(2) INFORMATION FOR SEQ ID NO: 69:

(i) SEQUENCE CHARACTERISTICS:
        (A) LENGTH: 536 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 69:

ACTAGTCCAG TGTGGTGGAA TTCCATTGTG TTGGGGGCTC TCACCCTCCT CTCCTGCAGC         60

TCCAGCTTTG TGCTCTGCCT CTGAGGAGAC CATGGCCCAG CATCTGAGTA CCCTGCTGCT        120

CCTGCTGGCC ACCCTAGCTG TGGCCCTGGC CTGGAGCCCC AAGGAGGAGG ATAGGATAAT        180
```

```
CCCGGGTGGC ATCTATAACG CAGACCTCAA TGATGAGTGG GTACAGCGTG CCCTTCACTT        240

CGCCATCAGC GAGTATAACA AGGCCACCAA AGATGACTAC TACAGACGTC CGCTGCGGGT        300

ACTAAGAGCC AGGCAACAGA CCGTTGGGGG GGTGAATTAC TTCTTCGACG TAGAGGTGGG        360

CCGAACCATA TGTACCAAGT CCCAGCCCAA CTTGGACACC TGTGCCTTCC ATGAACAGCC        420

AGAACTGCAG AAGAAACAGT TGTGCTCTTT CGAGATCTAC GAAGTTCCCT GGGGAGAACA        480

GAANGTCCCT GGGTGAAATC CAGGTGTCAA GAAATCCTAN GGATCTGTTG CCAGGC           536

(2) INFORMATION FOR SEQ ID NO: 70:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 70:

ATGACCCCTA ACAGGGGCCC TCTCAGCCCT CCTAATGACC TCCGGCCTAG CCATGTGATT         60

TCACTTCCAC TCCATAACGC TCCTCATACT AGGCCTACTA ACCAACACAC TAACCATATA        120

CCAATGATGG CGCGATGTAA CACGAGAAAG CACATACCAA GGCCACCACA CACCACCTGT        180

CCAAAAAGGC CTTCGATACG GGATAATCCT ATTTATTACC TCAGAAGTTT TTTTCTTCGC        240

AGGGATTTTT CTGAGCCTTT TACCACTCCA GCCTAGCCCC TACCCCCCAA CTAGGAGGGC        300

ACTGGCCCCC AACAGGCATC ACCCCGCTAA ATCCCCTAGA AGTCCCACTC CTAAACACAT        360

CCGTATTACT CGCATCAGGA GTATCAATCA CCTGAGCTCA CCATAGTCTA ATAGAAAACA        420

ACCGAAACCA AATTATTCAA AGCACTGCTT ATTACAATTT TACTGGGTCT CTATTTT          477

(2) INFORMATION FOR SEQ ID NO: 71:

(i) SEQUENCE CHARACTERISTICS:
        (A) LENGTH: 533 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 71:

AGAGCTATAG GTACAGTGTG ATCTCAGCTT TGCAAACACA TTTTCTACAT AGATAGTACT         60

AGGTATTAAT AGATATGTAA AGAAAGAAAT CACACCATTA ATAATGGTAA GATTGGTTTA        120

TGTGATTTTA GTGGTATTTT TGGCACCCTT ATATATGTTT CCAAACTTT CAGCAGTGAT         180

ATTATTTCCA TAACTTAAAA AGTGAGTTTG AAAAAGAAAA TCTCCAGCAA GCATCTCATT        240

TAAATAAAGG TTTGTCATCT TTAAAAATAC AGCAATATGT GACTTTTTAA AAAAGCTGTC        300

AAATAGGTGT GACCCTACTA ATAATTATTA GAAATACATT TAAAAACATC GAGTACCTCA        360

AGTCAGTTTG CCTTGAAAAA TATCAAATAT AACTCTTAGA GAAATGTACA TAAAAGAATG        420

CTTCGTAATT TTGGAGTANG AGGTTCCCTC CTCAATTTTG TATTTTTAAA AGTACATGG         480

TAAAAAAAAA AATTCACAAC AGTATATAAG GCTGTAAAAT GAAGAATTCT GCC               533
```

(2) INFORMATION FOR SEQ ID NO: 72:

(i) SEQUENCE CHARACTERISTICS:
        (A) LENGTH: 511 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 72:

```
TATTACGGAA AAACACACCA CATAATTCAA CTANCAAAGA ANACTGCTTC AGGGCGTGTA      60

AAATGAAAGG CTTCCAGGCA GTTATCTGAT TAAAGAACAC TAAAAGAGGG ACAAGGCTAA     120

AAGCCGCAGG ATGTCTACAC TATANCAGGC GCTATTTGGG TTGGCTGGAG GAGCTGTGGA     180

AAACATGGAN AGATTGGTGC TGGANATCGC CGTGGCTATT CCTCATTGTT ATTACANAGT     240

GAGGTTCTCT GTGTGCCCAC TGGTTTGAAA ACCGTTCTNC AATAATGATA GAATAGTACA     300

CACATGAGAA CTGAAATGGC CCAAACCCAG AAAGAAAGCC CAACTAGATC CTCAGAANAC     360

GCTTCTAGGG ACAATAACCG ATGAAGAAAA GATGGCCTCC TTGTGCCCCC GTCTGTTATG     420

ATTTCTCTCC ATTGCAGCNA NAAACCCGTT CTTCTAAGCA AACNCAGGTG ATGATGGCNA     480

AAATACACCC CCTCTTGAAG NACCNGGAGG A                                    511
```

(2) INFORMATION FOR SEQ ID NO: 73:

(i) SEQUENCE CHARACTERISTICS:
        (A) LENGTH: 499 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 73:

```
CAGTGCCAGC ACTGGTGCCA GTACCAGTAC CAATAACAGT GCCAGTGCCA GTGCCAGCAC      60

CAGTGGTGGC TTCAGTGCTG GTGCCAGCCT GACCGCCACT CTCACATTTG GGCTCTTCGC     120

TGGCCTTGGT GGAGCTGGTG CCAGCACCAG TGGCAGCTCT GGTGCCTGTG GTTTCTCCTA     180

CAAGTGAGAT TTTAGATATT GTTAATCCTG CCAGTCTTTC TCTTCAAGCC AGGGTGCATC     240

CTCAGAAACC TACTCAACAC AGCACTCTAG GCAGCCACTA TCAATCAATT GAAGTTGACA     300

CTCTGCATTA AATCTATTTG CCATTTCTGA AAAAAAAAAA AAAAAAAGGG CGGCCGCTCG     360

ANTCTAGAGG GCCCGTTTAA ACCCGCTGAT CAGCCTCGAC TGTGCCTTCT ANTTGCCAGC     420

CATCTGTTGT TTGCCCCTCC CCCGNTGCCT TCCTTGACCC TGGAAAGTGC CACTCCCACT     480

GTCCTTTCCT AANTAAAAT                                                  499
```

(2) INFORMATION FOR SEQ ID NO: 74:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 74:

```
TTTCATAGGA GAACACACTG AGGAGATACT TGAAGAATTT GGATTCAGCC GCGAAGAGAT      60

TTATCAGCTT AACTCAGATA AAATCATTGA AAGTAATAAG GTAAAAGCTA GTCTCTAACT     120

TCCAGGCCCA CGGCTCAAGT GAATTTGAAT ACTGCATTTA CAGTGTAGAG TAACACATAA     180

CATTGTATGC ATGGAAACAT GGAGGAACAG TATTACAGTG TCCTACCACT CTAATCAAGA     240

AAAGAATTAC AGACTCTGAT TCTACAGTGA TGATTGAATT CTAAAAATGG TAATCATTAG     300

GGCTTTTGAT TTATAANACT TTGGGTACTT ATACTAAATT ATGGTAGTTA TACTGCCTTC     360

CAGTTTGCTT GATATATTTG TTGATATTAA GATTCTTGAC TTATATTTTG AATGGGTTCT     420

ACTGAAAAAN GAATGATATA TTCTTGAAGA CATCGATATA CATTTATTTA CACTCTTGAT     480

TCTACAATGT AGAAAATGAA GGAAATGCCC CAAATTGTAT GGTGATAAAA GTCCCGT       537
```

(2) INFORMATION FOR SEQ ID NO: 75:

(i) SEQUENCE CHARACTERISTICS:
        (A) LENGTH: 467 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 75:

```
CAAANACAAT TGTTCAAAAG ATGCAAATGA TACACTACTG CTGCAGCTCA CAAACACCTC      60

TGCATATTAC ACGTACCTCC TCCTGCTCCT CAAGTAGTGT GGTCTATTTT GCCATCATCA     120

CCTGCTGTCT GCTTAGAAGA ACGGCTTTCT GCTGCAANGG AGAGAAATCA TAACAGACGG     180

TGGCACAAGG AGGCCATCTT TTCCTCATCG GTTATTGTCC CTAGAAGCGT CTTCTGAGGA     240

TCTAGTTGGG CTTTCTTTCT GGGTTTGGGC CATTTCANTT CTCATGTGTG TACTATTCTA     300

TCATTATTGT ATAACGGTTT TCAAACCNGT GGGCACNCAG AGAACCTCAC TCTGTAATAA     360

CAATGAGGAA TAGCCACGGT GATCTCCAGC ACCAAATCTC TCCATGTTNT TCCAGAGCTC     420

CTCCAGCCAA CCCAAATAGC CGCTGCTATN GTGTAGAACA TCCCTGN                  467
```

(2) INFORMATION FOR SEQ ID NO: 76:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 76:

```
AAGCTGACAG CATTCGGGCC GAGATGTCTC GCTCCGTGGC CTTAGCTGTG CTCGCGCTAC      60

TCTCTCTTTC TGGCCTGGAG GCTATCCAGC GTACTCCAAA GATTCAGGTT TACTCACGTC     120

ATCCAGCAGA GAATGGAAAG TCAAATTTCC TGAATTGCTA TGTGTCTGGG TTTCATCCAT     180

CCGACATTGA AGTTGACTTA CTGAAGAATG GAGAGAGAAT TGAAAAAGTG GAGCATTCAG     240
```

```
ACTTGTCTTT CAGCAAGGAC TGGTCTTTCT ATCTCTTGTA CTACACTGAA TTCACCCCCA      300

CTGAAAAAGA TGAGTATGCC TGCCGTGTGA ACCATGTGAC TTTGTCACAG CCCAAGATNG      360

TTNAGTGGGA TCGANACATG TAAGCAGCAN CATGGGAGGT                            400

(2) INFORMATION FOR SEQ ID NO: 77:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo Sapiens (xi) SEQUENCE DESCRIPTION: SEQ ID NO: 77:

CTGGAGTGCC TTGGTGTTTC AAGCCCCTGC AGGAAGCAGA ATGCACCTTC TGAGGCACCT       60

CCAGCTGCCC CGGCGGGGGA TGCGAGGCTC GGAGCACCCT TGCCCGGCTG TGATTGCTGC      120

CAGGCACTGT TCATCTCAGC TTTTCTGTCC CTTTGCTCCC GGCAAGCGCT TCTGCTGAAA      180

GTTCATATCT GGAGCCTGAT GTCTTAACGA ATAAAGGTCC CATGCTCCAC CCGAAAAAAA      240

AAAAAAAA                                                              248

(2) INFORMATION FOR SEQ ID NO: 78:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 78:

ACTAGTCCAG TGTGGTGGAA TTCCATTGTG TTGGGCCCAA CACAATGGCT ACCTTTAACA       60

TCACCCAGAC CCCGCCCTGC CCGTGCCCCA CGCTGCTGCT AACGACAGTA TGATGCTTAC      120

TCTGCTACTC GGAAACTATT TTTATGTAAT TAATGTATGC TTTCTTGTTT ATAAATGCCT      180

GATTTAAAAA AAAAAAAAA A                                                201

(2) INFORMATION FOR SEQ ID NO: 79:

(i) SEQUENCE CHARACTERISTICS:
        (A) LENGTH: 552 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 79:

TCCTTTTGTT AGGTTTTTGA GACAACCCTA GACCTAAACT GTGTCACAGA CTTCTGAATG       60

TTTAGGCAGT GCTAGTAATT TCCTCGTAAT GATTCTGTTA TTACTTTCCT ATTCTTTATT      120

CCTCTTTCTT CTGAAGATTA ATGAAGTTGA AAATTGAGGT GGATAAATAC AAAAAGGTAG      180

TGTGATAGTA TAAGTATCTA AGTGCAGATG AAAGTGTGTT ATATATATCC ATTCAAAATT      240
```

```
ATGCAAGTTA GTAATTACTC AGGGTTAACT AAATTACTTT AATATGCTGT TGAACCTACT      300

CTGTTCCTTG GCTAGAAAAA ATTATAAACA GGACTTTGTT AGTTTGGGAA GCCAAATTGA      360

TAATATTCTA TGTTCTAAAA GTTGGGCTAT ACATAAANTA TNAAGAAATA TGGAATTTTA      420

TTCCCAGGAA TATGGGGTTC ATTTATGAAT ANTACCCGGG ANAGAAGTTT TGANTNAAAC      480

CNGTTTTGGT TAATACGTTA ATATGTCCTN AATNAACAAG GCNTGACTTA TTTCCAAAAA      540

AAAAAAAAAA AA                                                          552

(2) INFORMATION FOR SEQ ID NO: 80:

(i) SEQUENCE CHARACTERISTICS:
        (A) LENGTH: 476 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 80:

ACAGGGATTT GAGATGCTAA GGCCCCAGAG ATCGTTTGAT CCAACCCTCT TATTTTCAGA       60

GGGGAAAATG GGGCCTAGAA GTTACAGAGC ATCTAGCTGG TGCGCTGGCA CCCCTGGCCT      120

CACACAGACT CCCGAGTAGC TGGGACTACA GGCACACAGT CACTGAAGCA GGCCCTGTTT      180

GCAATTCACG TTGCCACCTC CAACTTAAAC ATTCTTCATA TGTGATGTCC TTAGTCACTA      240

AGGTAAAACT TTCCCACCCA GAAAAGGCAA CTTAGATAAA ATCTTAGAGT ACTTTCATAC      300

TCTTCTAAGT CCTCTTCCAG CCTCACTTTG AGTCCTCCTT GGGGGTTGAT AGGAANTNTC      360

TCTTGGCTTT CTCAATAAAA TCTCTATCCA TCTCATGTTT AATTTGGTAC GCNTAAAAAT      420

GCTGAAAAAA TTAAAATGTT CTGGTTTCNC TTTAAAAAAA AAAAAAAAA AAAAAA          476

(2) INFORMATION FOR SEQ ID NO: 81:

(i) SEQUENCE CHARACTERISTICS:
        (A) LENGTH: 232 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 81:

TTTTTTTTTG TATGCCNTCN CTGTGGNGTT ATTGTTGCTG CCACCCTGGA GGAGCCCAGT       60

TTCTTCTGTA TCTTTCTTTT CTGGGGGATC TTCCTGGCTC TGCCCCTCCA TTCCCAGCCT      120

CTCATCCCCA TCTTGCACTT TTGCTAGGGT TGGAGGCGCT TTCCTGGTAG CCCCTCAGAG      180

ACTCAGTCAG CGGGAATAAG TCCTAGGGGT GGGGGGTGTG GCAAGCCGGC CT             232

(2) INFORMATION FOR SEQ ID NO: 82:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (ii) MOLECULE TYPE: cDNA
```

(vi) ORIGINAL SOURCE:
              (A) ORGANISM: Homo sapiens (xi) SEQUENCE DESCRIPTION: SEQ ID NO: 82:

| | | | | | |
|---|---|---|---|---|---|
| AGGCGGGAGC | AGAAGCTAAA | GCCAAAGCCC | AAGAAGAGTG | GCAGTGCCAG | CACTGGTGCC | 60 |
| AGTACCAGTA | CCAATAACAT | GCCAGTGCCA | GTGCCAGCAC | CAGTGGTGGC | TTCAGTGCTG | 120 |
| GTGCCAGCCT | GACCGCCACT | CTCACATTTG | GGCTCTTCGC | TGGCCTTGGT | GGAGCTGGTG | 180 |
| CCAGCACCAG | TGGCAGCTCT | GGTGCCTGTG | GTTTCTCCTA | CAAGTGAGAT | TTTAGATATT | 240 |
| GTTAATCCTG | CCAGTCTTTC | TCTTCAAGCC | AGGGTGCATC | CTCAGAAACC | TACTCAACAC | 300 |
| AGCACTCTNG | GCAGCCACTA | TCAATCAATT | GAAGTTGACA | CTCTGCATTA | AATCTATTTG | 360 |
| CCATTTCAAA | AAAAAAAAAA | AAA | | | | 383 |

(2) INFORMATION FOR SEQ ID NO: 83:

(i) SEQUENCE CHARACTERISTICS:
              (A) LENGTH: 494 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: Homo sapiens (xi) SEQUENCE DESCRIPTION: SEQ ID NO: 83:

| | | | | | |
|---|---|---|---|---|---|
| ACCGAATTGG | GACCGCTGGC | TTATAAGCGA | TCATGTCCTC | CAGTATTACC | TCAACGAGCA | 60 |
| GGGAGATCGA | GTCTATACGC | TGAAGAAATT | TGACCCGATG | GGACAACAGA | CCTGCTCAGC | 120 |
| CCATCCTGCT | CGGTTCTCCC | CAGATGACAA | ATACTCTCGA | CACCGAATCA | CCATCAAGAA | 180 |
| ACGCTTCAAG | GTGCTCATGA | CCCAGCAACC | GCGCCCTGTC | CTCTGAGGGT | CCTTAAACTG | 240 |
| ATGTCTTTTC | TGCCACCTGT | TACCCCTCGG | AGACTCCGTA | ACCAAACTCT | TCGGACTGTG | 300 |
| AGCCCTGATG | CCTTTTTGCC | AGCCATACTC | TTTGGCNTCC | AGTCTCTCGT | GGCGATTGAT | 360 |
| TATGCTTGTG | TGAGGCAATC | ATGGTGGCAT | CACCCATNAA | GGGAACACAT | TTGANTTTTT | 420 |
| TTTCNCATAT | TTTAAATTAC | NACCAGAATA | NTTCAGAATA | AATGAATTGA | AAAACTCTTA | 480 |
| AAAAAAAAAA | AAAA | | | | | 494 |

(2) INFORMATION FOR SEQ ID NO: 84:

(i) SEQUENCE CHARACTERISTICS:
              (A) LENGTH: 380 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: Homo sapiens (xi) SEQUENCE DESCRIPTION: SEQ ID NO:84:

| | | | | | |
|---|---|---|---|---|---|
| GCTGGTAGCC | TATGGCGTGG | CCACGGANGG | GCTCCTGAGG | CACGGACAG | TGACTTCCCA | 60 |
| AGTATCCTGC | GCCGCGTCTT | CTACCGTCCC | TACCTGCAGA | TCTTCGGGCA | GATTCCCCAG | 120 |
| GAGGACATGG | ACGTGGCCCT | CATGGAGCAC | AGCAACTGCT | CGTCGGAGCC | CGGCTTCTGG | 180 |
| GCACACCCTC | CTGGGGCCCA | GGCGGGCACC | TGCGTCTCCC | AGTATGCCAA | CTGGCTGGTG | 240 |
| GTGCTGCTCC | TCGTCATCTT | CCTGCTCGTG | GCCAACATCC | TGCTGGTCAC | TTGCTCATTG | 300 |

```
CCATGTTCAG TTACACATTC GGCAAAGTAC AGGGCAACAG CNATCTCTAC TGGGAAGGCC    360

AGCGTTNCCG CCTCATCCGG                                                380

(2) INFORMATION FOR SEQ ID NO: 85:

(i) SEQUENCE CHARACTERISTICS:
        (A) LENGTH: 481 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 85:

GAGTTAGCTC CTCCACAACC TTGATGAGGT CGTCTGCAGT GGCCTCTCGC TTCATACCGC     60

TNCCATCGTC ATACTGTAGG TTTGCCACCA CCTCCTGCAT CTTGGGGCGG CTAATATCCA    120

GGAAACTCTC AATCAAGTCA CCGTCNATNA AACCTGTGGC TGGTTCTGTC TTCCGCTCGG    180

TGTGAAAGGA TCTCCAGAAG GAGTGCTCGA TCTTCCCCAC ACTTTTGATG ACTTTATTGA    240

GTCGATTCTG CATGTCCAGC AGGAGGTTGT ACCAGCTCTC TGACAGTGAG GTCACCAGCC    300

CTATCATGCC NTTGAACGTG CCGAAGAACA CCGAGCCTTG TGTGGGGGT GNAGTCTCAC     360

CCAGATTCTG CATTACCAGA NAGCCGTGGC AAAAGANATT GACAACTCGC CCAGGNNGAA    420

AAAGAACACC TCCTGGAAGT GCTNGCCGCT CCTCGTCCNT TGGTGGNNGC GCNTNCCTTT    480

T                                                                    481

(2) INFORMATION FOR SEQ ID NO: 86:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 86:

AACATCTTCC TGTATAATGC TGTGTAATAT CGATCCGATN TTGTCTGCTG AGAATTCATT     60

ACTTGGAAAA GCAACTTNAA GCCTGGACAC TGGTATTAAA ATTCACAATA TGCAACACTT    120

TAAACAGTGT GTCAATCTGC TCCCTTACTT TGTCATCACC AGTCTGGGAA TAAGGGTATG    180

CCCTATTCAC ACCTGTTAAA AGGGCGCTAA GCATTTTTGA TTCAACATCT TTTTTTTTGA    240

CACAAGTCCG AAAAAAGCAA AAGTAAACAG TTNTTAATTT GTTAGCCAAT TCACTTTCTT    300

CATGGGACAG AGCCATTTGA TTTAAAAAGC AAATTGCATA ATATTGAGCT TGGGAGCTG     360

ATATNTGAGC GGAAGANTAG CCTTTCTACT TCACCAGACA CAACTCCTTT CATATTGGGA    420

TGTTNACNAA AGTTATGTCT CTTACAGATG GGATGCTTTT GTGGCAATTC TG            472

(2) INFORMATION FOR SEQ ID NO: 87:

(i) SEQUENCE CHARACTERISTICS:
        (A) LENGTH: 413 base pairs
        (B) TYPE: nucleic acid
        (C) STRANDEDNESS: single
        (D) TOPOLOGY: linear
```

(ii) MOLECULE TYPE: cDNA (vi) ORIGINAL SOURCE:
        (A) ORGANISM: Homo sapiens (xi) SEQUENCE DESCRIPTION: SEQ ID NO: 87:

| | | | | | |
|---|---|---|---|---|---|
| AGAAACCAGT | ATCTCTNAAA | ACAACCTCTC | ATACCTTGTG | GACCTAATTT | TGTGTGCGTG | 60 |
| TGTGTGTGCG | CGCATATTAT | ATAGACAGGC | ACATCTTTTT | TACTTTTGTA | AAAGCTTATG | 120 |
| CCTCTTTGGT | ATCTATATCT | GTGAAAGTTT | TAATGATCTG | CCATAATGTC | TTGGGGACCT | 180 |
| TTGTCTTCTG | TGTAAATGGT | ACTAGAGAAA | ACACCTATNT | TATGAGTCAA | TCTAGTTNGT | 240 |
| TTTATTCGAC | ATGAAGGAAA | TTTCCAGATN | ACAACACTNA | CAAACTCTCC | CTTGACTAGG | 300 |
| GGGGACAAAG | AAAAGCANAA | CTGAACATNA | GAAACAATTN | CCTGGTGAGA | AATTNCATAA | 360 |
| ACAGAAATTG | GGTNGTATAT | TGAAANANNG | CATCATTNAA | ACGTTTTTTT | TTT | 413 |

(2) INFORMATION FOR SEQ ID NO: 88:

(i) SEQUENCE CHARACTERISTICS:
        (A) LENGTH: 448 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 88:

| | | | | | |
|---|---|---|---|---|---|
| CGCAGCGGGT | CCTCTCTATC | TAGCTCCAGC | CTCTCGCCTG | CCCCACTCCC | CGCGTCCCGC | 60 |
| GTCCTAGCCN | ACCATGGCCG | GGCCCCTGCG | CGCCCCGCTG | CTCCTGCTGG | CCATCCTGGC | 120 |
| CGTGGCCCTG | GCCGTGAGCC | CCGCGGCCGG | CTCCAGTCCC | GGCAAGCCGC | CGCGCCTGGT | 180 |
| GGGAGGCCCA | TGGACCCCGC | GTGGAAGAAG | AAGGTGTGCG | GCGTGCACTG | GACTTTGCCG | 240 |
| TCGGCNANTA | CAACAAACCC | GCAACNACTT | TTACCNAGCN | CGCGCTGCAG | GTTGTGCCGC | 300 |
| CCCAANCAAA | TTGTTACTNG | GGGTAANTAA | TTCTTGGAAG | TTGAACCTGG | GCCAAACNNG | 360 |
| TTTACCAGAA | CCNAGCCAAT | TNGAACAATT | NCCCCTCCAT | AACAGCCCCT | TTTAAAAAGG | 420 |
| GAANCANTCC | TGNTCTTTTC | CAAATTTT | | | | 448 |

(2) INFORMATION FOR SEQ ID NO: 89:

(i) SEQUENCE CHARACTERISTICS:
        (A) LENGTH: 463 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 89:

| | | | | | |
|---|---|---|---|---|---|
| GAATTTGTG | CACTGGCCAC | TGTGATGGAA | CCATTGGGCC | AGGATGCTTT | GAGTTTATCA | 60 |
| GTAGTGATTC | TGCCAAAGTT | GGTGTTGTAA | CATGAGTATG | TAAAATGTCA | AAAAATTAGC | 120 |
| AGAGGTCTAG | GTCTGCATAT | CAGCAGACAG | TTTGTCCGTG | TATTTTGTAG | CCTTGAAGTT | 180 |
| CTCAGTGACA | AGTTNNTTCT | GATGCGAAGT | TCTNATTCCA | GTGTTTTAGT | CCTTTGCATC | 240 |
| TTTNATGTTN | AGACTTGCCT | CTNTNAAATT | GCTTTTGTNT | TCTGCAGGTA | CTATCTGTGG | 300 |

```
TTTAACAAAA TAGAANNACT TCTCTGCTTN GAANATTTGA ATATCTTACA TCTNAAAATN      360

AATTCTCTCC CCATANNAAA ACCCANGCCC TTGGGANAAT TTGAAAAANG GNTCCTTCNN      420

AATTCNNANA ANTTCAGNTN TCATACAACA NAACNGGANC CCC                        463
```

(2) INFORMATION FOR SEQ ID NO: 90:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 90:

```
AGGGATTGAA GGTCTNTTNT ACTGTCGGAC TGTTCANCCA CCAACTCTAC AAGTTGCTGT       60

CTTCCACTCA CTGTCTGTAA GCNTNTTAAC CCAGACTGTA TCTTCATAAA TAGAACAAAT      120

TCTTCACCAG TCACATCTTC TAGGACCTTT TTGGATTCAG TTAGTATAAG CTCTTCCACT      180

TCCTTTGTTA AGACTTCATC TGGTAAAGTC TTAAGTTTTG TAGAAAGGAA TTTAATTGCT      240

CGTTCTCTAA CAATGTCCTC TCCTTGAAGT ATTTGGCTGA ACAACCCACC TNAAGTCCCT      300

TTGTGCATCC ATTTTAAATA TACTTAATAG GGCATTGGTN CACTAGGTTA AATTCTGCAA      360

GAGTCATCTG TCTGCAAAAG TTGCGTTAGT ATATCTGCCA                            400
```

(2) INFORMATION FOR SEQ ID NO: 91:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 91:

```
GAGCTCGGAT CCAATAATCT TTGTCTGAGG GCAGCACACA TATNCAGTGC CATGGNAACT       60

GGTCTACCCC ACATGGGAGC AGCATGCCGT AGNTATATAA GGTCATTCCC TGAGTCAGAC      120

ATGCCTCTTT GACTACCGTG TGCCAGTGCT GGTGATTCTC ACACACCTCC NNCCGCTCTT      180

TGTGGAAAAA CTGGCACTTG NCTGGAACTA GCAAGACATC ACTTACAAAT TCACCCACGA      240

GACACTTGAA AGGTGTAACA AAGCGACTCT TGCATTGCTT TTTGTCCCTC CGGCACCAGT      300

TGTCAATACT AACCCGCTGG TTTGCCTCCA TCACATTTGT GATCTGTAGC TCTGGATACA      360

TCTCCTGACA GTACTGAAGA ACTTCTTCTT TTGTTTCAAA AGCAACTCTT GGTGCCTGTT      420

NGATCAGGTT CCCATTTCCC AGTCCGAATG TTCACATGGC ATATNTTACT TCCCACAAAA      480
```

(2) INFORMATION FOR SEQ ID NO: 92:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: cDNA

```
    (vi) ORIGINAL SOURCE:
         (A) ORGANISM: Homo sapiens (xi) SEQUENCE DESCRIPTION: SEQ ID NO: 92:

ATACAGCCCA NATCCCACCA CGAAGATGCG CTTGTTGACT GAGAACCTGA TGCGGTCACT      60

GGTCCCGCTG TAGCCCCAGC GACTCTCCAC CTGCTGGAAG CGGTTGATGC TGCACTCCTT     120

CCCACGCAGG CAGCAGCGGG GCCGGTCAAT GAACTCCACT CGTGGCTTGG GGTTGACGGT     180

TAANTGCAGG AAGAGGCTGA CCACCTCGCG GTCCACCAGG ATGCCCGACT GTGCGGGACC     240

TGCAGCGAAA CTCCTCGATG GTCATGAGCG GGAAGCGAAT GANGCCCAGG GCCTTGCCCA     300

GAACCTTCCG CCTGTTCTCT GGCGTCACCT GCAGCTGCTG CCGCTNACAC TCGGCCTCGG     360

ACCAGCGGAC AAACGGCGTT GAACAGCCGC ACCTCACGGA TGCCCANTGT GTCGCGCTCC     420

AGGAACGGCN CCAGCGTGTC CAGGTCAATG TCGGTGAANC CTCCGCGGGT AATGGCG        477

(2) INFORMATION FOR SEQ ID NO: 93:

(i) SEQUENCE CHARACTERISTICS:
         (A) LENGTH: 377 base pairs
         (B) TYPE: nucleic acid
         (C) STRANDEDNESS: single
         (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 93:

GAACGGCTGG ACCTTGCCTC GCATTGTGCT GCTGGCAGGA ATACCTTGGC AAGCAGCTCC      60

AGTCCGAGCA GCCCCAGACC GCTGCCGCCC GAAGCTAAGC CTGCCTCTGG CCTTCCCCTC     120

CGCCTCAATG CAGAACCANT AGTGGGAGCA CTGTGTTTAG AGTTAAGAGT GAACACTGTN     180

TGATTTTACT TGGGAATTTC CTCTGTTATA TAGCTTTTCC CAATGCTAAT TTCCAAACAA     240

CAACAACAAA ATAACATGTT TGCCTGTTNA GTTGTATAAA AGTANGTGAT TCTGTATNTA     300

AAGAAAATAT TACTGTTACA TATACTGCTT GCAANTTCTG TATTTATTGG TNCTCTGGAA     360

ATAAATATAT TATTAAA                                                   377

(2) INFORMATION FOR SEQ ID NO: 94:

(i) SEQUENCE CHARACTERISTICS:
         (A) LENGTH: 495 base pairs
         (B) TYPE: nucleic acid
         (C) STRANDEDNESS: single
         (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 94:

CCCTTTGAGG GGTTAGGGTC CAGTTCCCAG TGGAAGAAAC AGGCCAGGAG AANTGCGTGC      60

CGAGCTGANG CAGATTTCCC ACAGTGACCC CAGAGCCCTG GGCTATAGTC TCTGACCCCT     120

CCAAGGAAAG ACCACCTTCT GGGGACATGG GCTGGAGGGC AGGACCTAGA GGCACCAAGG     180

GAAGGCCCCA TTCCGGGGCT GTTCCCCGAG GAGGAAGGGA AGGGGCTCTG TGTGCCCCCC     240

ACGAGGAANA GGCCCTGANT CCTGGGATCA NACACCCCTT CACGTGTATC CCCACACAAA     300

TGCAAGCTCA CCAAGGTCCC CTCTCAGTCC CTTCCCTACA CCCTGAACGG NCACTGGCCC     360
```

```
ACACCCACCC AGANCANCCA CCCGCCATGG GGAATGTNCT CAAGGAATCG CNGGGCAACG      420

TGGACTCTNG TCCCNNAAGG GGGCAGAATC TCCAATAGAN GGANNGAACC CTTGCTNANA      480

AAAAAAAANA AAAAA                                                       495
```

(2) INFORMATION FOR SEQ ID NO: 95:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 95:

```
GGTTACTTGG TTTCATTGCC ACCACTTAGT GGATGTCATT TAGAACCATT TTGTCTGCTC       60

CCTCTGGAAG CCTTGCGCAG AGCGGACTTT GTAATTGTTG GAGAATAACT GCTGAATTTT      120

TAGCTGTTTT GAGTTGATTC GCACCACTGC ACCACAACTC AATATGAAAA CTATTTNACT      180

TATTTATTAT CTTGTGAAAA GTATACAATG AAAATTTTGT TCATACTGTA TTTATCAAGT      240

ATGATGAAAA GCAATAGATA TATATTCTTT TATTATGTTN AATTATGATT GCCATTATTA      300

ATCGGCAAAA TGTGGAGTGT ATGTTCTTTT CACAGTAATA TATGCCTTTT GTAACTTCAC      360

TTGGTTATTT TATTGTAAAT GAATTACAAA ATTCTTAATT TAAGAAAATG GTANGTTATA      420

TTTANTTCAN TAATTTCTTT CCTTGTTTAC GTTAATTTTG AAAAGAATGC AT              472
```

(2) INFORMATION FOR SEQ ID NO: 96:

(i) SEQUENCE CHARACTERISTICS:
        (A) LENGTH: 476 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 96:

```
CTGAAGCATT TCTTCAAACT TNTCTACTTT TGTCATTGAT ACCTGTAGTA AGTTGACAAT       60

GTGGTGAAAT TTCAAAATTA TATGTAACTT CTACTAGTTT TACTTTCTCC CCCAAGTCTT      120

TTTTAACTCA TGATTTTTAC ACACACAATC CAGAACTTAT TATATAGCCT CTAAGTCTTT      180

ATTCTTCACA GTAGATGATG AAAGAGTCCT CCAGTGTCTT GNGCANAATG TTCTAGNTAT      240

AGCTGGATAC ATACNGTGGG AGTTCTATAA ACTCATACCT CAGTGGGACT NAACCAAAAT      300

TGTGTTAGTC TCAATTCCTA CCACACTGAG GGAGCCTCCC AAATCACTAT ATTCTTATCT      360

GCAGGTACTC CTCCAGAAAA ACNGACAGGG CAGGCTTGCA TGAAAAAGTN ACATCTGCGT      420

TACAAAGTCT ATCTTCCTCA NANGTCTGTN AAGGAACAAT TTAATCTTCT AGCTTT         476
```

(2) INFORMATION FOR SEQ ID NO: 97:

(i) SEQUENCE CHARACTERISTICS:
        (A) LENGTH: 479 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
     (A) ORGANISM: Homo sapiens (xi) SEQUENCE DESCRIPTION: SEQ ID NO: 97:

| | | | | | |
|---|---|---|---|---|---|
| ACTCTTTCTA | ATGCTGATAT | GATCTTGAGT | ATAAGAATGC | ATATGTCACT | AGAATGGATA | 60 |
| AAATAATGCT | GCAAACTTAA | TGTTCTTATG | CAAAATGGAA | CGCTAATGAA | ACACAGCTTA | 120 |
| CAATCGCAAA | TCAAAACTCA | CAAGTGCTCA | TCTGTTGTAG | ATTTAGTGTA | ATAAGACTTA | 180 |
| GATTGTGCTC | CTTCGGATAT | GATTGTTTCT | CANATCTTGG | GCAATNTTCC | TTAGTCAAAT | 240 |
| CAGGCTACTA | GAATTCTGTT | ATTGGATATN | TGAGAGCATG | AAATTTTTAA | NAATACACTT | 300 |
| GTGATTATNA | AATTAATCAC | AAATTTCACT | TATACCTGCT | ATCAGCAGCT | AGAAAAACAT | 360 |
| NTNNTTTTTA | NATCAAAGTA | TTTTGTGTTT | GGAANTGTNN | AAATGAAATC | TGAATGTGGG | 420 |
| TTCNATCTTA | TTTTTTCCCN | GACNACTANT | TNCTTTTTTA | GGGNCTATTC | TGANCCATC | 479 |

(2) INFORMATION FOR SEQ ID NO: 98:

(i) SEQUENCE CHARACTERISTICS:
    (A) LENGTH: 461 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
     (A) ORGANISM: Homo sapiens (xi) SEQUENCE DESCRIPTION: SEQ ID NO: 98:

| | | | | | |
|---|---|---|---|---|---|
| AGTGACTTGT | CCTCCAACAA | AACCCCTTGA | TCAAGTTTGT | GGCACTGACA | ATCAGACCTA | 60 |
| TGCTAGTTCC | TGTCATCTAT | TCGCTACTAA | ATGCAGACTG | GAGGGACCA | AAAAGGGGCA | 120 |
| TCAACTCCAG | CTGGATTATT | TTGGAGCCTG | CAAATCTATT | CCTACTTGTA | CGGACTTTGA | 180 |
| AGTGATTCAG | TTTCCTCTAC | GGATGAGAGA | CTGGCTCAAG | AATATCCTCA | TGCAGCTTTA | 240 |
| TGAAGCCACT | CTGAACACGC | TGGTTATCTA | GATGAGAACA | GAGAAATAAA | GTCAGAAAAT | 300 |
| TTACCTGGAG | AAAAGAGGCT | TTGGCTGGGG | ACCATCCCAT | TGAACCTTCT | CTTAAGGACT | 360 |
| TTAAGAAAAA | CTACCACATG | TTGTGTATCC | TGGTGCCGGC | CGTTTATGAA | CTGACCACCC | 420 |
| TTTGGAATAA | TCTTGACGCT | CCTGAACTTG | CTCCTCTGCG | A | | 461 |

(2) INFORMATION FOR SEQ ID NO: 99:

(i) SEQUENCE CHARACTERISTICS:
    (A) LENGTH: 171 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
     (A) ORGANISM: Homo sapiens (xi) SEQUENCE DESCRIPTION: SEQ ID NO: 99:

| | | | | | |
|---|---|---|---|---|---|
| GTGGCCGCGC | GCAGGTGTTT | CCTCGTACCG | CAGGGCCCCC | TCCCTTCCCC | AGGCGTCCCT | 60 |
| CGGCGCCTCT | GCGGGCCCGA | GGAGGAGCGG | CTGGCGGGTG | GGGGAGTGT | GACCCACCCT | 120 |
| CGGTGAGAAA | AGCCTTCTCT | AGCGATCTGA | GAGGCGTGCC | TTGGGGGTAC | C | 171 |

(2) INFORMATION FOR SEQ ID NO: 100:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 100:

```
CGGCCGCAAG TGCAACTCCA GCTGGGGCCG TGCGGACGAA GATTCTGCCA GCAGTTGGTC      60

CGACTGCGAC GACGGCGGCG GCGACAGTCG CAGGTGCAGC GCGGGCGCCT GGGGTCTTGC     120

AAGGCTGAGC TGACGCCGCA GAGGTCGTGT CACGTCCCAC GACCTTGACG CCGTCGGGGA     180

CAGCCGGAAC AGAGCCCGGT GAAGCGGGAG GCCTCGGGGA GCCCCTCGGG AAGGGCGGCC     240

CGAGAGATAC GCAGGTGCAG GTGGCCGCC                                      269
```

(2) INFORMATION FOR SEQ ID NO: 101:
    (i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 101:

```
TTTTTTTTTT TTTTGGAATC TACTGCGAGC ACAGCAGGTC AGCAACAAGT TTATTTTGCA      60

GCTAGCAAGG TAACAGGGTA GGGCATGGTT ACATGTTCAG GTCAACTTCC TTTGTCGTGG     120

TTGATTGGTT TGTCTTTATG GGGGCGGGGT GGGGTAGGGG AAACGAAGCA AATAACATGG     180

AGTGGGTGCA CCCTCCCTGT AGAACCTGGT TACAAAGCTT GGGGCAGTTC ACCTGGTCTG     240

TGACCGTCAT TTTCTTGACA TCAATGTTAT TAGAAGTCAG GATATCTTTT AGAGAGTCCA     300

CTGTTCTGGA GGGAGATTAG GGTTTCTTGC CAAATCCAAC AAAATCCACT GAAAAGTTG      360

GATGATCAGT ACGAATACCG AGGCATATTC TCATATCGGT GGCCA                    405
```

(2) INFORMATION FOR SEQ ID NO: 102:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 102:

```
TTTTTTTTTT TTTTTTTTTT TTTTTTTTTT TTTTTTTTTT TTTTTTTTT TTTTTTTTT       60

GGCACTTAAT CCATTTTTAT TTCAAAATGT CTACAAATTT AATCCCATTA TACGGTATTT     120

TCAAAATCTA AATTATTCAA ATTAGCCAAA TCCTTACCAA ATAATACCCA AAAATCAAAA     180

ATATACTTCT TTCAGCAAAC TTGTTACATA AATTAAAAAA ATATATACGG CTGGTGTTTT     240

CAAAGTACAA TTATCTTAAC ACTGCAAACA TTTTAAGGAA CTAAAATAAA AAAAAACACT     300
```

```
CCGCAAAGGT TAAAGGGAAC AACAAATTCT TTTACAACAC CATTATAAAA ATCATATCTC        360

AAATCTTAGG GGAATATATA CTTCACACGG GATCTTAACT TTTACTCACT TTGTTTATTT        420

TTTTAAACCA TTGTTTGGGC CCAACACAAT GGAATCCCCC CTGGACTAGT                   470
```

(2) INFORMATION FOR SEQ ID NO: 103:

(i) SEQUENCE CHARACTERISTICS:
        (A) LENGTH: 581 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 103:

```
TTTTTTTTTT TTTTTTTTGA CCCCCCTCTT ATAAAAAACA AGTTACCATT TTATTTTACT         60

TACACATATT TATTTTATAA TTGGTATTAG ATATTCAAAA GGCAGCTTTT AAAATCAAAC        120

TAAATGGAAA CTGCCTTAGA TACATAATTC TTAGGAATTA GCTTAAAATC TGCCTAAAGT        180

GAAAATCTTC TCTAGCTCTT TTGACTGTAA ATTTTTGACT CTTGTAAAAC ATCCAAATTC        240

ATTTTTCTTG TCTTTAAAAT TATCTAATCT TTCCATTTTT TCCCTATTCC AAGTCAATTT        300

GCTTCTCTAG CCTCATTTCC TAGCTCTTAT CTACTATTAG TAAGTGGCTT TTTTCCTAAA        360

AGGGAAAACA GGAAGAGAAA TGGCACACAA AACAAACATT TTATATTCAT ATTTCTACCT        420

ACGTTAATAA AATAGCATTT TGTGAAGCCA GCTCAAAAGA AGGCTTAGAT CCTTTTATGT        480

CCATTTTAGT CACTAAACGA TATCAAAGTG CCAGAATGCA AAAGGTTTGT GAACATTTAT        540

TCAAAAGCTA ATATAAGATA TTTCACATAC TCATCTTTCT G                           581
```

(2) INFORMATION FOR SEQ ID NO: 104:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 104:

```
TTTTTTTTTT TTTTTTTTTT TTTTTCTCTT CTTTTTTTTT GAAATGAGGA TCGAGTTTTT         60

CACTCTCTAG ATAGGGCATG AAGAAAACTC ATCTTTCCAG CTTTAAAATA ACAATCAAAT        120

CTCTTATGCT ATATCATATT TTAAGTTAAA CTAATGAGTC ACTGGCTTAT CTTCTCCTGA        180

AGGAAATCTG TTCATTCTTC TCATTCATAT AGTTATATCA AGTACTACCT TGCATATTGA        240

GAGGTTTTTC TTCTCTATTT ACACATATAT TTCCATGTGA ATTTGTATCA AACCTTTATT        300

TTCATGCAAA CTAGAAAATA ATGTTTCTTT TGCATAAGAG AAGAGAACAA TATAGCATTA        360

CAAAACTGCT CAAATTGTTT GTTAAGTTAT CCATTATAAT TAGTTGGCAG GAGCTAATAC        420

AAATCACATT TACGACAGCA ATAATAAAAC TGAAGTACCA GTTAAATATC CAAAATAATT        480

AAAGGAACAT TTTTAGCCTG GGTATAATTA GCTAATTCAC TTTACAAGCA TTTATTAGAA        540

TGAATTCACA TGTTATTATT CCTAGCCCAA CACAATGG                               578
```

(2) INFORMATION FOR SEQ ID NO: 105:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 105:

```
TTTTTTTTTT TTTTTCAGTA ATAATCAGAA CAATATTTAT TTTTATATTT AAAATTCATA    60
GAAAAGTGCC TTACATTTAA TAAAAGTTTG TTTCTCAAAG TGATCAGAGG AATTAGATAT   120
GTCTTGAACA CCAATATTAA TTTGAGGAAA ATACACCAAA ATACATTAAG TAAATTATTT   180
AAGATCATAG AGCTTGTAAG TGAAAAGATA AAATTTGACC TCAGAAACTC TGAGCATTAA   240
AAATCCACTA TTAGCAAATA AATTACTATG GACTTCTTGC TTTAATTTTG TGATGAATAT   300
GGGGTGTCAC TGGTAAACCA ACACATTCTG AAGGATACAT TACTTAGTGA TAGATTCTTA   360
TGTACTTTGC TAATACGTGG ATATGAGTTG ACAAGTTTCT CTTTCTTCAA TCTTTTAAGG   420
GGCGAGAAAT GAGGAAGAAA AGAAAAGGAT TACGCATACT GTTCTTTCTA TGGAAGGATT   480
AGATATGTTT CCTTTGCCAA TATTAAAAAA ATAATAATGT TTACTACTAG TGAAACCC     538
```

(2) INFORMATION FOR SEQ ID NO: 106:

(i) SEQUENCE CHARACTERISTICS:
        (A) LENGTH: 473 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 106:

```
TTTTTTTTTT TTTTTTAGTC AAGTTTCTAT TTTTATTATA ATTAAAGTCT TGGTCATTTC    60
ATTTATTAGC TCTGCAACTT ACATATTTAA ATTAAAGAAA CGTTTTAGAC AACTGTACAA   120
TTTATAAATG TAAGGTGCCA TTATTGAGTA ATATATTCCT CCAAGAGTGG ATGTGTCCCT   180
TCTCCCACCA ACTAATGAAC AGCAACATTA GTTTAATTTT ATTAGTAGAT ATACACTGCT   240
GCAAACGCTA ATTCTCTTCT CCATCCCCAT GTGATATTGT GTATATGTGT GAGTTGGTAG   300
AATGCATCAC AATCTACAAT CAACAGCAAG ATGAAGCTAG GCTGGGCTTT CGGTGAAAAT   360
AGACTGTGTC TGTCTGAATC AAATGATCTG ACCTATCCTC GGTGGCAAGA ACTCTTCGAA   420
CCGCTTCCTC AAAGGCGCTG CCACATTTGT GGCTCTTTGC ACTTGTTTCA AAA          473
```

(2) INFORMATION FOR SEQ ID NO: 107:

(i) SEQUENCE CHARACTERISTICS:
        (A) LENGTH: 1621 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 107:

```
CGCCATGGCA CTGCAGGGCA TCTCGGTCAT GGAGCTGTCC GGCCTGGCCC CGGGCCCGTT      60
CTGTGCTATG GTCCTGGCTG ACTTCGGGGC GCGTGTGGTA CGCGTGGACC GGCCCGGCTC     120
CCGCTACGAC GTGAGCCGCT GGGCCGGGG CAAGCGCTCG CTAGTGCTGG ACCTGAAGCA     180
GCCGCGGGA GCCGCCGTGC TGCGGCGTCT GTGCAAGCGG TCGGATGTGC TGCTGGAGCC     240
CTTCCGCCGC GGTGTCATGG AGAAACTCCA GCTGGGCCCA GAGATTCTGC AGCGGGAAAA     300
TCCAAGGCTT ATTTATGCCA GGCTGAGTGG ATTTGGCCAG TCAGGAAGCT TCTGCCGGTT     360
AGCTGGCCAC GATATCAACT ATTTGGCTTT GTCAGGTGTT CTCTCAAAAA TTGGCAGAAG     420
TGGTGAGAAT CCGTATGCCC CGCTGAATCT CCTGGCTGAC TTTGCTGGTG GTGGCCTTAT     480
GTGTGCACTG GGCATTATAA TGGCTCTTTT TGACCGCACA CGCACTGACA AGGGTCAGGT     540
CATTGATGCA AATATGGTGG AAGGAACAGC ATATTTAAGT TCTTTTCTGT GGAAAACTCA     600
GAAATCGAGT CTGTGGGAAG CACCTCGAGG ACAGAACATG TTGGATGGTG GAGCACCTTT     660
CTATACGACT TACAGGACAG CAGATGGGGA ATTCATGGCT GTTGGAGCAA TAGAACCCCA     720
GTTCTACGAG CTGCTGATCA AAGGACTTGG ACTAAAGTCT GATGAACTTC CCAATCAGAT     780
GAGCATGGAT GATTGGCCAG AAATGAAGAA GAAGTTTGCA GATGTATTTG CAAAGAAGAC     840
GAAGGCAGAG TGGTGTCAAA TCTTTGACGG CACAGATGCC TGTGTGACTC CGGTTCTGAC     900
TTTTGAGGAG GTTGTTCATC ATGATCACAA CAAGGAACGG GGCTCGTTTA TCACCAGTGA     960
GGAGCAGGAC GTGAGCCCCC GCCCTGCACC TCTGCTGTTA AACACCCCAG CCATCCCTTC    1020
TTTCAAAAGG GATCCTTTCA TAGGAGAACA CACTGAGGAG ATACTTGAAG AATTTGGATT    1080
CAGCCGCGAA GAGATTTATC AGCTTAACTC AGATAAAATC ATTGAAAGTA ATAAGGTAAA    1140
AGCTAGTCTC TAACTTCCAG GCCCACGGCT CAAGTGAATT TGAATACTGC ATTTACAGTG    1200
TAGAGTAACA CATAACATTG TATGCATGGA AACATGGAGG AACAGTATTA CAGTGTCCTA    1260
CCACTCTAAT CAAGAAAAGA ATTACAGACT CTGATTCTAC AGTGATGATT GAATTCTAAA    1320
AATGGTTATC ATTAGGGCTT TGATTTATA AAACTTTGGG TACTTATACT AAATTATGGT    1380
AGTTATTCTG CCTTCCAGTT TGCTTGATAT ATTTGTTGAT ATTAAGATTC TTGACTTATA    1440
TTTTGAATGG GTTCTAGTGA AAAAGGAATG ATATATTCTT GAAGACATCG ATATACATTT    1500
ATTTACACTC TTGATTCTAC AATGTAGAAA ATGAGGAAAT GCCACAAATT GTATGGTGAT    1560
AAAAGTCACG TGAAACAAAA AAAAAAAAAA AAAAAAAAAA AAAAAAAAAA AAAAAAAAAA    1620
A                                                                  1621
```

(2) INFORMATION FOR SEQ ID NO: 108:

(i) SEQUENCE CHARACTERISTICS:
        (A) LENGTH: 382 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 108:

```
Met Ala Leu Gln Gly Ile Ser Val Met Glu Leu Ser Gly Leu Ala Pro
 1               5                  10                  15
Gly Pro Phe Cys Ala Met Val Leu Ala Asp Phe Gly Ala Arg Val Val
```

-continued

```
                20                  25                  30
Arg Val Asp Arg Pro Gly Ser Arg Tyr Asp Val Ser Arg Leu Gly Arg
             35                  40                  45

Gly Lys Arg Ser Leu Val Leu Asp Leu Lys Gln Pro Arg Gly Ala Ala
 50                  55                  60

Val Leu Arg Arg Leu Cys Lys Arg Ser Asp Val Leu Leu Glu Pro Phe
 65                  70                  75                  80

Arg Arg Gly Val Met Glu Lys Leu Gln Leu Gly Pro Glu Ile Leu Gln
                 85                  90                  95

Arg Glu Asn Pro Arg Leu Ile Tyr Ala Arg Leu Ser Gly Phe Gly Gln
             100                 105                 110

Ser Gly Ser Phe Cys Arg Leu Ala Gly His Asp Ile Asn Tyr Leu Ala
             115                 120                 125

Leu Ser Gly Val Leu Ser Lys Ile Gly Arg Ser Gly Glu Asn Pro Tyr
 130                 135                 140

Ala Pro Leu Asn Leu Leu Ala Asp Phe Ala Gly Gly Leu Met Cys
 145                 150                 155                 160

Ala Leu Gly Ile Ile Met Ala Leu Phe Asp Arg Thr Arg Thr Asp Lys
             165                 170                 175

Gly Gln Val Ile Asp Ala Asn Met Val Glu Gly Thr Ala Tyr Leu Ser
             180                 185                 190

Ser Phe Leu Trp Lys Thr Gln Lys Ser Ser Leu Trp Glu Ala Pro Arg
             195                 200                 205

Gly Gln Asn Met Leu Asp Gly Gly Ala Pro Phe Tyr Thr Thr Tyr Arg
             210                 215                 220

Thr Ala Asp Gly Glu Phe Met Ala Val Gly Ala Ile Glu Pro Gln Phe
 225                 230                 235                 240

Tyr Glu Leu Leu Ile Lys Gly Leu Gly Leu Lys Ser Asp Glu Leu Pro
             245                 250                 255 sn Gln Met Ser Met Asp Asp Trp Pro Glu Met Lys Lys Lys Phe Ala
             260                 265                 270

Asp Val Phe Ala Lys Lys Thr Lys Ala Glu Trp Cys Gln Ile Phe Asp
             275                 280                 285

Gly Thr Asp Ala Cys Val Thr Pro Val Leu Thr Phe Glu Glu Val Val
 290                 295                 300

His His Asp His Asn Lys Glu Arg Gly Ser Phe Ile Thr Ser Glu Glu
 305                 310                 315                 320

Gln Asp Val Ser Pro Arg Pro Ala Pro Leu Leu Asn Thr Pro Ala
             325                 330                 335

Ile Pro Ser Phe Lys Arg Asp Pro Phe Ile Gly Glu His Thr Glu Glu
             340                 345                 350

Ile Leu Glu Glu Phe Gly Phe Ser Arg Glu Glu Ile Tyr Gln Leu Asn
             355                 360                 365

Ser Asp Lys Ile Ile Glu Ser Asn Lys Val Lys Ala Ser Leu
 370                 375                 380
```

(2) INFORMATION FOR SEQ ID NO: 109:

(i) SEQUENCE CHARACTERISTICS:
        (A) LENGTH: 1524 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO: 109:

```
GGCACGAGGC TGCGCCAGGG CCTGAGCGGA GGCGGGGGCA GCCTCGCCAG CGGGGGCCCC     60

GGGCCTGGCC ATGCCTCACT GAGCCAGCGC CTGCGCCTCT ACCTCGCCGA CAGCTGGAAC    120

CAGTGCGACC TAGTGGCTCT CACCTGCTTC CTCCTGGGCG TGGGCTGCCG GCTGACCCCG    180

GGTTTGTACC ACCTGGGCCG CACTGTCCTC TGCATCGACT TCATGGTTTT CACGGTGCGG    240

CTGCTTCACA TCTTCACGGT CAACAAACAG CTGGGGCCCA AGATCGTCAT CGTGAGCAAG    300

ATGATGAAGG ACGTGTTCTT CTTCCTCTTC TTCCTCGGCG TGTGGCTGGT AGCCTATGGC    360

GTGGCCACGG AGGGGCTCCT GAGGCCACGG GACAGTGACT TCCCAAGTAT CCTGCGCCGC    420

GTCTTCTACC GTCCCTACCT GCAGATCTTC GGGCAGATTC CCCAGGAGGA CATGGACGTG    480

GCCCTCATGG AGCACAGCAA CTGCTCGTCG GAGCCCGGCT CTGGGCACA CCCTCCTGGG    540

GCCCAGGCGG GCACCTGCGT CTCCCAGTAT GCCAACTGGC TGGTGGTGCT GCTCCTCGTC    600

ATCTTCCTGC TCGTGGCCAA CATCCTGCTG GTCAACTTGC TCATTGCCAT GTTCAGTTAC    660

ACATTCGGCA AGTACAGGG CAACAGCGAT CTCTACTGGA AGGCGCAGCG TTACCGCCTC    720

ATCCGGGAAT TCCACTCTCG GCCCGCGCTG GCCCCGCCCT TTATCGTCAT CTCCCACTTG    780

CGCCTCCTGC TCAGGCAATT GTGCAGGCGA CCCCGGAGCC CCAGCCGTC CTCCCCGGCC    840

CTCGAGCATT TCCGGGTTTA CCTTTCTAAG GAAGCCGAGC GGAAGCTGCT AACGTGGGAA    900

TCGGTGCATA AGGAGAACTT TCTGCTGGCA CGCGCTAGGG ACAAGCGGGA GAGCGACTCC    960

GAGCGTCTGA AGCGCACGTC CCAGAAGGTG GACTTGGCAC TGAAACAGCT GGGACACATC   1020

CGCGAGTACG AACAGCGCCT GAAAGTGCTG GAGCGGGAGG TCCAGCAGTG TAGCCGCGTC   1080

CTGGGGTGGG TGGCCGAGGC CCTGAGCCGC TCTGCCTTGC TGCCCCCAGG TGGGCCGCCA   1140

CCCCCTGACC TGCCTGGGTC CAAAGACTGA GCCCTGCTGG CGGACTTCAA GGAGAAGCCC   1200

CCACAGGGGA TTTTGCTCCT AGAGTAAGGC TCATCTGGGC CTCGGCCCCC GCACCTGGTG   1260

GCCTTGTCCT TGAGGTGAGC CCCATGTCCA TCTGGGCCAC TGTCAGGACC ACCTTTGGGA   1320

GTGTCATCCT TACAAACCAC AGCATGCCCG GCTCCTCCCA GAACCAGTCC CAGCCTGGGA   1380

GGATCAAGGC CTGGATCCCG GGCCGTTATC CATCTGGAGG CTGCAGGGTC CTTGGGGTAA   1440

CAGGGACCAC AGACCCCTCA CCACTCACAG ATTCCTCACA CTGGGGAAAT AAAGCCATTT   1500

CAGAGGAAAA AAAAAAAAA AAAA                                          1524
```

(2) INFORMATION FOR SEQ ID NO: 110:

(i) SEQUENCE CHARACTERISTICS:
        (A) LENGTH: 3410 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 110:

```
GGGAACCAGC CTGCACGCGC TGGCTCCGGG TGACAGCCGC GCGCCTCGGC CAGGATCTGA     60

GTGATGAGAC GTGTCCCCAC TGAGGTGCCC CACAGCAGCA GGTGTTGAGC ATGGGCTGAG    120

AAGCTGGACC GGCACCAAAG GGCTGGCAGA AATGGGCGCC TGGCTGATTC CTAGGCAGTT    180
```

-continued

```
GGCGGCAGCA AGGAGGAGAG GCCGCAGCTT CTGGAGCAGA GCCGAGACGA AGCAGTTCTG    240

GAGTGCCTGA ACGGCCCCCT GAGCCCTACC CGCCTGGCCC ACTATGGTCC AGAGGCTGTG    300

GGTGAGCCGC CTGCTGCGGC ACCGGAAAGC CCAGCTCTTG CTGGTCAACC TGCTAACCTT    360

TGGCCTGGAG GTGTGTTTGG CCGCAGGCAT CACCTATGTG CCGCCTCTGC TGCTGGAAGT    420

GGGGGTAGAG GAGAAGTTCA TGACCATGGT GCTGGGCATT GGTCCAGTGC TGGGCCTGGT    480

CTGTGTCCCG CTCCTAGGCT CAGCCAGTGA CCACTGGCGT GGACGCTATG GCCGCCGCCG    540

GCCCTTCATC TGGGCACTGT CCTTGGGCAT CCTGCTGAGC CTCTTTCTCA TCCCAAGGGC    600

CGGCTGGCTA GCAGGGCTGC TGTGCCCGGA TCCCAGGCCC CTGGAGCTGG CACTGCTCAT    660

CCTGGGCGTG GGGCTGCTGG ACTTCTGTGG CCAGGTGTGC TTCACTCCAC TGGAGGCCCT    720

GCTCTCTGAC CTCTTCCGGG ACCCGGACCA CTGTCGCCAG GCCTACTCTG TCTATGCCTT    780

CATGATCAGT CTTGGGGGCT GCCTGGGCTA CCTCCTGCCT GCCATTGACT GGACACCAG     840

TGCCCTGGCC CCCTACCTGG GCACCCAGGA GGAGTGCCTC TTTGGCCTGC TCACCCTCAT    900

CTTCCTCACC TGCGTAGCAG CCACACTGCT GGTGGCTGAG GAGGCAGCGC TGGGCCCCAC    960

CGAGCCAGCA GAAGGGCTGT CGGCCCCCTC CTTGTCGCCC CACTGCTGTC CATGCCGGGC   1020

CCGCTTGGCT TTCCGGAACC TGGGCGCCCT GCTTCCCCGG CTGCACCAGC TGTGCTGCCG   1080

CATGCCCCGC ACCCTGCGCC GGCTCTTCGT GGCTGAGCTG TGCAGCTGGA TGGCACTCAT   1140

GACCTTCACG CTGTTTTACA CGGATTTCGT GGGCGAGGGG CTGTACCAGG GCGTGCCCAG   1200

AGCTGAGCCG GGCACCGAGG CCCGGAGACA CTATGATGAA GGCGTTCGGA TGGGCAGCCT   1260

GGGGCTGTTC CTGCAGTGCG CCATCTCCCT GGTCTTCTCT CTGGTCATGG ACCGGCTGGT   1320

GCAGCGATTC GGCACTCGAG CAGTCTATTT GGCCAGTGTG GCAGCTTTCC CTGTGGCTGC   1380

CGGTGCCACA TGCCTGTCCC ACAGTGTGGC CGTGGTGACA GCTTCAGCCG CCCTCACCGG   1440

GTTCACCTTC TCAGCCCTGC AGATCCTGCC CTACACACTG GCCTCCCTCT ACCACCGGGA   1500

GAAGCAGGTG TTCCTGCCCA AATACCGAGG GGACACTGGA GGTGCTAGCA GTGAGGACAG   1560

CCTGATGACC AGCTTCCTGC CAGGCCCTAA GCCTGGAGCT CCCTTCCCTA ATGGACACGT   1620

GGGTGCTGGA GGCAGTGGCC TGCTCCCACC TCCACCCGCG CTCTGCGGGG CCTCTGCCTG   1680

TGATGTCTCC GTACGTGTGG TGGTGGGTGA GCCCACCGAG GCCAGGGTGG TTCCGGGCCG   1740

GGGCATCTGC CTGGACCTCG CCATCCTGGA TAGTGCCTTC CTGCTGTCCC AGGTGGCCCC   1800

ATCCCTGTTT ATGGGCTCCA TTGTCCAGCT CAGCCAGTCT GTCACTGCCT ATATGGTGTC   1860

TGCCGCAGGC CTGGGTCTGG TCGCCATTTA CTTTGCTACA CAGGTAGTAT TTGACAAGAG   1920

CGACTTGGCC AAATACTCAG CGTAGAAAAC TTCCAGCACA TTGGGGTGGA GGGCCTGCCT   1980

CACTGGGTCC CAGCTCCCCG CTCCTGTTAG CCCCATGGGG CTGCCGGGCT GGCCGCCAGT   2040

TTCTGTTGCT GCCAAAGTAA TGTGGCTCTC TGCTGCCACC CTGTGCTGCT GAGGTGCGTA   2100

GCTGCACAGC TGGGGCTGG GGCGTCCCTC TCCTCTCTCC CCAGTCTCTA GGGCTGCCTG   2160

ACTGGAGGCC TTCCAAGGGG GTTTCAGTCT GGACTTATAC AGGGAGGCCA GAAGGGCTCC   2220

ATGCACTGGA ATGCGGGAC TCTGCAGGTG GATTACCCAG GCTCAGGGTT AACAGCTAGC    2280

CTCCTAGTTG AGACACACCT AGAGAAGGGT TTTTGGGAGC TGAATAAACT CAGTCACCTG   2340

GTTTCCCATC TCTAAGCCCC TTAACCTGCA GCTTCGTTTA ATGTAGCTCT TGCATGGGAG   2400

TTTCTAGGAT GAAACACTCC TCCATGGGAT TTGAACATAT GACTTATTTG TAGGGGAAGA   2460

GTCCTGAGGG GCAACACACA AGAACCAGGT CCCCTCAGCC CACAGCACTG TCTTTTTGCT   2520

GATCCACCCC CCTCTTACCT TTTATCAGGA TGTGGCCTGT TGGTCCTTCT GTTGCCATCA   2580
```

-continued

```
CAGAGACACA GGCATTTAAA TATTTAACTT ATTTATTTAA CAAAGTAGAA GGGAATCCAT    2640

TGCTAGCTTT TCTGTGTTGG TGTCTAATAT TTGGGTAGGG TGGGGGATCC CCAACAATCA    2700

GGTCCCCTGA GATAGCTGGT CATTGGGCTG ATCATTGCCA GAATCTTCTT CTCCTGGGGT    2760

CTGGCCCCCC AAAATGCCTA ACCCAGGACC TTGGAAATTC TACTCATCCC AAATGATAAT    2820

TCCAAATGCT GTTACCCAAG GTTAGGGTGT TGAAGGAAGG TAGAGGGTGG GGCTTCAGGT    2880

CTCAACGGCT TCCCTAACCA CCCCTCTTCT CTTGGCCCAG CCTGGTTCCC CCCACTTCCA    2940

CTCCCCTCTA CTCTCTCTAG GACTGGGCTG ATGAAGGCAC TGCCCAAAAT TTCCCCTACC    3000

CCCAACTTTC CCCTACCCCC AACTTTCCCC ACCAGCTCCA CAACCCTGTT TGGAGCTACT    3060

GCAGGACCAG AAGCACAAAG TGCGGTTTCC CAAGCCTTTG TCCATCTCAG CCCCCAGAGT    3120

ATATCTGTGC TTGGGGAATC TCACACAGAA ACTCAGGAGC ACCCCCTGCC TGAGCTAAGG    3180

GAGGTCTTAT CTCTCAGGGG GGGTTTAAGT GCCGTTTGCA ATAATGTCGT CTTATTTATT    3240

TAGCGGGGTG AATATTTTAT ACTGTAAGTG AGCAATCAGA GTATAATGTT TATGGTGACA    3300

AAATTAAAGG CTTTCTTATA TGTTTAAAAA AAAAAAAAAA AAAAAAAAAA AAAAAAAAAA    3360

AAAAAAAARA AAAAAAAAAA AAAAAAAAAA AAAAAAATAA AAAAAAAAA                3410
```

(2) INFORMATION FOR SEQ ID NO: 111:

(i) SEQUENCE CHARACTERISTICS:
        (A) LENGTH: 1289 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 111:

```
AGCCAGGCGT CCCTCTGCCT GCCCACTCAG TGGCAACACC CGGGAGCTGT TTTGTCCTTT      60

GTGGAGCCTC AGCAGTTCCC TCTTTCAGAA CTCACTGCCA AGAGCCCTGA ACAGGAGCCA     120

CCATGCAGTG CTTCAGCTTC ATTAAGACCA TGATGATCCT CTTCAATTTG CTCATCTTTC     180

TGTGTGGTGC AGCCCTGTTG GCAGTGGGCA TCTGGGTGTC AATCGATGGG GCATCCTTTC     240

TGAAGATCTT CGGGCCACTG TCGTCCAGTG CCATGCAGTT TGTCAACGTG GGCTACTTCC     300

TCATCGCAGC CGGCGTTGTG GTCTTTGCTC TTGGTTTCCT GGGCTGCTAT GGTGCTAAGA     360

CTGAGAGCAA GTGTGCCCTC GTGACGTTCT TCTTCATCCT CCTCCTCATC TTCATTGCTG     420

AGGTTGCAGC TGCTGTGGTC GCCTTGGTGT ACACCACAAT GGCTGAGCAC TTCCTGACGT     480

TGCTGGTAGT GCCTGCCATC AAGAAAGATT ATGGTTCCCA GGAAGACTTC ACTCAAGTGT     540

GGAACACCAC CATGAAAGGG CTCAAGTGCT GTGGCTTCAC CAACTATACG GATTTTGAGG     600

ACTCACCCTA CTTCAAAGAG AACAGTGCCT TTCCCCCATT CTGTTGCAAT GACAACGTCA     660

CCAACACAGC CAATGAAACC TGCACCAAGC AAAAGGCTCA CGACCAAAAA GTAGAGGGTT     720

GCTTCAATCA GCTTTTGTAT GACATCCGAA CTAATGCAGT CACCGTGGGT GGTGTGGCAG     780

CTGGAATTGG GGGCCTCGAG CTGGCTGCCA TGATTGTGTC CATGTATCTG TACTGCAATC     840

TACAATAAGT CCACTTCTGC CTCTGCCACT ACTGCTGCCA CATGGGAACT GTGAAGAGGC     900

ACCCTGGCAA GCAGCAGTGA TTGGGGGAGG GGACAGGATC TAACAATGTC ACTTGGGCCA     960

GAATGGACCT GCCCTTTCTG CTCCAGACTT GGGGCTAGAT AGGGACCACT CCTTTTAGCG    1020
```

```
ATGCCTGACT TTCCTTCCAT TGGTGGGTGG ATGGGTGGGG GGCATTCCAG AGCCTCTAAG    1080

GTAGCCAGTT CTGTTGCCCA TTCCCCCAGT CTATTAAACC CTTGATATGC CCCCTAGGCC    1140

TAGTGGTGAT CCCAGTGCTC TACTGGGGGA TGAGAGAAAG GCATTTTATA GCCTGGGCAT    1200

AAGTGAAATC AGCAGAGCCT CTGGGTGGAT GTGTAGAAGG CACTTCAAAA TGCATAAACC    1260

TGTTACAATG TTAAAAAAAA AAAAAAAA                                     1289
```

(2) INFORMATION FOR SEQ ID NO: 112:

(i) SEQUENCE CHARACTERISTICS:
        (A) LENGTH: 315 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 112:

```
Met Val Phe Thr Val Arg Leu Leu His Ile Phe Thr Val Asn Lys Gln
1               5                   10                  15

Leu Gly Pro Lys Ile Val Ile Val Ser Lys Met Met Lys Asp Val Phe
                20                  25                  30

Phe Phe Leu Phe Phe Leu Gly Val Trp Leu Val Ala Tyr Gly Val Ala
            35                  40                  45

Thr Glu Gly Leu Leu Arg Pro Arg Asp Ser Asp Phe Pro Ser Ile Leu
        50                  55                  60

Arg Arg Val Phe Tyr Arg Pro Tyr Leu Gln Ile Phe Gly Gln Ile Pro
65                  70                  75                  80

Gln Glu Asp Met Asp Val Ala Leu Met Glu His Ser Asn Cys Ser Ser
                85                  90                  95

Glu Pro Gly Phe Trp Ala His Pro Pro Gly Ala Gln Ala Gly Thr Cys
                100                 105                 110

Val Ser Gln Tyr Ala Asn Trp Leu Val Val Leu Leu Val Ile Phe
            115                 120                 125

Leu Leu Val Ala Asn Ile Leu Leu Val Asn Leu Leu Ile Ala Met Phe
        130                 135                 140

Ser Tyr Thr Phe Gly Lys Val Gln Gly Asn Ser Asp Leu Tyr Trp Lys
145                 150                 155                 160

Ala Gln Arg Tyr Arg Leu Ile Arg Glu Phe His Ser Arg Pro Ala Leu
                165                 170                 175

Ala Pro Pro Phe Ile Val Ile Ser His Leu Arg Leu Leu Leu Arg Gln
            180                 185                 190

Leu Cys Arg Arg Pro Arg Ser Pro Gln Pro Ser Ser Pro Ala Leu Glu
        195                 200                 205

His Phe Arg Val Tyr Leu Ser Lys Glu Ala Glu Arg Lys Leu Leu Thr
    210                 215                 220

Trp Glu Ser Val His Lys Glu Asn Phe Leu Leu Ala Arg Ala Arg Asp
225                 230                 235                 240

Lys Arg Glu Ser Asp Ser Glu Arg Leu Lys Arg Thr Ser Gln Lys Val
                245                 250                 255

Asp Leu Ala Leu Lys Gln Leu Gly His Ile Arg Glu Tyr Glu Gln Arg
            260                 265                 270

Leu Lys Val Leu Glu Arg Glu Val Gln Gln Cys Ser Arg Val Leu Gly
        275                 280                 285
```

```
Trp Val Ala Glu Ala Leu Ser Arg Ser Ala Leu Leu Pro Pro Gly Gly
    290                 295                 300

Pro Pro Pro Pro Asp Leu Pro Gly Ser Lys Asp
305             310                 315
```

(2) INFORMATION FOR SEQ ID NO: 113:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 113:

```
Met Val Gln Arg Leu Trp Val Ser Arg Leu Leu Arg His Arg Lys Ala
1               5                   10                  15

Gln Leu Leu Val Asn Leu Leu Thr Phe Gly Leu Glu Val Cys Leu
            20                  25                  30

Ala Ala Gly Ile Thr Tyr Val Pro Pro Leu Leu Glu Val Gly Val
        35                  40                  45

Glu Glu Lys Phe Met Thr Met Val Leu Gly Ile Gly Pro Val Leu Gly
    50                  55                  60

Leu Val Cys Val Pro Leu Leu Gly Ser Ala Ser Asp His Trp Arg Gly
65                  70                  75                  80

Arg Tyr Gly Arg Arg Pro Phe Ile Trp Ala Leu Ser Leu Gly Ile
            85                  90                  95

Leu Leu Ser Leu Phe Leu Ile Pro Arg Ala Gly Trp Leu Ala Gly Leu
                100                 105                 110

Leu Cys Pro Asp Pro Arg Pro Leu Glu Leu Ala Leu Leu Ile Leu Gly
            115                 120                 125

Val Gly Leu Leu Asp Phe Cys Gly Gln Val Cys Phe Thr Pro Leu Glu
    130                 135                 140

Ala Leu Leu Ser Asp Leu Phe Arg Asp Pro Asp His Cys Arg Gln Ala
145                 150                 155                 160

Tyr Ser Val Tyr Ala Phe Met Ile Ser Leu Gly Gly Cys Leu Gly Tyr
                165                 170                 175

Leu Leu Pro Ala Ile Asp Trp Asp Thr Ser Ala Leu Ala Pro Tyr Leu
            180                 185                 190

Gly Thr Gln Glu Glu Cys Leu Phe Gly Leu Leu Thr Leu Ile Phe Leu
    195                 200                 205

Thr Cys Val Ala Ala Thr Leu Leu Val Ala Glu Glu Ala Ala Leu Gly
210                 215                 220

Pro Thr Glu Pro Ala Glu Gly Leu Ser Ala Pro Ser Leu Ser Pro His
225                 230                 235                 240

Cys Cys Pro Cys Arg Ala Arg Leu Ala Phe Arg Asn Leu Gly Ala Leu
            245                 250                 255

Leu Pro Arg Leu His Gln Leu Cys Cys Arg Met Pro Arg Thr Leu Arg
            260                 265                 270

Arg Leu Phe Val Ala Glu Leu Cys Ser Trp Met Ala Leu Met Thr Phe
            275                 280                 285

Thr Leu Phe Tyr Thr Asp Phe Val Gly Glu Gly Leu Tyr Gln Gly Val
    290                 295                 300
```

```
Pro Arg Ala Glu Pro Gly Thr Glu Ala Arg Arg His Tyr Asp Glu Gly
305                 310                 315                 320

Val Arg Met Gly Ser Leu Gly Leu Phe Leu Gln Cys Ala Ile Ser Leu
                325                 330                 335

Val Phe Ser Leu Val Met Asp Arg Leu Val Gln Arg Phe Gly Thr Arg
            340                 345                 350

Ala Val Tyr Leu Ala Ser Val Ala Ala Phe Pro Val Ala Ala Gly Ala
            355                 360                 365

Thr Cys Leu Ser His Ser Val Ala Val Thr Ala Ser Ala Ala Leu
            370                 375                 380

Thr Gly Phe Thr Phe Ser Ala Leu Gln Ile Leu Pro Tyr Thr Leu Ala
385                 390                 395                 400

Ser Leu Tyr His Arg Glu Lys Gln Val Phe Leu Pro Lys Tyr Arg Gly
                405                 410                 415

Asp Thr Gly Gly Ala Ser Ser Glu Asp Ser Leu Met Thr Ser Phe Leu
            420                 425                 430

Pro Gly Pro Lys Pro Gly Ala Pro Phe Pro Asn Gly His Val Gly Ala
            435                 440                 445

Gly Gly Ser Gly Leu Leu Pro Pro Pro Ala Leu Cys Gly Ala Ser
450                 455                 460

Ala Cys Asp Val Ser Val Arg Val Val Val Gly Glu Pro Thr Glu Ala
465                 470                 475                 480

Arg Val Val Pro Gly Arg Gly Ile Cys Leu Asp Leu Ala Ile Leu Asp
                485                 490                 495

Ser Ala Phe Leu Leu Ser Gln Val Ala Pro Ser Leu Phe Met Gly Ser
            500                 505                 510

Ile Val Gln Leu Ser Gln Ser Val Thr Ala Tyr Met Val Ser Ala Ala
            515                 520                 525

Gly Leu Gly Leu Val Ala Ile Tyr Phe Ala Thr Gln Val Val Phe Asp
            530                 535                 540

Lys Ser Asp Leu Ala Lys Tyr Ser Ala
545                 550

(2) INFORMATION FOR SEQ ID NO: 114:

(i) SEQUENCE CHARACTERISTICS:
        (A) LENGTH: 241 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 114:

Met Gln Cys Phe Ser Phe Ile Lys Thr Met Met Ile Leu Phe Asn Leu
1               5                   10                  15

Leu Ile Phe Leu Cys Gly Ala Ala Leu Leu Ala Val Gly Ile Trp Val
                20                  25                  30

Ser Ile Asp Gly Ala Ser Phe Leu Lys Ile Phe Gly Pro Leu Ser Ser
            35                  40                  45

Ser Ala Met Gln Phe Val Asn Val Gly Tyr Phe Leu Ile Ala Ala Gly
            50                  55                  60

Val Val Val Phe Ala Leu Gly Phe Leu Gly Cys Tyr Gly Ala Lys Thr
65                  70                  75                  80
```

```
Glu Ser Lys Cys Ala Leu Val Thr Phe Phe Ile Leu Leu Ile
            85                  90                  95

Phe Ile Ala Glu Val Ala Ala Ala Val Val Ala Leu Val Tyr Thr Thr
                100                 105                 110

Met Ala Glu His Phe Leu Thr Leu Leu Val Val Pro Ala Ile Lys Lys
                115                 120                 125

Asp Tyr Gly Ser Gln Glu Asp Phe Thr Gln Val Trp Asn Thr Thr Met
            130                 135                 140

Lys Gly Leu Lys Cys Cys Gly Phe Thr Asn Tyr Thr Asp Phe Glu Asp
145                 150                 155                 160

Ser Pro Tyr Phe Lys Glu Asn Ser Ala Phe Pro Pro Phe Cys Cys Asn
                165                 170                 175

Asp Asn Val Thr Asn Thr Ala Asn Glu Thr Cys Thr Lys Gln Lys Ala
                180                 185                 190

His Asp Gln Lys Val Glu Gly Cys Phe Asn Gln Leu Leu Tyr Asp Ile
            195                 200                 205

Arg Thr Asn Ala Val Thr Val Gly Gly Val Ala Ala Gly Ile Gly Gly
            210                 215                 220

Leu Glu Leu Ala Ala Met Ile Val Ser Met Tyr Leu Tyr Cys Asn Leu
225                 230                 235                 240

Gln
```

(2) INFORMATION FOR SEQ ID NO: 115:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo Sapiens (xi) SEQUENCE DESCRIPTION: SEQ ID NO: 115:

```
GCTCTTTCTC TCCCCTCCTC TGAATTTAAT TCTTTCAACT TGCAATTTGC AAGGATTACA    60

CATTTCACTG TGATGTATAT TGTGTTGCAA AAAAAAAAAA GTGTCTTTGT TTAAAATTAC   120

TTGGTTTGTG AATCCATCTT GCTTTTTCCC CATTGGAACT AGTCATTAAC CCATCTCTGA   180

ACTGGTAGAA AAACATCTGA AGAGCTAGTC TATCAGCATC TGACAGGTGA ATTGGATGGT   240

TCTCAGAACC ATTTCACCCA GACAGCCTGT TTCTATCCTG TTTAATAAAT TAGTTTGGGT   300

TCTCTACATG CATAACAAAC CCTGCTCCAA TCTGTCACAT AAAAGTCTGT GACTTGAAGT   360

TTAGTC                                                              366
```

(2) INFORMATION FOR SEQ ID NO: 116:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 116:

```
ACAAAGATGA ACCATTTCCT ATATTATAGC AAAATTAAAA TCTACCCGTA TTCTAATATT      60

GAGAAATGAG ATNAAACACA ATNTTATAAA GTCTACTTAG AGAAGATCAA GTGACCTCAA     120

AGACTTTACT ATTTTCATAT TTTAAGACAC ATGATTTATC CTATTTTAGT AACCTGGTTC     180

ATACGTTAAA CAAAGGATAA TGTGAACAGC AGAGAGGATT TGTTGGCAGA AAATCTATGT     240

TCAATCTNGA ACTATCTANA TCACAGACAT TTCTATTCCT TT                       282

(2) INFORMATION FOR SEQ ID NO: 117:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 117:

ACACATGTCG CTTCACTGCC TTCTTAGATG CTTCTGGTCA ACATANAGGA ACAGGGACCA      60

TATTTATCCT CCCTCCTGAA ACAATTGCAA ATAANACAA AATATATGAA ACAATTGCAA     120

AATAAGGCAA AATATATGAA ACAACAGGTC TCGAGATATT GGAAATCAGT CAATGAAGGA     180

TACTGATCCC TGATCACTGT CCTAATGCAG GATGTGGGAA ACAGATGAGG TCACCTCTGT     240

GACTGCCCCA GCTTACTGCC TGTAGAGAGT TTCTANGCTG CAGTTCAGAC AGGGAGAAAT     300

TGGGT                                                                305

(2) INFORMATION FOR SEQ ID NO: 118:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 118:

ACCAAGGTGT NTGAATCTCT GACGTGGGGA TCTCTGATTC CCGCACAATC TGAGTGGAAA      60

AANTCCTGGG T                                                          71

(2) INFORMATION FOR SEQ ID NO: 119:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 119:

ACTCCGGTTG GTGTCAGCAG CACGTGGCAT TGAACATNGC AATGTGGAGC CCAAACCACA      60

GAAAATGGGG TGAAATTGGC CAACTTTCTA TNAACTTATG TTGGCAANTT TGCCACCAAC     120

AGTAAGCTGG CCCTTCTAAT AAAAGAAAAT TGAAAGGTTT CTCACTAANC GGAATTAANT     180
```

AATGGANTCA AGANACTCCC AGGCCTCAGC GT                                      212

(2) INFORMATION FOR SEQ ID NO: 120:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 120:

ACTCGTTGCA NATCAGGGGC CCCCCAGAGT CACCGTTGCA GGAGTCCTTC TGGTCTTGCC          60

CTCCGCCGGC GCAGAACATG CTGGGGTGGT                                          90

(2) INFORMATION FOR SEQ ID NO: 121:

(i) SEQUENCE CHARACTERISTICS:
        (A) LENGTH: 218 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 121:

TGTANCGTGA ANACGACAGA NAGGGTTGTC AAAAATGGAG AANCCTTGAA GTCATTTTGA          60

GAATAAGATT TGCTAAAAGA TTTGGGGCTA AAACATGGTT ATTGGGAGAC ATTTCTGAAG         120

ATATNCANGT AAATTANGGA ATGAATTCAT GGTTCTTTTG GGAATTCCTT TACGATNGCC         180

AGCATANACT TCATGTGGGG ATANCAGCTA CCCTTGTA                                 218

(2) INFORMATION FOR SEQ ID NO: 122:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 122:

TAGGGGTGTA TGCAACTGTA AGGACAAAAA TTGAGACTCA ACTGGCTTAA CCAATAAAGG          60

CATTTGTTAG CTCATGGAAC AGGAAGTCGG ATGGTGGGGC ATCTTCAGTG CTGCATGAGT         120

CACCACCCCG GCGGGGTCAT CTGTGCCACA GGTCCCTGTT GACAGTGCGG T                 171

(2) INFORMATION FOR SEQ ID NO: 123:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO: 123:

```
TGTAGCGTGA AGACNACAGA ATGGTGTGTG CTGTGCTATC CAGGAACACA TTTATTATCA      60

TTATCAANTA TTGTGT                                                      76
```

(2) INFORMATION FOR SEQ ID NO: 124:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 124:

```
ACCTTTCCCC AAGGCCAATG TCCTGTGTGC TAACTGGCCG GCTGCAGGAC AGCTGCAATT      60

CAATGTGCTG GGTCATATGG AGGGGAGGAG ACTCTAAAAT AGCCAATTTT ATTCTCTTGG     120

TTAAGATTTG T                                                         131
```

(2) INFORMATION FOR SEQ ID NO: 125:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 125:

```
ACTTTATCTA CTGGCTATGA AATAGATGGT GGAAAATTGC GTTACCAACT ATACCACTGG      60

CTTGAAAAAG AGGTGATAGC TCTTCAGAGG ACTTGTGACT TTTGCTCAGA TGCTGAAGAA     120

CTACAGTCTG CATTTGGCAG AAATGAAGAT GAATTTGGAT TAAATGAGGA TGCTGAAGAT     180

TTGCCTCACC AAACAAAAGT GAAACAACTG AGAGAAAATT TCAGGAAAA AAGACAGTGG      240

CTCTTGAAGT ATCAGTCACT TTTGAGAATG TTTCTTAGTT ACTGCATACT TCATGGATCC     300

CATGGTGGGG GTCTTGCATC TGTAAGAATG GAATTGATTT TGCTTTTGCA AGAATCTCAG     360

CAGGAAACAT CAGAACCACT ATTTTCTAGC CCTCTGTCAG AGCAAACCTC AGTGCCTCTC     420

CTCTTTGCTT GT                                                        432
```

(2) INFORMATION FOR SEQ ID NO: 126:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 126:

```
ACACAACTTG AATAGTAAAA TAGAAACTGA GCTGAAATTT CTAATTCACT TTCTAACCAT      60

AGTAAGAATG ATATTTCCCC CCAGGGATCA CCAAATATTT ATAAAAATTT GT             112
```

(2) INFORMATION FOR SEQ ID NO: 127:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 127:

```
ACCACGAAAC CACAAACAAG ATGGAAGCAT CAATCCACTT GCCAAGCACA GCAG           54
```

(2) INFORMATION FOR SEQ ID NO: 128:

(i) SEQUENCE CHARACTERISTICS:
        (A) LENGTH: 323 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 128:

```
ACCTCATTAG TAATTGTTTT GTTGTTTCAT TTTTTTCTAA TGTCTCCCCT CTACCAGCTC      60

ACCTGAGATA ACAGAATGAA AATGGAAGGA CAGCCAGATT TCTCCTTTGC TCTCTGCTCA     120

TTCTCTCTGA AGTCTAGGTT ACCCATTTTG GGGACCCATT ATAGGCAATA AACACAGTTC     180

CCAAAGCATT TGGACAGTTT CTTGTTGTGT TTTAGAATGG TTTTCCTTTT TCTTAGCCTT     240

TTCCTGCAAA AGGCTCACTC AGTCCCTTGC TTGCTCAGTG GACTGGGCTC CCCAGGGCCT     300

AGGCTGCCTT CTTTTCCATG TCC                                            323
```

(2) INFORMATION FOR SEQ ID NO: 129:

(i) SEQUENCE CHARACTERISTICS:
        (A) LENGTH: 192 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 129:

```
ACATACATGT GTGTATATTT TTAAATATCA CTTTTGTATC ACTCTGACTT TTTAGCATAC      60

TGAAAACACA CTAACATAAT TTNTGTGAAC CATGATCAGA TACAACCCAA ATCATTCATC     120

TAGCACATTC ATCTGTGATA NAAAGATAGG TGAGTTTCAT TTCCTTCACG TTGGCCAATG     180

GATAAACAAA GT                                                        192
```

(2) INFORMATION FOR SEQ ID NO: 130:

(i) SEQUENCE CHARACTERISTICS:

(A) LENGTH: 362 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 130:

```
CCCTTTTTTA TGGAATGAGT AGACTGTATG TTTGAANATT TANCCACAAC CTCTTTGACA      60

TATAATGACG CAACAAAAAG GTGCTGTTTA GTCCTATGGT TCAGTTTATG CCCCTGACAA     120

GTTTCCATTG TGTTTTGCCG ATCTTCTGGC TAATCGTGGT ATCCTCCATG TTATTAGTAA     180

TTCTGTATTC CATTTTGTTA ACGCCTGGTA GATGTAACCT GCTANGAGGC TAACTTTATA     240

CTTATTTAAA AGCTCTTATT TTGTGGTCAT TAAAATGGCA ATTTATGTGC AGCACTTTAT     300

TGCAGCAGGA AGCACGTGTG GGTTGGTTGT AAAGCTCTTT GCTAATCTTA AAAAGTAATG     360

GG                                                                   362
```

(2) INFORMATION FOR SEQ ID NO: 131:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 131:

```
CTTTTTGAAA GATCGTGTCC ACTCCTGTGG ACATCTTGTT TTAATGGAGT TTCCCATGCA      60

GTANGACTGG TATGGTTGCA GCTGTCCAGA TAAAAACATT TGAAGAGCTC CAAAATGAGA     120

GTTCTCCCAG GTTCGCCCTG CTGCTCCAAG TCTCAGCAGC AGCCTCTTTT AGGAGGCATC     180

TTCTGAACTA GATTAAGGCA GCTTGTAAAT CTGATGTGAT TTGGTTTATT ATCCAACTAA     240

CTTCCATCTG TTATCACTGG AGAAAGCCCA GACTCCCCAN GACNGGTACG GATTGTGGGC     300

ATANAAGGAT TGGGTGAAGC TGGCGTTGTG GT                                  332
```

(2) INFORMATION FOR SEQ ID NO: 132:

(i) SEQUENCE CHARACTERISTICS:
        (A) LENGTH: 322 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 132:

```
ACTTTTGCCA TTTTGTATAT ATAAACAATC TTGGGACATT CTCCTGAAAA CTAGGTGTCC      60

AGTGGCTAAG AGAACTCGAT TTCAAGCAAT TCTGAAAGGA AAACCAGCAT GACACAGAAT     120

CTCAAATTCC CAAACAGGGG CTCTGTGGGA AAAATGAGGG AGGACCTTTG TATCTCGGGT     180

TTTAGCAAGT TAAAATGAAN ATGACAGGAA AGGCTTATTT ATCAACAAAG AGAAGAGTTG     240

GGATGCTTCT AAAAAAAACT TTGGTAGAGA AAATAGGAAT GCTNAATCCT AGGGAAGCCT     300
```

GTAACAATCT ACAATTGGTC CA                                          322

(2) INFORMATION FOR SEQ ID NO: 133:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 133:

ACAAGCCTTC ACAAGTTTAA CTAAATTGGG ATTAATCTTT CTGTANTTAT CTGCATAATT    60

CTTGTTTTTC TTTCCATCTG GCTCCTGGGT TGACAATTTG TGGAAACAAC TCTATTGCTA   120

CTATTTAAAA AAAATCACAA ATCTTTCCCT TTAAGCTATG TTNAATTCAA ACTATTCCTG   180

CTATTCCTGT TTTGTCAAAG AAATTATATT TTTCAAAATA TGTNTATTTG TTTGATGGGT   240

CCCACGAAAC ACTAATAAAA ACCACAGAGA CCAGCCTG                           278

(2) INFORMATION FOR SEQ ID NO: 134:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 134:

GTTTANAAAA CTTGTTTAGC TCCATAGAGG AAAGAATGTT AAACTTTGTA TTTTAAAACA    60

TGATTCTCTG AGGTTAAACT TGGTTTTCAA ATGTTATTTT TACTTGTATT TTGCTTTTGG   120

T                                                                  121

(2) INFORMATION FOR SEQ ID NO: 135:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 135:

ACTTANAACC ATGCCTAGCA CATCAGAATC CCTCAAAGAA CATCAGTATA ATCCTATACC    60

ATANCAAGTG GTGACTGGTT AAGCGTGCGA CAAAGGTCAG CTGGCACATT ACTTGTGTGC   120

AAACTTGATA CTTTTGTTCT AAGTAGGAAC TAGTATACAG TNCCTAGGAN TGGTACTCCA   180

GGGTGCCCCC CAACTCCTGC AGCCGCTCCT CTGTGCCAGN CCCTGNAAGG AACTTTCGCT   240

CCACCTCAAT CAAGCCCTGG GCCATGCTAC CTGCAATTGG CTGAACAAAC GTTTGCTGAG   300

TTCCCAAGGA TGCAAAGCCT GGTGCTCAAC TCCTGGGCG TCAACTCAGT              350

(2) INFORMATION FOR SEQ ID NO: 136:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 136:

```
TGTACCGTGA AGACGACAGA AGTTGCATGG CAGGGACAGG GCAGGGCCGA GGCCAGGGTT      60

GCTGTGATTG TATCCGAATA NTCCTCGTGA GAAAAGATAA TGAGATGACG TGAGCAGCCT     120

GCAGACTTGT GTCTGCCTTC AANAAGCCAG ACAGGAAGGC CCTGCCTGCC TTGGCTCTGA     180

CCTGGCGGCC AGCCAGCCAG CCACAGGTGG GCTTCTTCCT TTTGTGGTGA CAACNCCAAG     240

AAAACTGCAG AGGCCCAGGG TCAGGTGTNA GTGGGTANGT GACCATAAAA CACCAGGTGC     300

TCCCAGGAAC CCGGGCAAAG GCCATCCCCA CCTACAGCCA GCATGCCCAC TGGCGTGATG     360

GGTGCAGANG GATGAAGCAG CCAGNTGTTC TGCTGTGGT                            399
```

(2) INFORMATION FOR SEQ ID NO: 137:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 137:

```
ACTGGTGTGG TNGGGGGTGA TGCTGGTGGT ANAAGTTGAN GTGACTTCAN GATGGTGTGT      60

GGAGGAAGTG TGTGAACGTA GGGATGTAGA NGTTTTGGCC GTGCTAAATG AGCTTCGGGA     120

TTGGCTGGTC CCACTGGTGG TCACTGTCAT TGGTGGGGTT CCTGT                    165
```

(2) INFORMATION FOR SEQ ID NO: 138:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 138:

```
ACTCACTGGA ATGCCACATT CACAACAGAA TCAGAGGTCT GTGAAAACAT TAATGGCTCC      60

TTAACTTCTC CAGTAAGAAT CAGGGACTTG AAATGGAAAC GTTAACAGCC ACATGCCCAA     120

TGCTGGGCAG TCTCCCATGC CTTCCACAGT GAAAGGGCTT GAGAAAAATC ACATCCAATG     180

TCATGTGTTT CCAGCCACAC CAAAAGGTGC TTGGGGTGGA GGGCTGGGGG CATANANGGT     240

CANGCCTCAG GAAGCCTCAA GTTCCATTCA GCTTTGCCAC TGTACATTCC CCATNTTTAA     300

AAAAACTGAT GCCTTTTTTT TTTTTTTTG TAAAATTC                              338
```

(2) INFORMATION FOR SEQ ID NO: 139:

(i) SEQUENCE CHARACTERISTICS:
        (A) LENGTH: 382 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 139:

```
GGGAATCTTG GTTTTTGGCA TCTGGTTTGC CTATAGCCGA GGCCACTTTG ACAGAACAAA      60

GAAAGGGACT TCGAGTAAGA AGGTGATTTA CAGCCAGCCT AGTGCCCGAA GTGAAGGAGA     120

ATTCAAACAG ACCTCGTCAT TCCTGGTGTG AGCCTGGTCG GCTCACCGCC TATCATCTGC     180

ATTTGCCTTA CTCAGGTGCT ACCGGACTCT GGCCCCTGAT GTCTGTAGTT TCACAGGATG     240

CCTTATTTGT CTTCTACACC CCACAGGGCC CCCTACTTCT TCGGATGTGT TTTTAATAAT     300

GTCAGCTATG TGCCCCATCC TCCTTCATGC CCTCCCTCCC TTTCCTACCA CTGCTGAGTG     360

GCCTGGAACT TGTTTAAAGT GT                                              382
```

(2) INFORMATION FOR SEQ ID NO: 140:

(i) SEQUENCE CHARACTERISTICS:
        (A) LENGTH: 200 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 140:

```
ACCAAANCTT CTTTCTGTTG TGTTNGATTT TACTATAGGG GTTTNGCTTN TTCTAAANAT      60

ACTTTTCATT TAACANCTTT TGTTAAGTGT CAGGCTGCAC TTTGCTCCAT ANAATTATTG     120

TTTTCACATT TCAACTTGTA TGTGTTTGTC TCTTANAGCA TTGGTGAAAT CACATATTTT     180

ATATTCAGCA TAAAGGAGAA                                                 200
```

(2) INFORMATION FOR SEQ ID NO: 141:

(i) SEQUENCE CHARACTERISTICS:
        (A) LENGTH: 335 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 141:

```
ACTTTATTTT CAAAACACTC ATATGTTGCA AAAAACACAT AGAAAAATAA AGTTTGGTGG      60

GGGTGCTGAC TAAACTTCAA GTCACAGACT TTTATGTGAC AGATTGGAGC AGGGTTTGTT     120

ATGCATGTAG AGAACCCAAA CTAATTTATT AAACAGGATA GAAACAGGCT GTCTGGGTGA     180

AATGGTTCTG AGAACCATCC AATTCACCTG TCAGATGCTG ATANACTAGC TCTTCAGATG     240
```

```
TTTTTCTACC AGTTCAGAGA TNGGTTAATG ACTANTTCCA ATGGGGAAAA AGCAAGATGG        300

ATTCACAAAC CAAGTAATTT TAAACAAAGA CACTT                                  335
```

(2) INFORMATION FOR SEQ ID NO: 142:

(i) SEQUENCE CHARACTERISTICS:
        (A) LENGTH: 459 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 142:

```
ACCAGGTTAA TATTGCCACA TATATCCTTT CCAATTGCGG GCTAAACAGA CGTGTATTTA         60

GGGTTGTTTA AAGACAACCC AGCTTAATAT CAAGAGAAAT TGTGACCTTT CATGGAGTAT        120

CTGATGGAGA AAACACTGAG TTTTGACAAA TCTTATTTTA TTCAGATAGC AGTCTGATCA        180

CACATGGTCC AACAACACTC AAATAATAAA TCAAATATNA TCAGATGTTA AAGATTGGTC        240

TTCAAACATC ATAGCCAATG ATGCCCCGCT TGCCTATAAT CTCTCCGACA TAAAACCACA        300

TCAACACCTC AGTGGCCACC AAACCATTCA GCACAGCTTC CTTAACTGTG AGCTGTTTGA        360

AGCTACCAGT CTGAGCACTA TTGACTATNT TTTTCANGCT CTGAATAGCT CTAGGGATCT        420

CAGCANGGGT GGGAGGAACC AGCTCAACCT TGGCGTANT                               459
```

(2) INFORMATION FOR SEQ ID NO: 143:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 143:

```
ACATTTCCTT CCACCAAGTC AGGACTCCTG GCTTCTGTGG GAGTTCTTAT CACCTGAGGG         60

AAATCCAAAC AGTCTCTCCT AGAAAGGAAT AGTGTCACCA ACCCCACCCA TCTCCCTGAG        120

ACCATCCGAC TTCCCTGTGT                                                   140
```

(2) INFORMATION FOR SEQ ID NO: 144:

(i) SEQUENCE CHARACTERISTICS:
        (A) LENGTH: 164 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 144:

```
ACTTCAGTAA CAACATACAA TAACAACATT AAGTGTATAT TGCCATCTTT GTCATTTTCT         60

ATCTATACCA CTCTCCCTTC TGAAAACAAN AATCACTANC CAATCACTTA TACAAATTTG        120

AGGCAATTAA TCCATATTTG TTTTCAATAA GGAAAAAAAG ATGT                        164
```

(2) INFORMATION FOR SEQ ID NO: 145:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 145:

```
ACGTAGACCA TCCAACTTTG TATTTGTAAT GGCAAACATC CAGNAGCAAT TCCTAAACAA      60

ACTGGAGGGT ATTTATACCC AATTATCCCA TTCATTAACA TGCCCTCCTC CTCAGGCTAT     120

GCAGGACAGC TATCATAAGT CGGCCCAGGC ATCCAGATAC TACCATTTGT ATAAACTTCA     180

GTAGGGGAGT CCATCCAAGT GACAGGTCTA ATCAAAGGAG GAAATGGAAC ATAAGCCCAG     240

TAGTAAAATN TTGCTTAGCT GAAACAGCCA CAAAAGACTT ACCGCCGTGG TGATTACCAT     300

CAA                                                                  303
```

(2) INFORMATION FOR SEQ ID NO: 146:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 146:

```
ACTGCAGCTC AATTAGAAGT GGTCTCTGAC TTTCATCANC TTCTCCCTGG GCTCCATGAC      60

ACTGGCCTGG AGTGACTCAT TGCTCTGGTT GGTTGAGAGA GCTCCTTTGC CAACAGGCCT     120

CCAAGTCAGG GCTGGGATTT GTTTCCTTTC CACATTCTAG CAACAATATG CTGGCCACTT     180

CCTGAACAGG GAGGGTGGGA GGAGCCAGCA TGGAACAAGC TGCCACTTTC TAAAGTAGCC     240

AGACTTGCCC CTGGGCCTGT CACACCTACT GATGACCTTC TGTGCCTGCA GGATGGAATG     300

TAGGGGTGAG CTGTGTGACT CTATGGT                                        327
```

(2) INFORMATION FOR SEQ ID NO: 147:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 147:

```
ACATTGTTTT TTTGAGATAA AGCATTGANA GAGCTCTCCT TAACGTGACA CAATGGAAGG      60

ACTGAACAC ATACCCACAT CTTTGTTCTG AGGGATAATT TTCTGATAAA GTCTTGCTGT     120

ATATTCAAGC ACATATGTTA TATATTATTC AGTTCCATGT TTATAGCCTA GTT           173
```

(2) INFORMATION FOR SEQ ID NO: 148:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 148:

```
ACAACCACTT TATCTCATCG AATTTTTAAC CCAAACTCAC TCACTGTGCC TTTCTATCCT      60
ATGGGATATA TTATTTGATG CTCCATTTCA TCACACATAT ATGAATAATA CACTCATACT     120
GCCCTACTAC CTGCTGCAAT AATCACATTC CCTTCCTGTC CTGACCCTGA AGCCATTGGG     180
GTGGTCCTAG TGGCCATCAG TCCANGCCTG CACCTTGAGC CCTTGAGCTC CATTGCTCAC     240
NCCANCCCAC CTCACCGACC CCATCCTCTT ACACAGCTAC CTCCTTGCTC TCTAACCCCA     300
TAGATTATNT CCAAATTCAG TCAATTAAGT TACTATTAAC ACTCTACCCG ACATGTCCAG     360
CACCACTGGT AAGCCTTCTC CAGCCAACAC ACACACACAC ACACNCACAC ACACACATAT     420
CCAGGCACAG GCTACCTCAT CTTCACAATC ACCCCTTTAA TTACCATGCT ATGGTGG       477
```

(2) INFORMATION FOR SEQ ID NO: 149:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 149:

```
ACAGTTGTAT TATAATATCA AGAAATAAAC TTGCAATGAG AGCATTTAAG AGGGAAGAAC      60
TAACGTATTT TAGAGAGCCA AGGAAGGTTT CTGTGGGGAG TGGGATGTAA GGTGGGGCCT     120
GATGATAAAT AAGAGTCAGC CAGGTAAGTG GGTGGTGTGG TATGGGCACA GTGAAGAACA     180
TTTCAGGCAG AGGGAACAGC AGTGAAA                                        207
```

(2) INFORMATION FOR SEQ ID NO: 150:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 150:

```
ACCTTGATTT CATTGCTGCT CTGATGGAAA CCCAACTATC TAATTTAGCT AAAACATGGG      60
CACTTAAATG TGGTCAGTGT TTGGACTTGT TAACTANTGG CATCTTTGGG T              111
```

(2) INFORMATION FOR SEQ ID NO: 151:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 151:

AGCGCGGCAG GTCATATTGA ACATTCCAGA TACCTATCAT TACTCGATGC TGTTGATAAC      60

AGCAAGATGG CTTTGAACTC AGGGTCACCA CCAGCTATTG GACCTTACTA TGAAAACCAT     120

GGATACCAAC CGGAAAACCC CTATCCCGCA CAGCCCACTG TGGTCCCCAC TGTCTACGAG     180

GTGCATCCGG CTCAGT                                                     196

(2) INFORMATION FOR SEQ ID NO: 152:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 152:

ACAGCACTTT CACATGTAAG AAGGGAGAAA TTCCTAAATG TAGGAGAAAG ATAACAGAAC      60

CTTCCCCTTT TCATCTAGTG GTGGAAACCT GATGCTTTAT GTTGACAGGA ATAGAACCAG     120

GAGGGAGTTT GT                                                         132

(2) INFORMATION FOR SEQ ID NO: 153:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 153:

ACAANACCCA NGANAGGCCA CTGGCCGTGG TGTCATGGCC TCCAAACATG AAAGTGTCAG      60

CTTCTGCTCT TATGTCCTCA TCTGACAACT CTTTACCATT TTTATCCTCG CTCAGCAGGA     120

GCACATCAAT AAAGTCCAAA GTCTTGGACT TGGCCTTGGC TTGGAGGAAG TCATCAACAC     180

CCTGGCTAGT GAGGGTGCGG CGCCGCTCCT GGATGACGGC ATCTGTGAAG TCGTGCACCA     240

GTCTGCAGGC CCTGTGGAAG CGCCGTCCAC ACGGAGTNAG GAATT                     285

(2) INFORMATION FOR SEQ ID NO: 154:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: cDNA

```
    (vi) ORIGINAL SOURCE:
         (A) ORGANISM: Homo sapiens (xi) SEQUENCE DESCRIPTION: SEQ ID NO: 154:

ACCACAGTCC TGTTGGGCCA GGGCTTCATG ACCCTTTCTG TGAAAAGCCA TATTATCACC      60

ACCCCAAATT TTTCCTTAAA TATCTTTAAC TGAAGGGGTC AGCCTCTTGA CTGCAAAGAC     120

CCTAAGCCGG TTACACAGCT AACTCCCACT GGCCCTGATT TGTGAAATTG CTGCTGCCTG     180

ATTGGCACAG GAGTCGAAGG TGTTCAGCTC CCCTCCTCCG TGGAACGAGA CTCTGATTTG     240

AGTTTCACAA ATTCTCGGGC CACCTCGTCA TTGCTCCTCT GAAATAAAAT CCGGAGAATG     300

GTCAGGCCTG TCTCATCCAT ATGGATCTTC CGG                                 333

(2) INFORMATION FOR SEQ ID NO: 155:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 155:

ACTGGAAATA ATAAAACCCA CATCACAGTG TTGTGTCAAA GATCATCAGG GCATGGATGG      60

GAAAGTGCTT TGGGAACTGT AAAGTGCCTA ACACATGATC GATGATTTTT GTTATAATAT     120

TTGAATCACG GTGCATACAA ACTCTCCTGC CTGCTCCTCC TGGGCCCCAG CCCCAGCCCC     180

ATCACAGCTC ACTGCTCTGT TCATCCAGGC CCAGCATGTA GTGGCTGATT CTTCTTGGCT     240

GCTTTTAGCC TCCANAAGTT TCTCTGAAGC CAACCAAACC TCTANGTGTA AGGCATGCTG     300

GCCCTGGT                                                             308

(2) INFORMATION FOR SEQ ID NO: 156:

(i) SEQUENCE CHARACTERISTICS:
        (A) LENGTH: 295 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 156:

ACCTTGCTCG GTGCTTGGAA CATATTAGGA ACTCAAAATA TGAGATGATA ACAGTGCCTA      60

TTATTGATTA CTGAGAGAAC TGTTAGACAT TTAGTTGAAG ATTTTCTACA CAGGAACTGA     120

GAATAGGAGA TTATGTTTGG CCCTCATATT CTCTCCTATC CTCCTTGCCT CATTCTATGT     180

CTAATATATT CTCAATCAAA TAAGGTTAGC ATAATCAGGA AATCGACCAA ATACCAATAT     240

AAAACCAGAT GTCTATCCTT AAGATTTTCA AATAGAAAAC AAATTAACAG ACTAT          295

(2) INFORMATION FOR SEQ ID NO: 157:

(i) SEQUENCE CHARACTERISTICS:
        (A) LENGTH: 126 base pairs
        (B) TYPE: nucleic acid
        (C) STRANDEDNESS: single
```

(D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 157:

ACAAGTTTAA ATAGTGCTGT CACTGTGCAT GTGCTGAAAT GTGAAATCCA CCACATTTCT      60

GAAGAGCAAA ACAAATTCTG TCATGTAATC TCTATCTTGG GTCGTGGGTA TATCTGTCCC     120

CTTAGT                                                                126

(2) INFORMATION FOR SEQ ID NO: 158:

(i) SEQUENCE CHARACTERISTICS:
            (A) LENGTH: 442 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 158:

ACCCACTGGT CTTGGAAACA CCCATCCTTA ATACGATGAT TTTTCTGTCG TGTGAAAATG      60

AANCCAGCAG GCTGCCCCTA GTCAGTCCTT CCTTCCAGAG AAAAAGAGAT TTGAGAAAGT     120

GCCTGGGTAA TTCACCATTA ATTTCCTCCC CCAAACTCTC TGAGTCTTCC CTTAATATTT     180

CTGGTGGTTC TGACCAAAGC AGGTCATGGT TTGTTGAGCA TTTGGGATCC CAGTGAAGTA     240

NATGTTTGTA GCCTTGCATA CTTAGCCCTT CCCACGCACA AACGGAGTGG CAGAGTGGTG     300

CCAACCCTGT TTTCCCAGTC CACGTAGACA GATTCACAGT GCGGAATTCT GGAAGCTGGA     360

NACAGACGGG CTCTTTGCAG AGCCGGGACT CTGAGANGGA CATGAGGGCC TCTGCCTCTG     420

TGTTCATTCT CTGATGTCCT GT                                             442

(2) INFORMATION FOR SEQ ID NO: 159:

(i) SEQUENCE CHARACTERISTICS:
            (A) LENGTH: 498 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 159:

ACTTCCAGGT AACGTTGTTG TTTCCGTTGA GCCTGAACTG ATGGGTGACG TTGTAGGTTC      60

TCCAACAAGA ACTGAGGTTG CAGAGCGGGT AGGGAAGAGT GCTGTTCCAG TTGCACCTGG     120

GCTGCTGTGG ACTGTTGTTG ATTCCTCACT ACGGCCCAAG GTTGTGGAAC TGGCANAAAG     180

GTGTGTTGTT GGANTTGAGC TCGGGCGGCT GTGGTAGGTT GTGGGCTCTT CAACAGGGGC     240

TGCTGTGGTG CCGGGANGTG AANGTGTTGT GTCACTTGAG CTTGGCCAGC TCTGGAAAGT     300

ANTANATTCT TCCTGAAGGC CAGCGCTTGT GGAGCTGGCA NGGGTCANTG TTGTGTGTAA     360

CGAACCAGTG CTGCTGTGGG TGGGTGTANA TCCTCCACAA AGCCTGAAGT TATGGTGTCN     420

TCAGGTAANA ATGTGGTTTC AGTGTCCCTG GGCNGCTGTG GAAGGTTGTA NATTGTCACC     480

```
AAGGGAATAA GCTGTGGT                                                        498

(2) INFORMATION FOR SEQ ID NO: 160:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 160:

ACCTGCATCC AGCTTCCCTG CCAAACTCAC AAGGAGACAT CAACCTCTAG ACAGGGAAAC    60

AGCTTCAGGA TACTTCCAGG AGACAGAGCC ACCAGCAGCA AAACAAATAT TCCCATGCCT   120

GGAGCATGGC ATAGAGGAAG CTGANAAATG TGGGGTCTGA GGAAGCCATT TGAGTCTGGC   180

CACTAGACAT CTCATCAGCC ACTTGTGTGA AGAGATGCCC CATGACCCCA GATGCCTCTC   240

CCACCCTTAC CTCCATCTCA CACACTTGAG CTTTCCACTC TGTATAATTC TAACATCCTG   300

GAGAAAAATG GCAGTTTGAC CGAACCTGTT CACAACGGTA GAGGCTGATT TCTAACGAAA   360

CTTGTAGAAT GAAGCCTGGA                                               380

(2) INFORMATION FOR SEQ ID NO: 161:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 161:

ACTCCACATC CCCTCTGAGC AGGCGGTTGT CGTTCAAGGT GTATTTGGCC TTGCCTGTCA    60

CACTGTCCAC TGGCCCCTTA TCCACTTGGT GCTTAATCCC TCGAAAGAGC ATGT         114

(2) INFORMATION FOR SEQ ID NO: 162:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 162:

ACTTTCTGAA TCGAATCAAA TGATACTTAG TGTAGTTTTA ATATCCTCAT ATATATCAAA    60

GTTTTACTAC TCTGATAATT TTGTAAACCA GGTAACCAGA ACATCCAGTC ATACAGCTTT   120

TGGTGATATA TAACTTGGCA ATAACCCAGT CTGGTGATAC ATAAAACTAC TCACTGT      177

(2) INFORMATION FOR SEQ ID NO: 163:

(i) SEQUENCE CHARACTERISTICS:
        (A) LENGTH: 137 base pairs
```

(B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 163:

CATTTATACA GACAGGCGTG AAGACATTCA CGACAAAAAC GCGAAATTCT ATCCCGTGAC      60

CANAGAAGGC AGCTACGGCT ACTCCTACAT CCTGGCGTGG GTGGCCTTCG CCTGCACCTT     120

CATCAGCGGC ATGATGT                                                   137

(2) INFORMATION FOR SEQ ID NO: 164:

(i) SEQUENCE CHARACTERISTICS:
        (A) LENGTH: 469 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 164:

CTTATCACAA TGAATGTTCT CCTGGGCAGC GTTGTGATCT TTGCCACCTT CGTGACTTTA      60

TGCAATGCAT CATGCTATTT CATACCTAAT GAGGGAGTTC CAGGAGATTC AACCAGGAAA     120

TGCATGGATC TCAAAGGAAA CAAACACCCA ATAAACTCGG AGTGGCAGAC TGACAACTGT     180

GAGACATGCA CTTGCTACGA AACAGAAATT TCATGTTGCA CCCTTGTTTC TACACCTGTG     240

GGTTATGACA AAGACAACTG CCAAAGAATC TTCAAGAAGG AGGACTGCAA GTATATCGTG     300

GTGGAGAAGA AGGACCCAAA AAAGACCTGT TCTGTCAGTG AATGGATAAT CTAATGTGCT     360

TCTAGTAGGC ACAGGGCTCC CAGGCCAGGC CTCATTCTCC TCTGGCCTCT AATAGTCAAT     420

GATTGTGTAG CCATGCCTAT CAGTAAAAAG ATNTTTGAGC AAACACTTT                469

(2) INFORMATION FOR SEQ ID NO: 165:

(i) SEQUENCE CHARACTERISTICS:
        (A) LENGTH: 195 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 165:

ACAGTTTTTT ATANATATCG ACATTGCCGG CACTTGTGTT CAGTTTCATA AAGCTGGTGG      60

ATCCGCTGTC ATCCACTATT CCTTGGCTAG AGTAAAAATT ATTCTTATAG CCCATGTCCC     120

TGCAGGCCGC CCGCCCGTAG TTCTCGTTCC AGTCGTCTTG GCACACAGGG TGCCAGGACT     180

TCCTCTGAGA TGAGT                                                     195

(2) INFORMATION FOR SEQ ID NO: 166:

(i) SEQUENCE CHARACTERISTICS:
        (A) LENGTH: 383 base pairs
        (B) TYPE: nucleic acid

```
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 166:

ACATCTTAGT AGTGTGGCAC ATCAGGGGGC CATCAGGGTC ACAGTCACTC ATAGCCTCGC      60

CGAGGTCGGA GTCCACACCA CCGGTGTAGG TGTGCTCAAT CTTGGGCTTG GCGCCCACCT     120

TTGGAGAAGG GATATGCTGC ACACACATGT CCACAAAGCC TGTGAACTCG CCAAAGAATT     180

TTTGCAGACC AGCCTGAGCA AGGGGCGGAT GTTCAGCTTC AGCTCCTCCT TCGTCAGGTG     240

GATGCCAACC TCGTCTANGG TCCGTGGGAA GCTGGTGTCC ACNTCACCTA CAACCTGGGC     300

GANGATCTTA TAAAGAGGCT CCNAGATAAA CTCCACGAAA CTTCTCTGGG AGCTGCTAGT     360

NGGGGCCTTT TTGGTGAACT TTC                                             383

(2) INFORMATION FOR SEQ ID NO: 167:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 167:

ACAGAGCCAG ACCTTGGCCA TAAATGAANC AGAGATTAAG ACTAAACCCC AAGTCGANAT      60

TGGAGCAGAA ACTGGAGCAA GAAGTGGGCC TGGGGCTGAA GTAGAGACCA AGGCCACTGC     120

TATANCCATA CACAGAGCCA ACTCTCAGGC CAAGGCNATG GTTGGGGCAG ANCCAGAGAC     180

TCAATCTGAN TCCAAAGTGG TGGCTGGAAC ACTGGTCATG ACANAGGCAG TGACTCTGAC     240

TGANGTC                                                               247

(2) INFORMATION FOR SEQ ID NO: 168:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 168:

ACTTCTAAGT TTTCTAGAAG TGGAAGGATT GTANTCATCC TGAAAATGGG TTTACTTCAA      60

AATCCCTCAN CCTTGTTCTT CACNACTGTC TATACTGANA GTGTCATGTT TCCACAAAGG     120

GCTGACACCT GAGCCTGNAT TTTCACTCAT CCCTGAGAAG CCCTTTCCAG TAGGGTGGGC     180

AATTCCCAAC TTCCTTGCCA CAAGCTTCCC AGGCTTTCTC CCCTGGAAAA CTCCAGCTTG     240

AGTCCCAGAT ACACTCATGG GCTGCCCTGG GCA                                  273

(2) INFORMATION FOR SEQ ID NO: 169:
```

```
    (i) SEQUENCE CHARACTERISTICS:
        (A) LENGTH: 431 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 169:

ACAGCCTTGG CTTCCCCAAA CTCCACAGTC TCAGTGCAGA AAGATCATCT TCCAGCAGTC      60

AGCTCAGACC AGGGTCAAAG GATGTGACAT CAACAGTTTC TGGTTTCAGA ACAGGTTCTA     120

CTACTGTCAA ATGACCCCCC ATACTTCCTC AAAGGCTGTG GTAAGTTTTG CACAGGTGAG     180

GGCAGCAGAA AGGGGGTANT TACTGATGGA CACCATCTTC TCTGTATACT CCACACTGAC     240

CTTGCCATGG GCAAAGGCCC CTACCACAAA AACAATAGGA TCACTGCTGG GCACCAGCTC     300

ACGCACATCA CTGACAACCG GGATGGAAAA AGAANTGCCA ACTTTCATAC ATCCAACTGG     360

AAAGTGATCT GATACTGGAT TCTTAATTAC CTTCAAAAGC TTCTGGGGGC CATCAGCTGC     420

TCGAACACTG A                                                         431

(2) INFORMATION FOR SEQ ID NO: 170:

(i) SEQUENCE CHARACTERISTICS:
        (A) LENGTH: 266 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 170:

ACCTGTGGGC TGGGCTGTTA TGCCTGTGCC GGCTGCTGAA AGGGAGTTCA GAGGTGGAGC      60

TCAAGGAGCT CTGCAGGCAT TTTGCCAANC CTCTCCANAG CANAGGGAGC AACCTACACT     120

CCCCGCTAGA AAGACACCAG ATTGGAGTCC TGGGAGGGGG AGTTGGGGTG GGCATTTGAT     180

GTATACTTGT CACCTGAATG AANGAGCCAG AGAGGAANGA GACGAANATG ANATTGGCCT     240

TCAAAGCTAG GGGTCTGGCA GGTGGA                                         266

(2) INFORMATION FOR SEQ ID NO: 171:

(i) SEQUENCE CHARACTERISTICS:
        (A) LENGTH: 1248 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 171:

GGCAGCCAAA TCATAAACGG CGAGGACTGC AGCCCGCACT CGCAGCCCTG GCAGGCGGCA      60

CTGGTCATGG AAAACGAATT GTTCTGCTCG GGCGTCCTGG TGCATCCGCA GTGGGTGCTG     120

TCAGCCGCAC ACTGTTTCCA GAAGTGAGTG CAGAGCTCCT ACACCATCGG GCTGGGCCTG     180

CACAGTCTTG AGGCCGACCA AGAGCCAGGG AGCCAGATGG TGGAGGCCAG CCTCTCCGTA     240
```

```
CGGCACCCAG AGTACAACAG ACCCTTGCTC GCTAACGACC TCATGCTCAT CAAGTTGGAC      300

GAATCCGTGT CCGAGTCTGA CACCATCCGG AGCATCAGCA TTGCTTCGCA GTGCCCTACC      360

GCGGGGAACT CTTGCCTCGT TTCTGGCTGG GGTCTGCTGG CGAACGGCAG AATGCCTACC      420

GTGCTGCAGT GCGTGAACGT GTCGGTGGTG TCTGAGGAGG TCTGCAGTAA GCTCTATGAC      480

CCGCTGTACC ACCCCAGCAT GTTCTGCGCC GGCGGAGGGC AAGACCAGAA GGACTCCTGC      540

AACGGTGACT CTGGGGGGCC CCTGATCTGC AACGGGTACT TGCAGGGCCT TGTGTCTTTC      600

GGAAAAGCCC CGTGTGGCCA AGTTGGCGTG CCAGGTGTCT ACACCAACCT CTGCAAATTC      660

ACTGAGTGGA TAGAGAAAAC CGTCCAGGCC AGTTAACTCT GGGGACTGGG AACCCATGAA      720

ATTGACCCCC AAATACATCC TGCGGAAGGA ATTCAGGAAT ATCTGTTCCC AGCCCCTCCT      780

CCCTCAGGCC CAGGAGTCCA GGCCCCCAGC CCCTCCTCCC TCAAACCAAG GGTACAGATC      840

CCCAGCCCCT CCTCCCTCAG ACCCAGGAGT CCAGACCCCC CAGCCCCTCC TCCCTCAGAC      900

CCAGGAGTCC AGCCCCTCCT CCCTCAGACC CAGGAGTCCA GACCCCCAG CCCCTCCTCC      960

CTCAGACCCA GGGGTCCAGG CCCCCAACCC CTCCTCCCTC AGACTCAGAG GTCCAAGCCC     1020

CCAACCCNTC ATTCCCCAGA CCCAGAGGTC CAGGTCCCAG CCCCTCNTCC CTCAGACCCA     1080

GCGGTCCAAT GCCACCTAGA CTNTCCCTGT ACACAGTGCC CCCTTGTGGC ACGTTGACCC     1140

AACCTTACCA GTTGGTTTTT CATTTTTNGT CCCTTTCCCC TAGATCCAGA AATAAAGTTT     1200

AAGAGAAGNG CAAAAAAAAA AAAAAAAAAA AAAAAAAAAA AAAAAAA                   1248
```

(2) INFORMATION FOR SEQ ID NO: 172:

(i) SEQUENCE CHARACTERISTICS:
        (A) LENGTH: 159 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 172:

```
Met Val Glu Ala Ser Leu Ser Val Arg His Pro Glu Tyr Asn Arg Pro
1               5                   10                  15

Leu Leu Ala Asn Asp Leu Met Leu Ile Lys Leu Asp Glu Ser Val Ser
            20                  25                  30

Glu Ser Asp Thr Ile Arg Ser Ile Ser Ile Ala Ser Gln Cys Pro Thr
        35                  40                  45

Ala Gly Asn Ser Cys Leu Val Ser Gly Trp Gly Leu Leu Ala Asn Gly
    50                  55                  60

Arg Met Pro Thr Val Leu Gln Cys Val Asn Val Ser Val Val Ser Glu
65                  70                  75                  80

Glu Val Cys Ser Lys Leu Tyr Asp Pro Leu Tyr His Pro Ser Met Phe
                85                  90                  95

Cys Ala Gly Gly Gly Gln Xaa Gln Xaa Asp Ser Cys Asn Gly Asp Ser
            100                 105                 110

Gly Gly Pro Leu Ile Cys Asn Gly Tyr Leu Gln Gly Leu Val Ser Phe
        115                 120                 125

Gly Lys Ala Pro Cys Gly Gln Val Gly Val Pro Gly Val Tyr Thr Asn
    130                 135                 140

Leu Cys Lys Phe Thr Glu Trp Ile Glu Lys Thr Val Gln Ala Ser
145                 150                 155
```

(2) INFORMATION FOR SEQ ID NO: 173:

(i) SEQUENCE CHARACTERISTICS:
        (A) LENGTH: 1265 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 173:

```
GGCAGCCCGC ACTCGCAGCC CTGGCAGGCG GCACTGGTCA TGGAAAACGA ATTGTTCTGC      60

TCGGGCGTCC TGGTGCATCC GCAGTGGGTG CTGTCAGCCG CACACTGTTT CCAGAACTCC     120

TACACCATCG GGCTGGGCCT GCACAGTCTT GAGGCCGACC AAGAGCCAGG GAGCCAGATG     180

GTGGAGGCCA GCCTCTCCGT ACGGCACCCA GAGTACAACA GACCCTTGCT CGCTAACGAC     240

CTCATGCTCA TCAAGTTGGA CGAATCCGTG TCCGAGTCTG ACACCATCCG GAGCATCAGC     300

ATTGCTTCGC AGTGCCCTAC CGCGGGGAAC TCTTGCCTCG TTTCTGGCTG GGGTCTGCTG     360

GCGAACGGTG AGCTCACGGG TGTGTGTCTG CCCTCTTCAA GGAGGTCCTC TGCCCAGTCG     420

CGGGGGCTGA CCCAGAGCTC TGCGTCCCAG GCAGAATGCC TACCGTGCTG CAGTGCGTGA     480

ACGTGTCGGT GGTGTCTGAG GAGGTCTGCA GTAAGCTCTA TGACCCGCTG TACCACCCCA     540

GCATGTTCTG CGCCGGCGGA GGGCAAGACC AGAAGGACTC CTGCAACGGT GACTCTGGGG     600

GGCCCCTGAT CTGCAACGGG TACTTGCAGG GCCTTGTGTC TTTCGGAAAA GCCCCGTGTG     660

GCCAAGTTGG CGTGCCAGGT GTCTACACCA ACCTCTGCAA ATTCACTGAG TGGATAGAGA     720

AAACCGTCCA GGCCAGTTAA CTCTGGGGAC TGGGAACCCA TGAAATTGAC CCCCAAATAC     780

ATCCTGCGGA AGGAATTCAG GAATATCTGT TCCCAGCCCC TCCTCCCTCA GGCCCAGGAG     840

TCCAGGCCCC CAGCCCCTCC TCCCTCAAAC CAAGGGTACA GATCCCCAGC CCCTCCTCCC     900

TCAGACCCAG GAGTCCAGAC CCCCCAGCCC CTCCTCCCTC AGACCCAGGA GTCCAGCCCC     960

TCCTCCNTCA GACCCAGGAG TCCAGACCCC CCAGCCCCTC CTCCCTCAGA CCCAGGGGTT    1020

GAGGCCCCCA ACCCCTCCTC CTTCAGAGTC AGAGGTCCAA GCCCCCAACC CCTCGTTCCC    1080

CAGACCCAGA GGTNNAGGTC CCAGCCCCTC TTCCNTCAGA CCCAGNGGTC CAATGCCACC    1140

TAGATTTTCC CTGNACACAG TGCCCCCTTG TGGNANGTTG ACCCAACCTT ACCAGTTGGT    1200

TTTTCATTTT TNGTCCCTTT CCCCTAGATC CAGAAATAAA GTTAAGAGA NGNGCAAAAA     1260

AAAAA                                                                1265
```

(2) INFORMATION FOR SEQ ID NO: 174:

(i) SEQUENCE CHARACTERISTICS:
        (A) LENGTH: 1459 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 174:

```
GGTCAGCCGC ACACTGTTTC CAGAAGTGAG TGCAGAGCTC CTACACCATC GGGCTGGGCC      60
```

```
TGCACAGTCT TGAGGCCGAC CAAGAGCCAG GGAGCCAGAT GGTGGAGGCC AGCCTCTCCG      120

TACGGCACCC AGAGTACAAC AGACCCTTGC TCGCTAACGA CCTCATGCTC ATCAAGTTGG      180

ACGAATCCGT GTCCGAGTCT GACACCATCC GGAGCATCAG CATTGCTTCG CAGTGCCCTA      240

CCGCGGGGAA CTCTTGCCTC GTTTCTGGCT GGGGTCTGCT GGCGAACGGT GAGCTCACGG      300

GTGTGTGTCT GCCCTCTTCA AGGAGGTCCT CTGCCCAGTC GCGGGGCTG ACCCAGAGCT       360

CTGCGTCCCA GGCAGAATGC CTACCGTGCT GCAGTGCGTG AACGTGTCGG TGGTGTCTGA      420

NGAGGTCTGC ANTAAGCTCT ATGACCCGCT GTACCACCCC ANCATGTTCT GCGCCGGCGG      480

AGGGCAAGAC CAGAAGGACT CCTGCAACGT GAGAGAGGGG AAAGGGGAGG GCAGGCGACT     540

CAGGGAAGGG TGGAGAAGGG GGAGACAGAG ACACACAGGG CCGCATGGCG AGATGCAGAG      600

ATGGAGAGAC ACACAGGGAG ACAGTGACAA CTAGAGAGAG AAACTGAGAG AAACAGAGAA      660

ATAAACACAG GAATAAAGAG AAGCAAAGGA AGAGAGAAAC AGAAACAGAC ATGGGGAGGC      720

AGAAACACAC ACACATAGAA ATGCAGTTGA CCTTCCAACA GCATGGGGCC TGAGGGCGGT      780

GACCTCCACC CAATAGAAAA TCCTCTTATA ACTTTTGACT CCCCAAAAAC CTGACTAGAA      840

ATAGCCTACT GTTGACGGGG AGCCTTACCA ATAACATAAA TAGTCGATTT ATGCATACGT      900

TTTATGCATT CATGATATAC CTTTGTTGGA ATTTTTTGAT ATTTCTAAGC TACACAGTTC      960

GTCTGTGAAT TTTTTTAAAT TGTTGCAACT CTCCTAAAAT TTTTCTGATG TGTTTATTGA     1020

AAAAATCCAA GTATAAGTGG ACTTGTGCAT TCAAACCAGG GTTGTTCAAG GGTCAACTGT     1080

GTACCCAGAG GGAAACAGTG ACACAGATTC ATAGAGGTGA AACACGAAGA GAAACAGGAA     1140

AAATCAAGAC TCTACAAAGA GGCTGGGCAG GGTGGCTCAT GCCTGTAATC CCAGCACTTT     1200

GGGAGGCGAG GCAGGCAGAT CACTTGAGGT AAGGAGTTCA AGACCAGCCT GGCCAAAATG     1260

GTGAAATCCT GTCTGTACTA AAAATACAAA AGTTAGCTGG ATATGGTGGC AGGCGCCTGT     1320

AATCCCAGCT ACTTGGGAGG CTGAGGCAGG AGAATTGCTT GAATATGGGA GGCAGAGGTT     1380

GAAGTGAGTT GAGATCACAC CACTATACTC CAGCTGGGGC AACAGAGTAA GACTCTGTCT     1440

CAAAAAAAAA AAAAAAAA                                                   1459

(2) INFORMATION FOR SEQ ID NO: 175:

(i) SEQUENCE CHARACTERISTICS:
        (A) LENGTH: 1167 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 175:

GCGCAGCCCT GGCAGGCGGC ACTGGTCATG GAAAACGAAT TGTTCTGCTC GGGCGTCCTG       60

GTGCATCCGC AGTGGGTGCT GTCAGCCGCA CACTGTTTCC AGAACTCCTA CACCATCGGG      120

CTGGGCCTGC ACAGTCTTGA GGCCGACCAA GAGCCAGGGA GCCAGATGGT GGAGGCCAGC      180

CTCTCCGTAC GGCACCCAGA GTACAACAGA CTCTTGCTCG CTAACGACCT CATGCTCATC      240

AAGTTGGACG AATCCGTGTC CGAGTCTGAC ACCATCCGGA GCATCAGCAT TGCTTCGCAG      300

TGCCCTACCG CGGGGAACTC TTGCCTCGTN TCTGGCTGGG GTCTGCTGGC GAACGGCAGA      360

ATGCCTACCG TGCTGCACTG CGTGAACGTG TCGGTGGTGT CTGAGGANGT CTGCAGTAAG      420

CTCTATGACC CGCTGTACCA CCCCAGCATG TTCTGCGCCG CGGAGGGCA AGACCAGAAG       480
```

-continued

```
GACTCCTGCA ACGGTGACTC TGGGGGGCCC CTGATCTGCA ACGGGTACTT GCAGGGCCTT    540

GTGTCTTTCG GAAAAGCCCC GTGTGGCCAA CTTGGCGTGC CAGGTGTCTA CACCAACCTC    600

TGCAAATTCA CTGAGTGGAT AGAGAAAACC GTCCAGNCCA GTTAACTCTG GGGACTGGGA    660

ACCCATGAAA TTGACCCCCA AATACATCCT GCGGAANGAA TTCAGGAATA TCTGTTCCCA    720

GCCCCTCCTC CCTCAGGCCC AGGAGTCCAG GCCCCCAGCC CCTCCTCCCT CAAACCAAGG    780

GTACAGATCC CCAGCCCCTC CTCCCTCAGA CCCAGGAGTC CAGACCCCCC AGCCCCTCNT    840

CCNTCAGACC CAGGAGTCCA GCCCCTCCTC CNTCAGACGC AGGAGTCCAG ACCCCCCAGC    900

CCNTCNTCCG TCAGACCCAG GGGTGCAGGC CCCCAACCCC TCNTCCNTCA GAGTCAGAGG    960

TCCAAGCCCC CAACCCCTCG TTCCCCAGAC CCAGAGGTNC AGGTCCCAGC CCCTCCTCCC   1020

TCAGACCCAG CGGTCCAATG CCACCTAGAN TNTCCCTGTA CACAGTGCCC CCTTGTGGCA   1080

NGTTGACCCA ACCTTACCAG TTGGTTTTTC ATTTTTTGTC CCTTTCCCCT AGATCCAGAA   1140

ATAAAGTNTA AGAGAAGCGC AAAAAAA                                      1167
```

(2) INFORMATION FOR SEQ ID NO: 176:

(i) SEQUENCE CHARACTERISTICS:
        (A) LENGTH: 205 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 176:

```
Met Glu Asn Glu Leu Phe Cys Ser Gly Val Leu Val His Pro Gln Trp
 1               5                  10                  15

Val Leu Ser Ala Ala His Cys Phe Gln Asn Ser Tyr Thr Ile Gly Leu
                20                  25                  30

Gly Leu His Ser Leu Glu Ala Asp Gln Glu Pro Gly Ser Gln Met Val
            35                  40                  45

Glu Ala Ser Leu Ser Val Arg His Pro Glu Tyr Asn Arg Leu Leu Leu
50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Gly Arg Met
            100                 105                 110

Pro Thr Val Leu His Cys Val Asn Val Ser Val Val Ser Glu Xaa Val
        115                 120                 125

Cys Ser Lys Leu Tyr Asp Pro Leu Tyr His Pro Ser Met Phe Cys Ala
    130                 135                 140

Gly Gly Gly Gln Asp Gln Lys Asp Ser Cys Asn Gly Asp Ser Gly Gly
145                 150                 155                 160

Pro Leu Ile Cys Asn Gly Tyr Leu Gln Gly Leu Val Ser Phe Gly Lys
                165                 170                 175

Ala Pro Cys Gly Gln Leu Gly Val Pro Gly Val Tyr Thr Asn Leu Cys
            180                 185                 190

Lys Phe Thr Glu Trp Ile Glu Lys Thr Val Gln Xaa Ser
        195                 200                 205
```

(2) INFORMATION FOR SEQ ID NO: 177:

(i) SEQUENCE CHARACTERISTICS:
        (A) LENGTH: 1119 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 177:

```
GCGCACTCGC AGCCCTGGCA GGCGGCACTG GTCATGGAAA ACGAATTGTT CTGCTCGGGC    60
GTCCTGGTGC ATCCGCAGTG GGTGCTGTCA GCCGCACACT GTTTCCAGAA CTCCTACACC   120
ATCGGGCTGG GCCTGCACAG TCTTGAGGCC GACCAAGAGC CAGGGAGCCA GATGGTGGAG   180
GCCAGCCTCT CCGTACGGCA CCCAGAGTAC AACAGACCCT TGCTCGCTAA CGACCTCATG   240
CTCATCAAGT TGGACGAATC CGTGTCCGAG TCTGACACCA TCCGGAGCAT CAGCATTGCT   300
TCGCAGTGCC CTACCGCGGG GAACTCTTGC CTCGTTTCTG GCTGGGGTCT GCTGGCGAAC   360
GATGCTGTGA TTGCCATCCA GTCCCAGACT GTGGGAGGCT GGGAGTGTGA AAAGCTTTCC   420
CAACCCTGGC AGGGTTGTAC CATTTCGGCA ACTTCCAGTG CAAGGACGTC CTGCTGCATC   480
CTCACTGGGT GCTCACTACT GCTCACTGCA TCACCCGGAA CACTGTGATC AACTAGCCAG   540
CACCATAGTT CTCCGAAGTC AGACTATCAT GATTACTGTG TTGACTGTGC TGTCTATTGT   600
ACTAACCATG CCGATGTTTA GGTGAAATTA GCGTCACTTG GCCTCAACCA TCTTGGTATC   660
CAGTTATCCT CACTGAATTG AGATTTCCTG CTTCAGTGTC AGCCATTCCC ACATAATTTC   720
TGACCTACAG AGGTGAGGGA TCATATAGCT CTTCAAGGAT GCTGGTACTC CCCTCACAAA   780
TTCATTTCTC CTGTTGTAGT GAAAGGTGCG CCCTCTGGAG CCTCCCAGGG TGGGTGTGCA   840
GGTCACAATG ATGAATGTAT GATCGTGTTC CCATTACCCA AAGCCTTTAA ATCCCTCATG   900
CTCAGTACAC CAGGGCAGGT CTAGCATTTC TTCATTTAGT GTATGCTGTC CATTCATGCA   960
ACCACCTCAG GACTCCTGGA TTCTCTGCCT AGTTGAGCTC CTGCATGCTG CCTCCTTGGG  1020
GAGGTGAGGG AGAGGGCCCA TGGTTCAATG GGATCTGTGC AGTTGTAACA CATTAGGTGC  1080
TTAATAAACA GAAGCTGTGA TGTTAAAAAA AAAAAAAA                          1119
```

(2) INFORMATION FOR SEQ ID NO: 178:

(i) SEQUENCE CHARACTERISTICS:
        (A) LENGTH: 164 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 178:

```
Met Glu Asn Glu Leu Phe Cys Ser Gly Val Leu Val His Pro Gln Trp
1               5                   10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
        35                  40                  45
```

-continued

```
Glu Ala Ser Leu Ser Val Arg His Pro Glu Tyr Asn Arg Pro Leu Leu
    50              55                  60
Ala Asn Asp Leu Met Leu Ile Lys Leu Asp Glu Ser Val Ser Glu Ser
65              70              75                      80
Asp Thr Ile Arg Ser Ile Ser Ile Ala Ser Gln Cys Pro Thr Ala Gly
            85              90                      95
Asn Ser Cys Leu Val Ser Gly Trp Gly Leu Leu Ala Asn Asp Ala Val
            100             105                 110
Ile Ala Ile Gln Ser Xaa Thr Val Gly Gly Trp Glu Cys Glu Lys Leu
        115             120                 125
Ser Gln Pro Trp Gln Gly Cys Thr Ile Ser Ala Thr Ser Ser Ala Arg
    130             135                 140
Thr Ser Cys Cys Ile Leu Thr Gly Cys Ser Leu Leu Leu Thr Ala Ser
145             150             155                 160
Pro Gly Thr Leu
```